United States Patent
Lyden et al.

(10) Patent No.: US 11,971,402 B2
(45) Date of Patent: Apr. 30, 2024

(54) METHODS AND REAGENTS FOR DETERMINATION AND TREATMENT OF ORGANOTROPIC METASTASIS

(71) Applicant: CORNELL UNIVERSITY, Ithaca, NY (US)

(72) Inventors: David C. Lyden, New York, NY (US); Ayuko Hoshino, New York, NY (US); Bruno Da Silva, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 245 days.

(21) Appl. No.: 15/569,050

(22) PCT Filed: Apr. 25, 2016

(86) PCT No.: PCT/US2016/029219
§ 371 (c)(1),
(2) Date: Oct. 24, 2017

(87) PCT Pub. No.: WO2016/172710
PCT Pub. Date: Oct. 27, 2016

(65) Prior Publication Data
US 2019/0049435 A1 Feb. 14, 2019

Related U.S. Application Data

(60) Provisional application No. 62/242,723, filed on Oct. 16, 2015, provisional application No. 62/152,615, filed on Apr. 24, 2015.

(51) Int. Cl.
*C12Q 1/68* (2018.01)
*C12Q 1/6886* (2018.01)
*G01N 33/50* (2006.01)
*G01N 33/574* (2006.01)
*G16H 50/20* (2018.01)

(52) U.S. Cl.
CPC ........ *G01N 33/5076* (2013.01); *C12Q 1/6886* (2013.01); *G01N 33/5017* (2013.01); *G01N 33/5023* (2013.01); *G01N 33/5035* (2013.01); *G01N 33/57484* (2013.01); *G16H 50/20* (2018.01); *C12Q 2600/156* (2013.01)

(58) Field of Classification Search
CPC ....................................................... C12Q 1/68
See application file for complete search history.

(56) References Cited

U.S. PATENT DOCUMENTS

| | | | |
|---|---|---|---|
| 5,849,701 A | 12/1998 | Roberts et al. | |
| 7,147,852 B2 | 12/2006 | Gilbertson | |
| 7,511,056 B2 | 3/2009 | Diefenbacher et al. | |
| 8,158,589 B2 | 4/2012 | Herrerias et al. | |
| 8,569,462 B2 | 10/2013 | Bedinger et al. | |
| 8,691,944 B2 | 4/2014 | Clark et al. | |
| 9,816,998 B2 | 11/2017 | Lyden et al. | |
| 9,921,223 B2 | 3/2018 | Kalluri et al. | |
| 2008/0108552 A1* | 5/2008 | Hazlehurst ............. A61P 35/00 514/18.9 |
| 2010/0184046 A1 | 7/2010 | Klass et al. | |
| 2010/0196426 A1 | 8/2010 | Skog et al. | |
| 2011/0118298 A1 | 5/2011 | Fritz et al. | |
| 2011/0160210 A1 | 6/2011 | Fleenor et al. | |
| 2012/0208706 A1 | 8/2012 | Downing et al. | |
| 2013/0005599 A1 | 1/2013 | Klass | |
| 2013/0029339 A1 | 1/2013 | Skog et al. | |
| 2013/0177498 A1 | 7/2013 | Goldenberg et al. | |
| 2013/0287801 A1 | 10/2013 | Castronovo et al. | |
| 2014/0038901 A1* | 2/2014 | Lyden ................. C12Q 1/6886 514/19.8 |
| 2014/0045915 A1 | 2/2014 | Skog et al. | |
| 2014/0162888 A1 | 6/2014 | Kuslich et al. | |
| 2014/0227179 A1 | 8/2014 | Liu et al. | |
| 2015/0218651 A1 | 8/2015 | Lyden et al. | |
| 2017/0175200 A1 | 6/2017 | Lyden et al. | |
| 2018/0045728 A1 | 2/2018 | Kalluri et al. | |
| 2018/0203014 A1* | 7/2018 | Cheresh ............ G01N 33/57492 |

(Continued)

FOREIGN PATENT DOCUMENTS

| WO | 2005/091805 | 6/2005 |
|---|---|---|
| WO | 2009/100029 | 8/2009 |
| WO | 2010/056337 | 5/2010 |

(Continued)

OTHER PUBLICATIONS

Zimmer et al (Brain Research Bulletin, 1995, vol. 37. No.4, pp. 417-429).*
Mullamitha et al (Clinical Cancer Research, 2007, vol. 13, No. 7, pp. 2128-2135).*
Tauro et al., "Comparison of ultracentrifugation, density gradient separation, and immunoaffinity capture methods for isolating human colon cancer cell line LIM1863-derived exosomes", (2012) Methods 53: 293-304 (Year: 2012).*
Hood et al., "Exosomes Released by Melanoma Cells Prepare Sentinel Lymph Nodes for Tumor Metastasis", (2011) Cancer Res 71(11): 3792-3801 (Year: 2011).*
Wu et al., "Targeting aV-integrins decreased metastasis and increased survival in a nude rat breast cancer brain metastasis model", (2012) J Neurooncol 110: 27-36 (Year: 2012).*

(Continued)

*Primary Examiner* — Jehanne S Sitton
(74) *Attorney, Agent, or Firm* — Troutman Pepper Hamilton Sanders LLP (Rochester)

(57) ABSTRACT

The present invention relates to methods and kits for prognosing, treating, and managing treatment of cancer in a subject. The methods involve selecting a subject having cancer and obtaining, from the selected subject, a sample containing exosomes or an S100 molecule containing sample. The exosomes or S100 molecule containing sample, respectively, are then contacted with one or more reagents suitable to detect higher or lower levels or the presence or absence of one or more integrins on said exosomes or higher or lower levels or the presence or absence of one or more S100 molecules in the S100 molecule containing sample. The cancer is then prognosed, treatment is administered, or treatment is managed.

15 Claims, 14 Drawing Sheets

Specification includes a Sequence Listing.

(56) References Cited

U.S. PATENT DOCUMENTS

2018/0231558 A1 8/2018 Lyden et al.
2019/0049435 A1 2/2019 Lyden et al.

FOREIGN PATENT DOCUMENTS

| WO | 2010/141955 | 12/2010 |
|---|---|---|
| WO | 2012/031008 | 3/2012 |
| WO | 2012/135844 | 10/2012 |
| WO | 2013/028788 | 2/2013 |
| WO | 2013/134786 | 9/2013 |
| WO | 2014/028862 | 2/2014 |
| WO | WO-2014037332 A1 * | 3/2014 |
| WO | 2014/055775 | 4/2014 |
| WO | 2014/062978 | 4/2014 |

OTHER PUBLICATIONS

Stoeltzing et al., "Inhibition of Integrin 51 Function With a Small Peptide (ATN-161) Plus Continuous 5-FU Infusion Reduces Colorectal Liver Metastases and Improves Survival in Mice", (2003), Int J Cancer 104: 496-503 (Year: 2003).*
Jahangiri et al., b1 Integrin: Critical Path to Antiangiogenic Therapy Resistance and Beyond, (2013) Cancer Res 74: 3-7 (Year: 2013).*
O'Day et al., "A randomised, phase II study of intetumumab, an anti-av-integrin mAb, alone and with dacarbazine in stage IV melanoma", (2011) British J Cancer 105: 346-352 (Year: 2011).*
Desgrosellier et al., "Integrins in Cancer: Biological Implications and Therapeutic Opportunities," Nat Rev Cancer 10(1):9-22 (2010).
Enns et al., "Alphavbeta5-integrins Mediate Early Steps of Metastasis Formation," Eur J Cancer 41(7):1065-1072 (2005).
Nair et al., "HYD1-induced Increase in Reactive Oxygen Species Leads to Autophagy and Necrotic Cell Death in Multiple Myeloma Cells," Mol Cancer Ther. 8(8):2441-2451 (2009).
PCT International Search Report and Written Opinion corresponding to PCT/US2016/029219, dated Nov. 18, 2016.
Guescini et al., "Astrocytes and Glioblastoma Cells Release Exosomes Carrying mtDNA," J Neural Transm 117 (1):1-4 (2010).
Balaj et al., "Tumour Microvesicles Contain Retrotransposon Elements and Amplified Oncogene Sequences," Nat Commun 2:180 (2011).
Zhang et al., "Stimulated Human Mast Cells Secrete Mitochondrial Components That Have Autocrine and Paracrine Inflammatory Actions," PLOS One 7(12):1-9 (2012).
Kahlert et al., "Identification of Double-Stranded Genomic DNA Spanning Chromosomes with Mutated KRAS and p53 DNA in the Serum Exosomes of Patients with Pancreatic Cancer," J. Biol. Chem. 289(7):3869-3875 (2014).
Thakur et al., "Double-Stranded DNA in Exosomes: a Novel Biomarker in Cancer Detection," Cell Res. 24(6):766-769 (2014).
Schmid et al, "EGFR/KRAS/BRAF Mutations in Primary Lung Adenocarcinomas and corresponding Locoregional Lymph Node Metastase," Clin Cancer Res. 15:4554 (2009).
Adamczyk et al, "Characterization of Soluble and Exosomal Forms of the EGFR Released from Pancreatic Cancer Cells," Life Sciences 89:304 (2011).
Batagov et al., "Exosomes Secreted by Human Cells Transport Largely mRNA Fragments that are Enriched in the 3'-Untranslated Regions," Biology Direct 8(12):1-8 (2013).
Fesler et al., "Circulating microRNA Testing for the Early Diagnosis and Follow-up of Colorectal Cancer Patients," Mol. Diagn. Ther. 18(3):303-308 (2014).
Mathivanan et al., "Exosomes: Extracellular Organelles Important in Intercellular Communication," J. Proteomics 73:1907-1920 (2010).
Zhang et al., "A Niche Role for Cancer Exosomes in Metastasis," Nat. Cell Biol. 17(6):709-711 (2015).
Seton-Rogers, "Metastasis: An Influential Delivery," Nat. Rev. Cancer 15(7):386 (2015).
Ferrarelli, "Exosomes Prep the Metastatic Site," Sci. Signal. 8(380):ec150 (2015).
Vignieri and Smith, "Cancer Biology: Tumor Cells Educate the Metastatic Niche," Science Magazine 348(6240):1220 (Jun. 12, 2015).
Ray, "Pancreatic Cancer Exosomes Prime the Liver for Metastasis," Nat. Rev. Gastroenterol. Hepatol. 12(7):371 (2015).
Costa-Silva et al., "Pancreatic Cancer Exosomes Initiate Pre-Metastatic Niche Formation in the Liver," Nat. Cell Biol. 17:816-826 (2015).
Hagemann et al., "Macrophages Induce Invasiveness of Epithelial Cancer Cells via NF-kappaB and JNK," J. Immunol. 175:1197-1205 (2005).

* cited by examiner

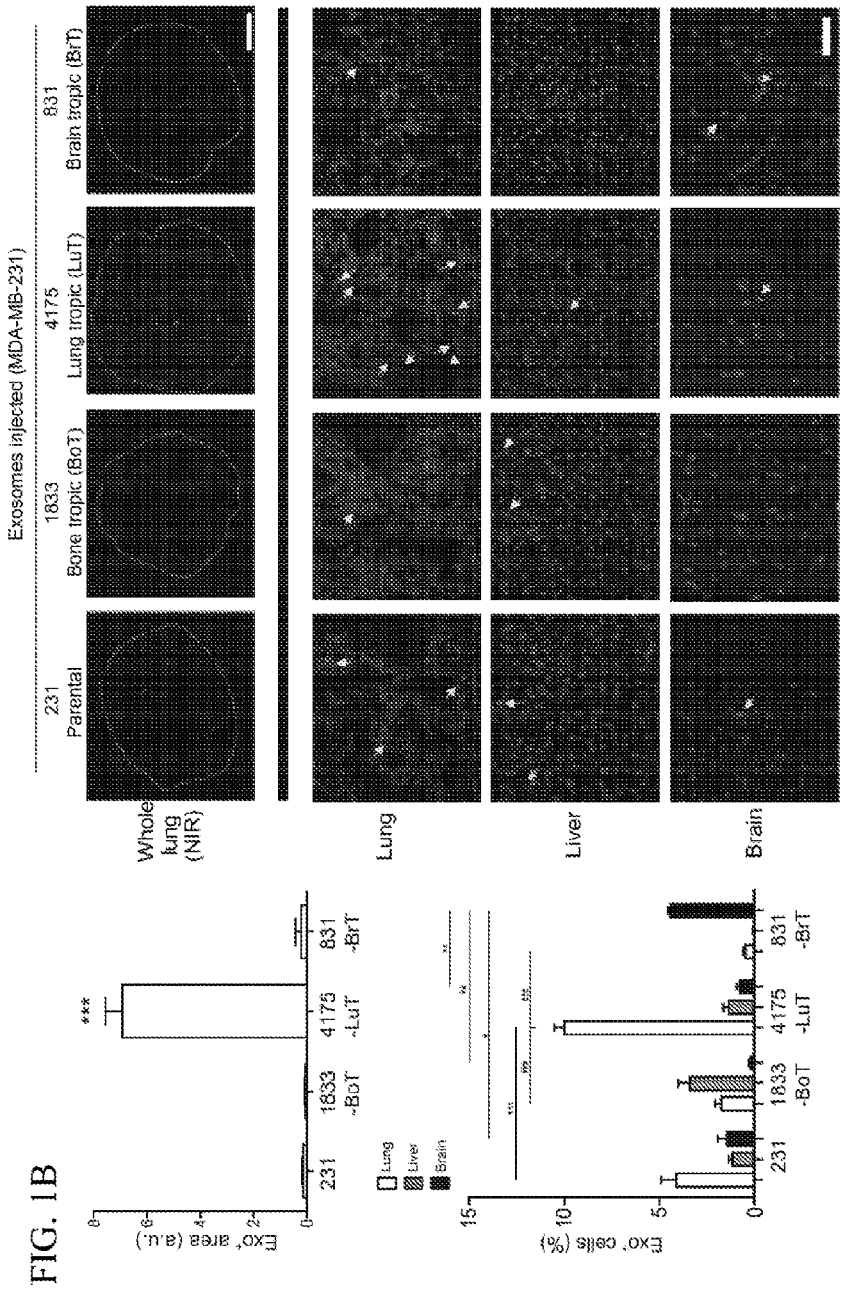
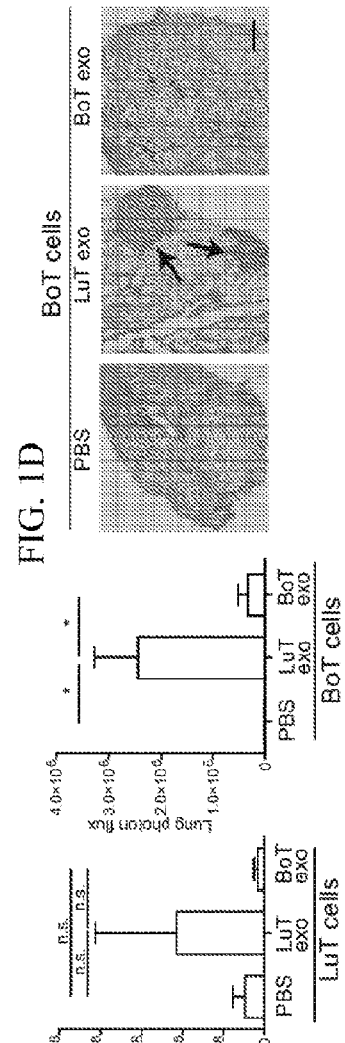
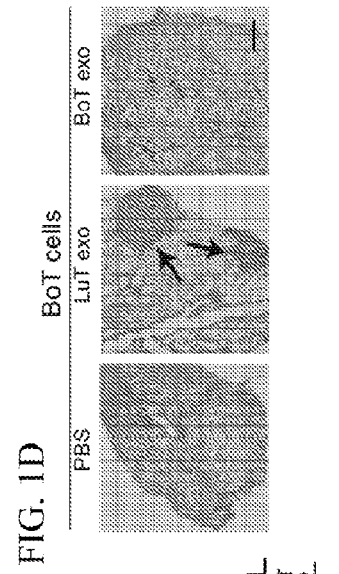
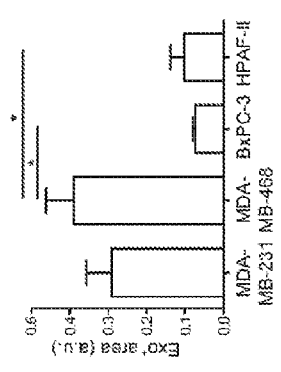
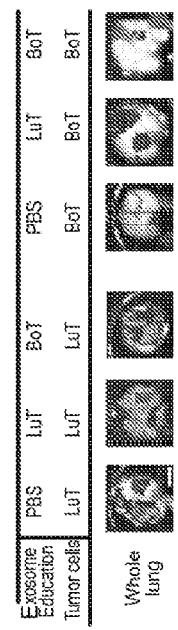
FIG. 1A
FIG. 1B
FIG. 1C
FIG. 1D FIG. 4A
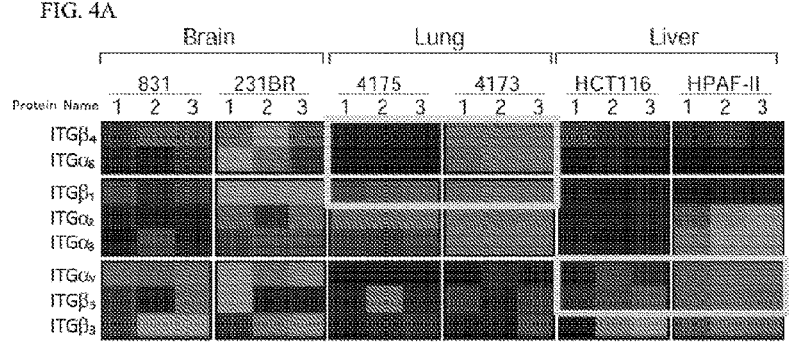
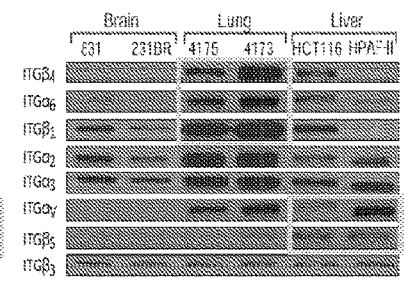
FIG. 4B
Z-scored LFQ Integrin signal: Low — High
FIG. 4C
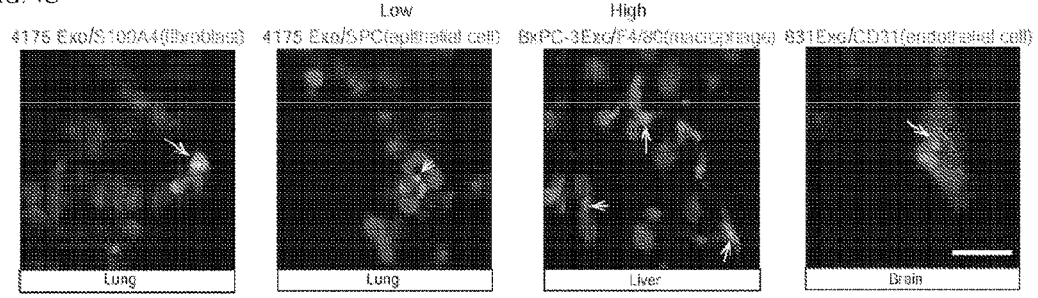

FIG. 5A
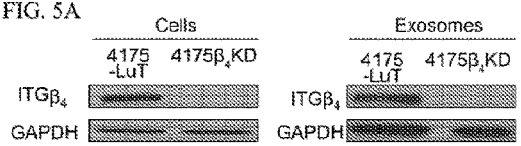
FIG. 5B
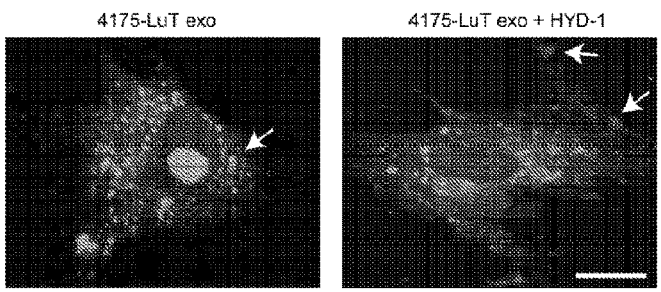
FIG. 5C
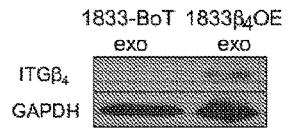
FIG. 5D
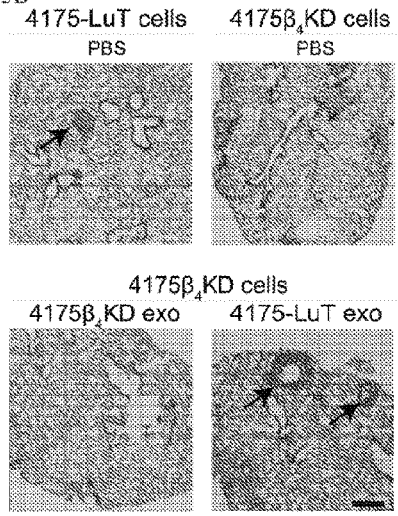
FIG. 5E
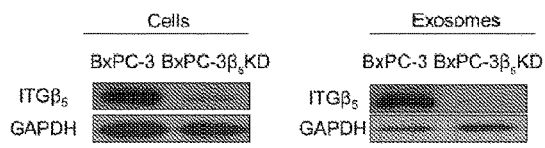
FIG. 5F
Exosome distribution
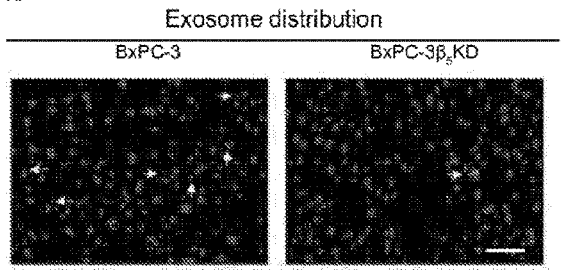
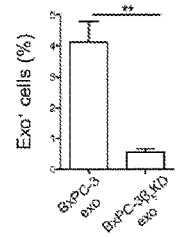
FIG. 5G
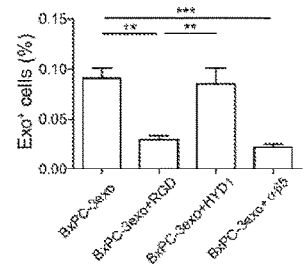

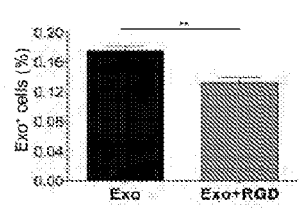
FIG. 5H
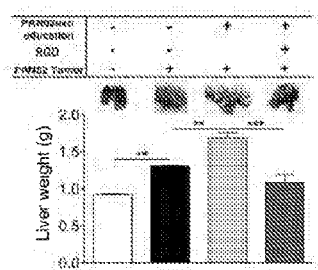
FIG. 5I
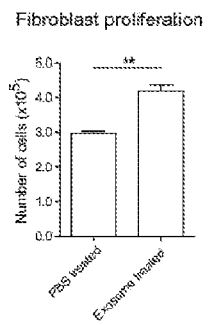
FIG. 5J
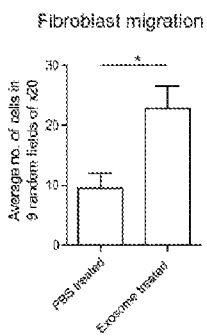
FIG. 5K
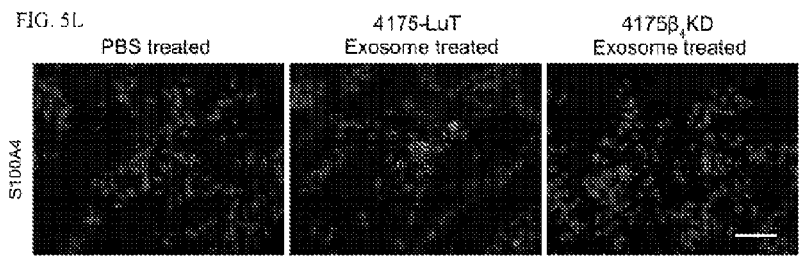
FIG. 5L
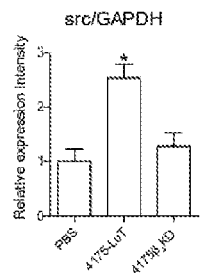
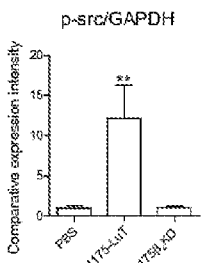
FIG. 5M

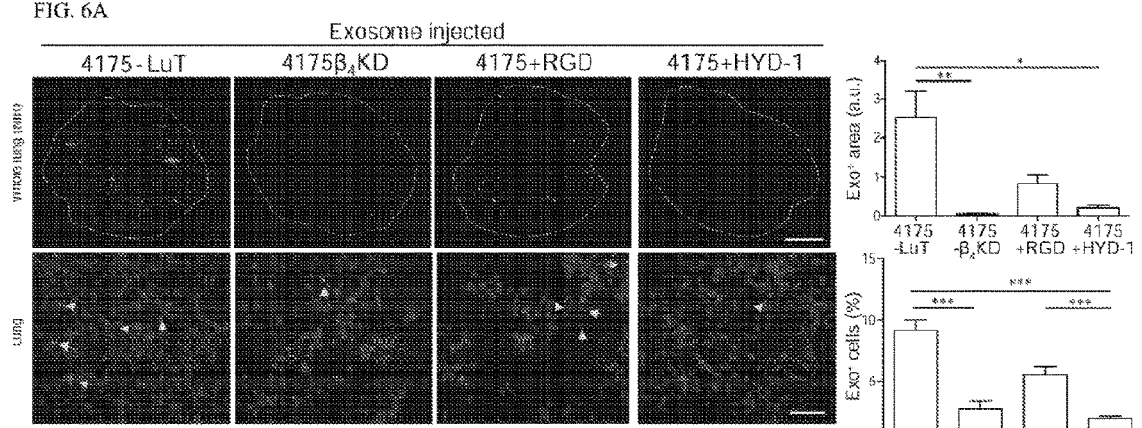
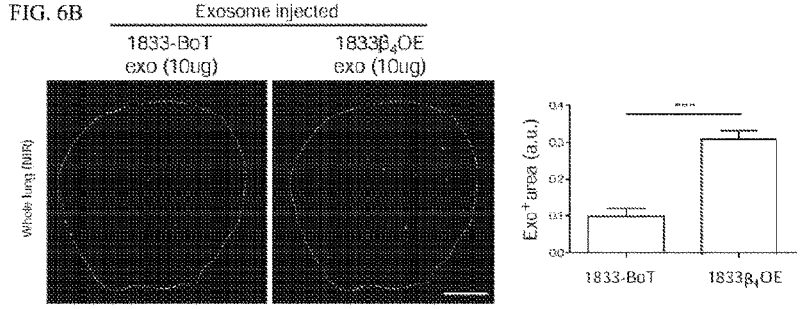
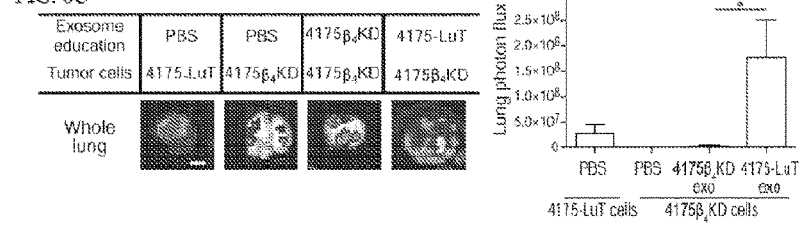
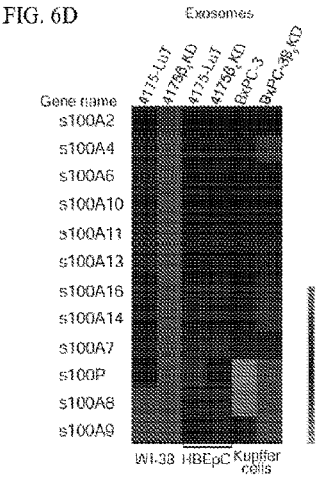
FIG. 6A
FIG. 6B
FIG. 6C
FIG. 6D

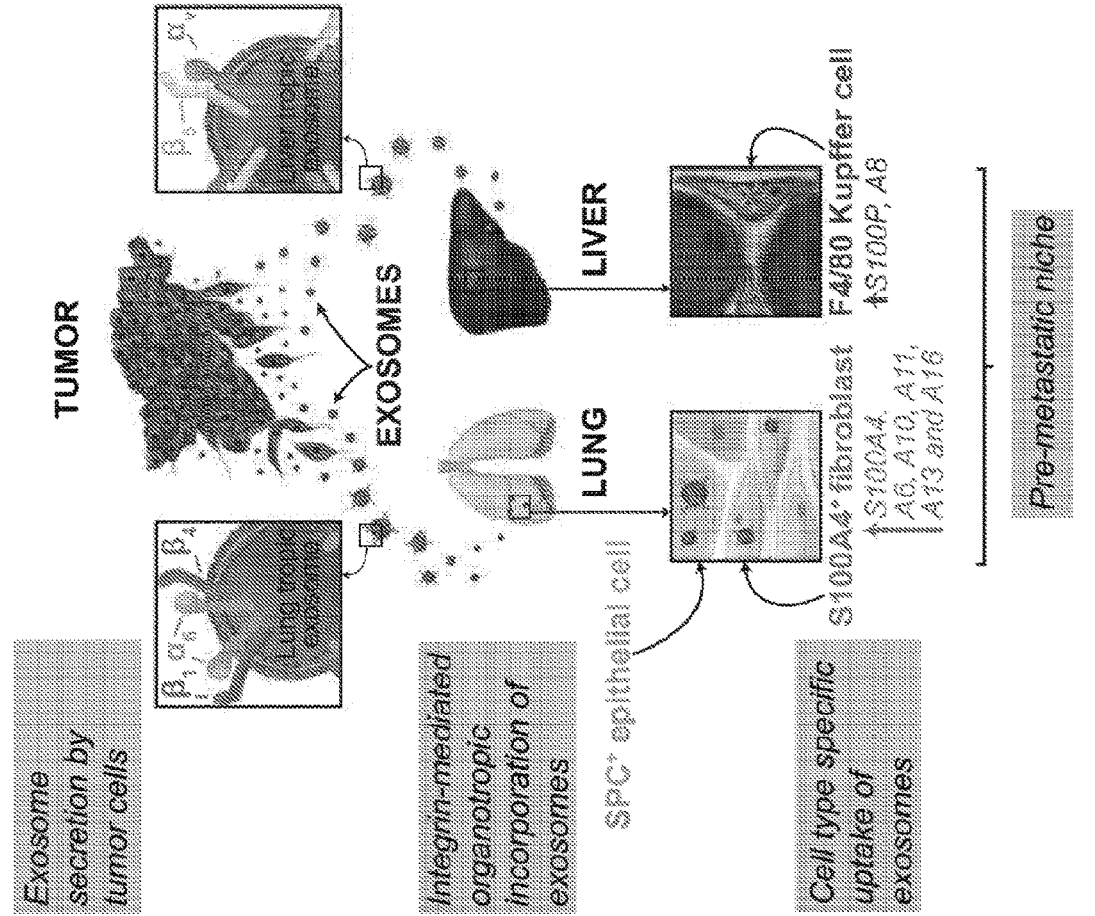
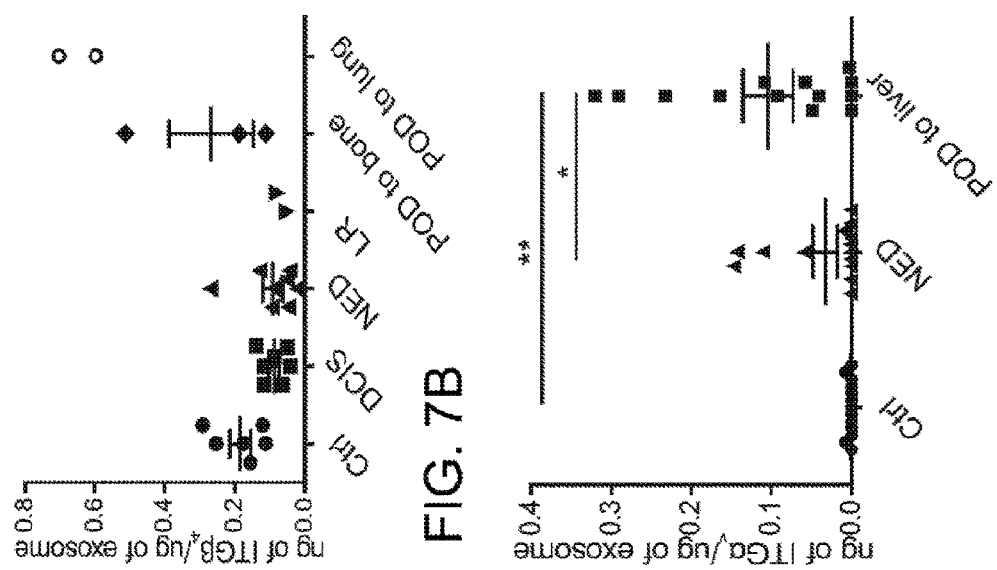

FIG. 8A
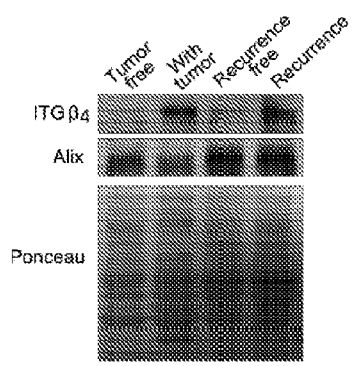
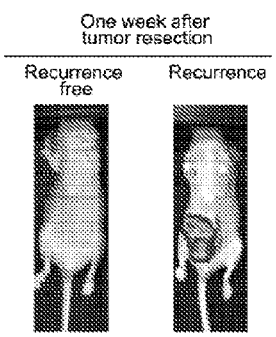
One week after tumor resection
FIG. 8B
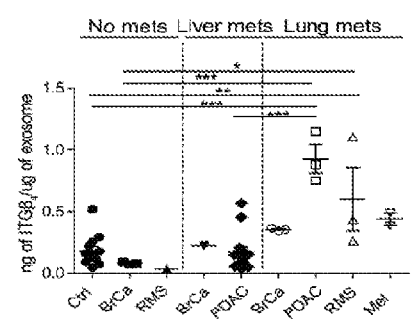
FIG. 8C
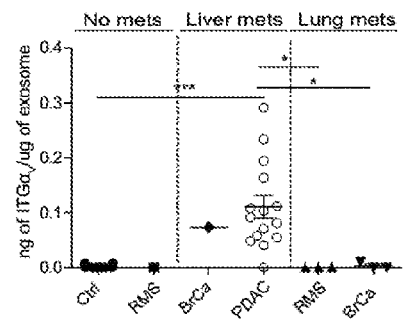

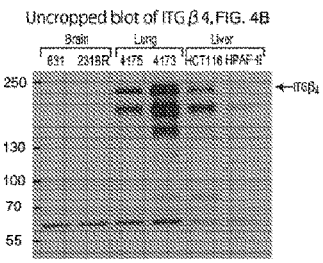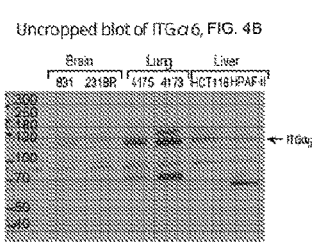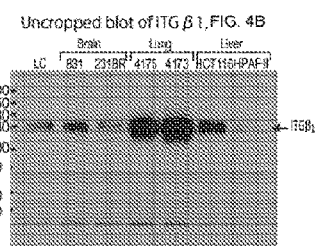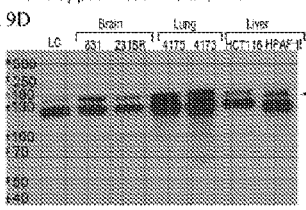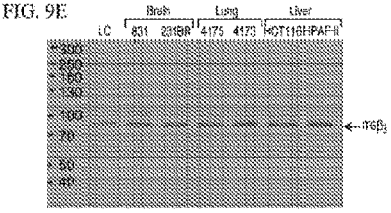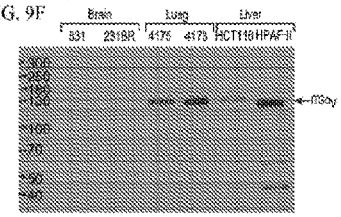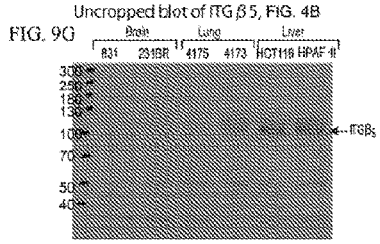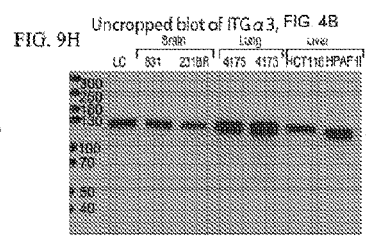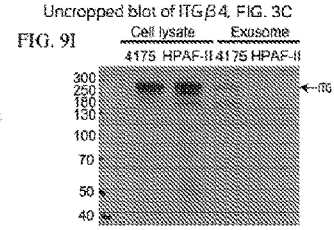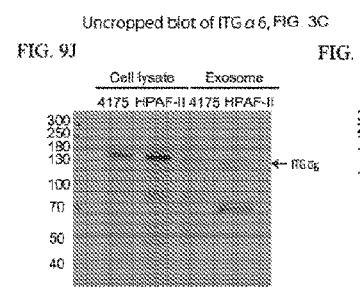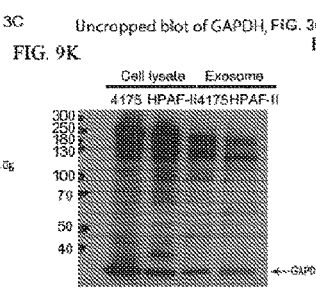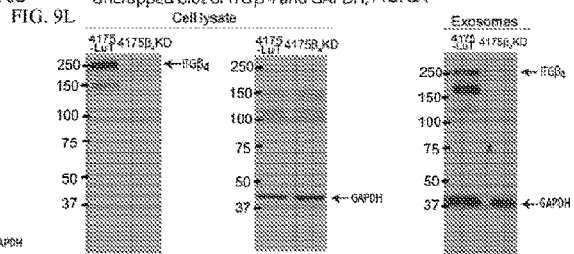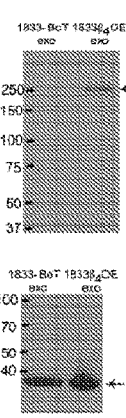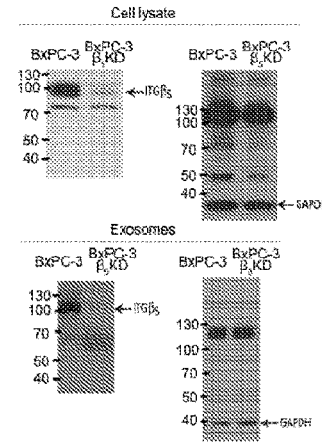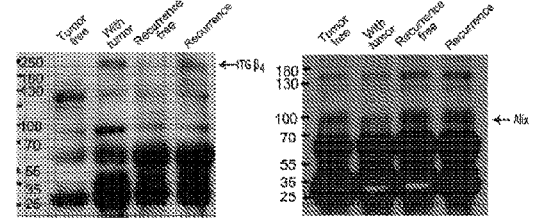

METHODS AND REAGENTS FOR DETERMINATION AND TREATMENT OF ORGANOTROPIC METASTASIS

This application is a national stage application under 35 U.S.C. § 371 of PCT Application No. PCT/US2016/029219, filed 25 Apr. 2016, which claims the priority benefit of U.S. Provisional Patent Application Ser. No. 62/152,615, filed 24 Apr. 2015, and 62/242,723, filed 16 Oct. 2015, which are hereby incorporated by reference in their entirety.

This invention was made with government support under grant numbers W81XWH-13-1-0427 awarded by the United States Department of Defense. The government has certain rights in this invention.

FIELD OF THE INVENTION

The present invention relates to methods and reagents for determination and treatment of organotropic metastasis.

BACKGROUND OF THE INVENTION

Despite Stephen Paget's 126-year-old "seed-and-soil" hypothesis (Paget, S., "The Distribution of secondary Growths in Cancer of the Breast," *Cancer Metastasis Rev* 8:98-101 (1989)), insufficient progress has been made towards decoding the mechanisms governing organ-specific metastasis. In experimental metastasis assays, Fidler et al. demonstrated that cancer cells derived from a certain metastatic site displayed enhanced abilities to metastasize to that specific organ, providing support for Paget's organ-specific metastasis theory (Hart et al., "Role of Organ Selectivity in the Determination of Metastatic Patterns of B16 Melanoma," *Cancer Res* 40:2281-2287 (1980)). Subsequent studies investigating organ-specific metastasis focused largely on the role of intrinsic cancer cell properties, such as genes and pathways regulating colonization, in directing organotropism (Muller et al., "Involvement of Chemokine Receptors in Breast Cancer Metastasis," *Nature* 410:50-56 (2001); Weilbaecher et al., "Cancer to Bone: A Fatal Attraction," *Nature reviews. Cancer* 11:411-425 (2011); Zhou et al., "Cancer-Secreted miR-105 Destroys Vascular Endothelial Barriers to Promote Metastasis," *Cancer Cell* 25:501-515 (2014); Chang et al., "The IL-6/JAK/Stat3 Feed-Forward Loop Drives Tumorigenesis and Metastasis," *Neoplasia* 15:848-862 (2013); Lu et al., "Organotropism of Breast Cancer Metastasis," *Journal of Mammary Gland Biology and Neoplasia* 12:153-162 (2007); Cox et al., "The Hypoxic Cancer Secretome Induces Pre-Metastatic Bone Lesions Through Lysyl Oxidase," *Nature* 522:106-110 (2015)). Breast cancer cells express chemokine receptors, such as C—X—C motif receptor (CXCR)-4 and C—C motif receptor (CCR)-7, which partner with chemokine ligands expressed in lymph nodes (CXCL12) and lung (CCL21), thus guiding metastasis (Muller et al., "Involvement of Chemokine Receptors in Breast Cancer Metastasis," *Nature* 410:50-56 (2001); Weilbaecher et al., "Cancer to Bone: A Fatal Attraction," *Nature Reviews Cancer* 11:411-425 (2011)). Tumour-secreted factors can also increase metastasis by inducing vascular leakiness (Zhou et al., "Cancer-Secreted miR-105 Destroys Vascular Endothelial Barriers to Promote Metastasis," *Cancer Cell* 25:501-515 (2014)), promoting the recruitment of pro-angiogenic immune cells (Chang et al., "The IL-6/JAK/Stat3 Feed-Forward Loop Drives Tumorigenesis and Metastasis," *Neoplasia* 15:848-862 (2013)), and influencing organotropism (Lu et al., "Organotropism of Breast Cancer Metastasis," *Journal of Mammary Gland Biology and Neoplasia* 12:153-162 (2007)). Furthermore, the ability of breast cancer to form osteolytic lesions depends on osteoclast-stimulating growth factors (e.g., PTHRP and GM-CSF) released into the bone microenvironment (Weilbaecher et al., "Cancer to Bone: A Fatal Attraction," *Nature Reviews Cancer* 11:411-425 (2011); Cox et al., "The Hypoxic Cancer Secretome Induces Pre-Metastatic Bone Lesions Through Lysyl Oxidase," *Nature* 522:106-110 (2015)). Therefore, the previous observation that metastatic melanoma-derived factors dictate organotropism is not surprising (Kaplan et al., "VEGFR1-Positive Haematopoietic Bone Marrow Progenitors Initiate the Pre-Metastatic Niche," *Nature* 438:820-827 (2005)). It was found that medium conditioned by highly metastatic B16-F10 melanoma cells was sufficient to expand the metastatic repertoire of Lewis lung carcinoma cells that would typically metastasize only to lung (Kaplan et al., "VEGFR1-Positive Haematopoietic Bone Marrow Progenitors Initiate the Pre-Metastatic Niche," *Nature* 438:820-827 (2005)). It was also shown that pre-metastatic niche formation requires S100 protein and fibronectin upregulation by lung resident cells and recruitment of bone marrow (BM)-derived myeloid cells in response to tumour-secreted factors (Kaplan et al., "VEGFR1-Positive Haematopoietic Bone Marrow Progenitors Initiate the Pre-Metastatic Niche," *Nature* 438:820-827 (2005)). These events establish a favourable microenvironment that promotes growth of disseminated tumour cells upon their arrival (Kaplan et al., "VEGFR1-Positive Haematopoietic Bone Marrow Progenitors Initiate the Pre-Metastatic Niche," *Nature* 438:820-827 (2005); Hiratsuka et al., "MMP9 Induction by Vascular Endothelial Growth Factor Receptor-1 is Involved in Lung-Specific Metastasis," *Cancer Cell* 2:289-300 (2002); Peinado et al., "Melanoma Exosomes Educate Bone Marrow Progenitor Cells Toward a Pro-Metastatic Phenotype Through MET," *Nat Med* 18:883-891 (2012)).

Recently, it was demonstrated that exosomes are one of the tumour-derived factors inducing vascular leakiness, inflammation, and BM progenitor cell recruitment during pre-metastatic niche formation and metastasis (Peinado et al., "Melanoma Exosomes Educate Bone Marrow Progenitor Cells Toward a Pro-Metastatic Phenotype Through MET," *Nat Med* 18:883-891 (2012)). Exosomes are small membrane vesicles (30-100 nm) containing functional biomolecules (i.e., proteins, lipids, RNAs, DNA) that can be horizontally transferred to recipient cells (Balaj et al., "Tumour Microvesicles Contain Retrotransposon Elements and Amplified Oncogene Sequences," *Nat Commun* 2:180 (2011); Skog et al., "Glioblastoma Microvesicles Transport RNA and Proteins that Promote Tumour Growth and Provide Diagnostic Biomarkers," *Nat Cell Biol* 10:1470-1476 (2008); Thery et al., "Membrane Vesicles as Conveyors of Immune Responses," *Nat Rev Immunol* 9:581-593 (2009); Raposo et al., "Extracellular Vesicles: Exosomes, Microvesicles, and Friends," *J Cell Biol* 200:373-383 (2013); Peinado et al., "The Secreted Factors Responsible for Pre-Metastatic Niche Formation: Old Sayings and New Thoughts," *Semin Cancer Biol* 21:139-146 (2011); Choi et al., "Proteomics, Transcriptomics and Lipidomics of Exosomes and Ectosomes," *Proteomics* 13:1554-1571 (2013); Valadi et al., "Exosome-Mediated Transfer of mRNAs and microRNAs is a Novel Mechanism of Genetic Exchange Between Cells," *Nat Cell Biol* 9:654-659 (2007); Thakur et al., "Double-Stranded DNA in Exosomes: A Novel Biomarker in Cancer Detection," *Cell Res* 24:766-769 (2014)). It was shown that an "exosomal protein signature" could identify melanoma patients at risk for metastasis to non-specific distant sites (Peinado et al., "Melanoma Exosomes Educate Bone Marrow Progenitor Cells Toward a Pro-Metastatic Phenotype Through MET," *Nat Med* 18:883-891 (2012)). Moreover, in the context of pancreatic cancer exosomes, the sequential steps involved in liver pre-metastatic niche induction were defined (Costa-Silva et al., "Pancreatic Cancer Exosomes Initiate Pre-Metastatic Niche Formation in the Liver," *Nat Cell Biol* (2015)). However, a deeper analysis of these processes is essential to understand the molecular basis of organ-specific metastasis as well as for the development of potential therapeutics.

The present invention is directed to overcoming these and other deficiencies in the art.

SUMMARY OF THE INVENTION

A first aspect of the present invention relates to a method of prognosing cancer in a subject. This method involves selecting a subject having cancer and obtaining, from the selected subject, a sample containing exosomes. The exosomes are then contacted with one or more reagents suitable to detect higher or lower levels or the presence or absence of one or more integrins on said exosomes, and the cancer is prognosed based on the contacting step.

Another aspect of the present invention relates to a method of treating a subject having cancer. This method involves selecting a subject having cancer characterized by a particular exosomal integrin profile and administering to the selected subject a therapeutic integrin inhibitor corresponding to the exosomal integrin profile.

Another aspect of the present invention relates to a method of managing treatment of a subject having cancer. This method involves selecting a subject undergoing treatment for cancer and obtaining, from the selected subject, a sample containing exosomes. Higher or lower levels or the presence or absence of one or more integrins expressed on the exosomes is detected, and treatment is modified, as necessary, based on the detecting step.

Another aspect of the present invention relates to a kit suitable for determining whether a cancer is likely to metastasize to the brain. This kit includes one or more reagents suitable for detecting the expression levels of $ITG\alpha_v$ and $ITG\beta_3$.

Another aspect of the present invention relates to a kit suitable for determining whether a cancer is likely to metastasize to the lung. This kit includes one or more reagents suitable for detecting the expression levels of $ITG\alpha_6$, $ITG\beta_1$, and $ITG\beta_4$.

Another aspect of the present invention relates to a kit suitable for determining whether a cancer is likely to metastasize to the liver. This kit includes one or more reagents suitable for detecting the expression levels of $ITG\alpha_v$ and $ITG\beta_5$.

Another aspect of the present invention relates to a method of prognosing cancer in a subject. This method involves selecting a subject having cancer and obtaining, from the selected subject, a tissue sample. The tissue is then contacted with one or more reagents suitable to detect higher or lower levels or the presence or absence of one or more S100 molecules in said tissue, and the cancer is prognosed based on the contacting step.

Another aspect of the present invention relates to a method of treating a subject having cancer. This method involves selecting a subject having cancer characterized by a particular tissue S100 profile and administering to the selected subject a therapeutic S100 inhibitor corresponding to the tissue S100 profile.

Another aspect of the present invention relates to a method of managing treatment of a subject having cancer. This method involves selecting a subject undergoing treatment for cancer and obtaining, from the selected subject, a sample containing S100 molecules. Higher or lower levels or the presence or absence of one or more S100 molecules expressed in the sample is detected, and treatment is modified, as necessary, based on the detecting step.

Another aspect of the present invention relates to a kit suitable for determining whether a cancer is likely to metastasize to the lung. This kit includes one or more reagents suitable for detecting the expression levels of S100A4, S100A6, S100A10, S100A11, S100A13, and S100A16.

Another aspect of the present invention relates to a kit suitable for determining whether a cancer is likely to metastasize to the liver. This kit includes one or more reagents suitable for detecting the expression levels of S100A8, S100A9, and S100P.

The present study is an investigation of whether molecules present on tumour-derived exosomes 'address' them to specific organs, where they can induce pre-metastatic niche formation. To test this idea, multiple tumour models (osteosarcoma, rhabdomyosarcoma, Wilm's tumour, skin and uveal melanoma, breast, colorectal, pancreatic and gastric cancer) were used, all of which have a propensity to metastasize to specific sites (i.e., brain, lung or liver). The biodistribution of tumour-secreted exosomes was subsequently analyzed, and it was found that exosomal integrins direct organ-specific colonization by fusing with target cells in a tissue-specific fashion, thereby initiating pre-metastatic niche formation. Remarkably, it was found that tumour-secreted exosomes can redirect metastasis of tumour cells that normally lack the capacity to metastasize to a specific organ. Finally, clinical data indicate that integrin expression profiles of circulating plasma exosomes isolated from cancer patients could be used as prognostic factors to predict sites of future metastasis.

Therefore, the present invention is based on the inventors' discovery that circulating tumor exosomes express specific integrins involved in metastasis to specific organ sites. Accordingly, tumor derived exosomal integrin expression can serve as a non-invasive, diagnostic and prognostic tool by facilitating the rapid identification of metastatic sites to enable early detection and/or prevention of metastasis and optimized treatment of disease. Importantly, diagnoses and prognoses are rendered feasible using this technique in cases where a biopsy is difficult to obtain (due to inaccessibility). Moreover, this tool allows for frequent monitoring of the dynamics of tumor progression and molecular changes during treatment. In addition to prognostic and diagnostic utility, the molecular information gathered from exosomal integrin analysis can be used to guide and develop personalized therapeutic regimes. Finally, because exosomes are secreted from tumors constitutively, and isolation of exosomes requires no special equipment, exosome integrin expression-based testing can be readily employed in all standard laboratories.

Thus, the present invention makes significant progress in decoding the mechanisms governing organ-specific metastasis, while also establishing useful prognostic biomarkers, and identifying potentially truly effective anti-metastatic therapeutic agents. By investigating the exosomal integrin profile, which is distinct from the integrin profile of the parent tumor, the present invention advances existing prognostic tools in cancer and, consequently, improves stratification of cancer patients in terms of disease stage and risk of metastasis.

BRIEF DESCRIPTION OF THE DRAWINGS

FIGS. 1A-D show cancer cell-derived exosomes localize to and dictate future metastatic organs. FIG. 1A shows the biodistribution of human cancer cell line-derived exosomes in lung and liver of naïve mice. The upper graph is a quantification of exosome-positive areas by NIR imaging of whole lung in arbitrary units, a.u. (n=3 per group). Error bars, ±s.e.m. *P<0.05 by one-way ANOVA. The lower graph is immunofluorescence quantification of exosome-positive cells (n=3, 3 independent experiments). Error bars, ±s.e.m. *P<0.05, P<0.01 by one-way ANOVA. FIG. 1B shows MDA-MB-231 (parental), 1833-BoT, 4175-LuT and 831-BrT-derived exosome biodistribution. The left upper graph shows quantification of exosome-positive areas by NIR imaging of whole lung in arbitrary units, a.u. (n=3 for all, except 831-BrT, where n=4). Error bars, ±s.e.m. *P<0.001 by one-way ANOVA. The right upper panels show NIR whole lung imaging. Scale bar, 5 mm. The left lower graph shows immunofluorescence quantification of exosome-positive cells (n=5 animals pooled from 2 independent experiments). Error bars, ±s.e.m. *P<0.05; P<0.01; *P<0.001 by one-way ANOVA. The right lower panels show fluorescence microscopy of lung, liver, and brain. Arrows indicate exosome foci. Scale bar, 50 µm. FIG. 1C shows redirection of metastasis by education with organotropic exosomes. 4175-LuT or 1833-BoT cell metastasis in the lung after treatment with PBS, 4175-LuT, or 1833-BoT exosomes is shown. The left panels show quantitative bioluminescence of metastatic lesions. Scale bar, 5 mm. The right graph shows quantification of luciferase activity (n=5 for all, except for LuT exo/LuT cells, where n=4, data representative of 2 independent experiments). Error bars, ±s.e.m. *P<0.05 by one-way ANOVA. FIG. 1D shows lung hematoxylin/eosin staining from FIG. 1C. Arrows indicate lung metastasis. Scale bar is 500 µm.

FIG. 2A shows human cancer exosome biodistribution in lung and liver. Ten micrograms of exosomes derived from each cell line were labelled with lipophilic PKH26 dye and injected retro-orbitally into nude mice 24 hours before sacrifice. The upper panels show representative NIR whole lung image by Odyssey imaging (n=3). Scale bar, 5 mm. Middle and lower panels represent exosome biodistribution in the lung and liver as determined by immunofluorescence microscopy. Arrows indicate exosome foci (n=3, 3 independent experiments). Scale bar, 50 µm. FIG. 2B shows biodistribution of exosomes isolated from murine cell lines E0771 and Pan02. Murine exosome biodistribution in the lung and liver was determined by immunofluorescence microscopy. Ten micrograms of exosomes derived from each cell line were labelled with lipophilic PKH26 dye and injected retro-orbitally into nude mice 24 hours before sacrifice. The upper panel shows lung at 40× magnification. The lower panel shows liver at 40× magnification. Arrows indicate exosome foci. Scale bar, 50 µm. Graph represents the quantification of exosome distribution by counting exosome-positive cells. An average of five random fields per sample were counted at 20× magnification (3 independent experiments, each with n=3). Error bars, ±s.e.m. P<0.01 by two-tailed Student's t-test. FIG. 2C shows analysis of organotropic cell-derived exosomes. MDA-MB-231 organotropic cell line-derived exosomes were analyzed for size distribution by NanoSight and phenotype (purity and shape) by electron microscopy; black arrows indicate representative exosomes. Scale bar, 100 nm. FIG. 2D shows flow cytometric analysis of exosome$^+$ cells in lung. Ten micrograms of exosomes derived from MDA-MB-231 organotropic cell lines were labelled with lipophilic PKH67 dye and injected retro-orbitally into nude mice 24 hours before sacrifice. FITC channel positive cells were acquired on a FACS Calibur and the percentage of exosome positive cells was quantified (representing data pooled from 2 independent experiments, a total of n=12). Error bars, ±s.e.m. P<0.01 by one-way ANOVA. FIG. 2E shows flow cytometric analysis of exosome positive cells in the bone marrow. Ten micrograms of exosomes derived from MDA-MB-231 organotropic cell lines were labelled with lipophilic PKH67 dye and injected retro-orbitally into nude mice 24 hours before sacrifice. FITC channel positive cells were acquired on a FACS Calibur and the percentage of exosome positive cells was quantified (representing data pooled from 2 independent experiments, a total of n=6). Error bars, ±s.e.m. **P<0.01 and *P<0.05 by one-way ANOVA for the 831-BrT to 1833-Bo-T and 4175-LuT comparisons, respectively. FIG. 2F shows electron microscopy imaging of FM1-43-labelled 4175-LuT exosomes. Scale bar, 100 nm. Gray arrows indicate FM1-43 positive exogenous tumor-derived exosomes, and black arrows indicate endogenous exosomes. FIG. 2G shows representative NIR imaging of lung whole mount upon daily exosome injections. Ten micrograms of exosomes derived from 4175-LuT cells were injected daily for three consecutive days via the retro-orbital sinus and the whole lung was imaged by Odyssey imaging. Scale bar, 5 mm (n=4). FIG. 2H shows representative hematoxylin/eosin staining of the lung from FIG. 1C at 20× magnification. Arrows indicate lung metastasis and scale bar, 500 FIG. 2I shows analysis of 1833-BoT cell metastasis to the lung, after three weeks of continuous treatment with PBS or 4175-LuT exosomes, followed by intra-cardiac injection of 1×10$^5$ tumour cells. Mice were injected retro-orbitally with exosomes every other day for three weeks, prior to tumour cell injection. Quantitative bioluminescence imaging of luciferase activity by IVIS imaging is shown. Scale bar, 5 mm. Metastasis was quantified three weeks post tumour cell injection (n=4). Error bars, ±s.e.m. ***P<0.001 by two-tailed Student's t-test.

FIG. 3A shows top 40 adhesion molecules packaged in exosomes isolated from organ tropic cell lines. A heat map of adhesion molecule signals based on Z-scored LFQ values obtained from quantitative mass spectrometry analysis is shown. PEP (posterior error probability), MS/MS count is a number of fragmentation spectra (spectral counting), Razor+ unique peptides refers to the number of peptides, and sequence coverage refers to percentage of peptide counts identified. FIG. 3B shows Ponceau staining of exosome lysates isolated from organ tropic cell lines. Representative Ponceau staining of total protein from the organ tropic cell line-derived exosomes is shown. Ten micrograms of exosomal protein were loaded in each well (n=2, 3 independent experiments). FIG. 3C shows western blot analysis comparison of ITGα$_6$ and ITGβ$_4$ levels in cell lysates versus exosomes derived from organotropic breast cancer and pancreatic cancer cell lines. For western blot source data, see FIG. 9I-K. FIG. 3D shows quantification of organtropic exosome uptake by target cells in vivo. The upper graph shows flow cytometric quantification of the frequency of 4175-LuT exosome-positive fibroblasts and epithelial cells (n=4). The left lower graph shows flow cytometric quantification of the frequency of BxPC-3 exosome-positive macrophages (n=3). The right lower graph shows quantification of the frequency of 831-BrT exosome positive endothelial cells by immunofluorescence microscopy (n=5). Error bars, ±s.e.m. FIG. 3E shows organotropic cell line-derived exosomes induce vascular leakiness in the lung. Leakiness in the lung 24 hours after retro-orbital injection of ten micrograms of MDA-MB-231 organotropic cell line-derived exosomes was quantified by imaging the presence of fluorescent dextran outside of blood vessels, in the lung parenchyma. The left upper panel shows 40× magnification of representative lung image following PBS injection. The left lower panel shows representative lung image following 4175-LuT exosome injection. Scale bar, 50 µm. The right graph depicts the quantification of five random areas at 20× magnification in arbitrary units, a.u. (data representative of 2 independent experiments n=3). Error bars, ±s.e.m; *P<0.05, **P<0.01 by one-way ANOVA. FIG. 3F shows immunofluorescence analysis of resident cells in lung, liver, and brain following exosome-labelled injection. Analysis of exosome co-staining with markers for tissue specific stromal cell types. The top panels show representative images of immunofluorescence microscopy of 4175-LuT exosome co-staining with F4/80, CD31, and EpCAM. However, there was no co-localization of these markers. The middle panels show liver sections from mice injected with BxPC-3-derived exosomes were co-stained with CD31, S100A4, and EpCAM. However, there was no co-localization of these markers. The lower panels show brain sections from mice injected with 831-BrT exosome were co-stained with F4/80, S100A4, and EpCAM. However, there was no co-localization of these markers. Scale bar, 30 µm; (n=3 per experiment for 2 independent experiments). FIG. 3G shows exosome biodistribution and co-localization with extracellular matrix proteins. The left upper panels show representative immunofluorescence microscopy images of lung tissue, depicting 4175-LuT exosome co-staining with laminin. The right upper panels show laminin co-staining with S100A4. The left lower panels shows representative immunofluorescence microscopy of liver tissue co-stained for fibronectin and BxPC-3 exosomes. The right lower panels show fibronectin co-staining with F4/80; (n=3, 2 independent experiments); scale bar, 30 µm.

FIGS. 4A-C show organ-specific tumour exosomes interact with resident cells. FIG. 4A shows a heat map of integrin signals from quantitative mass spectrometry analysis, based on Z-scored LFQ values (technical triplicates). FIG. 4B shows western blot analysis of integrins from organotropic cell line-derived exosomes, representative of three independent experiments. For western blot source data, see FIG. 9A-H. FIG. 4C shows analysis by immunofluorescence of exosome distribution and different resident cell types. Shown left to right: lung co-staining with S100A4 (fibroblasts), SPC (epithelial cells) and 4175-LuT exosomes, liver co-staining with F4/80 (macrophages) and BxPC-3 exosomes, and brain co-staining with CD31 (endothelial cells) and 831-BrT exosomes. Scale bar, 30 µm.

FIGS. 5A-M show ITGs functionally regulate organotropic exosome uptake and exosome-mediated metastasis. FIG. 5A shows representative western blot analysis of integrin expression in 4175-LuT and 4175β4KD cells and exosomes; (representative of three independent experiments). For western blot source data, see FIG. 9L. FIG. 5B shows in vitro uptake of 4175-LuT exosomes by WI-38 lung fibroblasts. The WI-38 cell membrane was labelled with PKH67 dye and 4175-LuT exosomes were labelled with PKH26 dye. 10 µg/ml of exosomes were first incubated with PBS or HYD-1 peptide for 30 minutes at 37° C., followed by one hour incubation with WI-38 cells at 37° C. Excess exosomes were washed and cells were imaged (n=4 for two independent experiments); scale bar, 10 µm. FIG. 5C shows representative western blot of ITGβ$_4$ expression in exosomes isolated from WT or ITGβ$_4$-overexpressing 1833-BoT cells (representative of two independent experiments). For western blot source data, see FIG. 9M. FIG. 5D shows representative hematoxylin/eosin staining of lungs from FIG. 6C. Arrows indicate lung metastasis. Scale bar, 500 µm. FIG. 5E shows representative western blot analysis of integrin expression in BxPC-3 and BxPC-3β5KD cells and exosomes. For western blot source data, see FIG. 9N. FIG. 5F shows immunofluorescence analysis of BxPC-3 control and BxPC-3β$_5$KD-derived exosome biodistribution in the liver. Ten micrograms of exosomes isolated from each cell line were labelled with lipophilic PKH26 dye and injected retro-orbitally into nude mice 24 hours before sacrifice. The left panel shows 40× magnification. Arrows indicate exosome foci. Scale bar, 50 µm. The right graph shows quantification of exosome distribution by exosome+ cells. An average of five random fields were counted at 20× magnification (data representative of 2 independent experiment n=3). Error bars, ±s.e.m. P<0.01 (two-tailed Student's t-test). FIG. 5G shows flow cytometry analysis of exosome positive cells in the liver 24 hours after exosome injection. Five micrograms of labelled BxPC-3 exosomes per mouse were incubated with PBS, RGD, HYD-1, or ITGαvβ$_5$ antibody for 30 minutes at 37° C. prior to retro-orbital injection into nude mice. Livers were harvested and analyzed for exosome positive cells by flow cytometry 24 hours post injection (n=4, except for the ITGαvβ$_5$ antibody group, which n=5). Error bars, ±s.e.m. P<0.01, *P<0.001 by one-way ANOVA. FIG. 5H shows microscopic analysis of exosome-positive cells in the livers of mice injected with liver metastatic Pan02-derived exosomes. Prior to injection, Pan02 exosomes were pre-incubated with RGD peptide for 30 minutes at 37° C. Ten micrograms of Pan02 exosomes were labelled with lipophilic PKH67 dye and injected retro-orbitally into C57BL/6 mice 24 hours before sacrifice. Livers were digested and exosome-positive cells were quantified by flow cytometry (n=3). Error bars, ±s.e.m. P<0.01 (two-tailed Student's t-test). FIG. 6I shows analysis of Pan02 liver metastasis after three weeks of continuous treatment with PBS, Pan02-derived exosomes, or Pan02-derived exosomes pre-incubated with RGD peptide for 30 minutes at 37° C. Pan02 cells were injected intra-splenically. Mice were injected retro-orbitally with five micrograms of exosome every other day for three weeks. The upper panels show representative liver images showing metastasis taken at sacrifice. The lower panels show liver weight quantification (n=4 except for the control and peptide group for which n=3 of one experiment). Error bars, ±s.e.m; P<0.01, * P<0.001 by one-way ANOVA. FIG. 5J shows functional analysis of lung fibroblasts educated with 4175-LuT-derived exosomes. Proliferation of lung fibroblasts educated with exosomes every other day for two weeks is shown. Three days after cells were plated at equal density, cell numbers were counted using a hemocytometer (n=3 in 3 independent experiments). Error bars, ±s.e.m. **P<0.01. FIG. 5K shows migration of lung fibroblasts educated with exosomes every other day for two weeks was measured as follows. Fibroblasts were plated in 24 well transwell chamber inserts and after six hours the number of cells migrated was counted using hematoxylin staining. Nine random fields were counted at 20× magnification and the average number of cells per field was calculated (total of n=4 from two independent experiments). Error bars, ±s.e.m. *P<0.05. FIG. 5L shows representative image of the lung stained for S100A4. Mice were every other day with PBS, 4175-LuT, or 4175β$_4$KD exosomes for three weeks. Scale bar, 50 µm.

FIG. 5M shows in situ (in-cell western) protein expression analysis of WI-38 fibroblasts treated with PBS, 4175-LuT, or 4175ITGβ$_4$KD exosomes. Relative expression levels of Src and p-Src (n=3, 3 independent experiments) is shown. Error bars, ±s.e.m. **P<0.01 and *P<0.05 by one-way ANOVA.

FIGS. 6A-D show exosomal ITGβ$_4$ expression functionally contributes to 4175-LuT localization and mediates lung metastasis. FIG. 6A, left upper panels, show NIR whole lung imaging of 4175-LuT, 4175β$_4$KD or 4175-LuT-derived exosomes pre-incubated with RGD or HYD-1 peptides. Scale bar, 5 mm. The right upper graph shows quantification of exosome-positive areas in arbitrary units, a.u. (n=4, except 4175 for which n=6). Error bars, ± s.e.m. *P<0.05; P<0.01 by one-way ANOVA. The left lower panels show fluorescence microscopy. Arrows indicate exosome foci. Scale bar, 50 μm. The lower right graph shows immunofluorescence quantification of exosome-positive cells (n=6 pooled from 2 independent experiments). Error bars, ±s.e.m. *P<0.001 by one-way ANOVA. FIG. 6B, left panel, show NIR whole lung imaging of 1833-BoT (n=5) or 1833-BoT overexpressing (OE) ITGβ$_4$ (n=4) exosomes. Scale bar, 5 mm. The right graph shows quantification of exosome-positive areas in arbitrary units, a.u. Error bars, ±s.e.m. ***P<0.001 by two-tailed Student's t-test. FIG. 6C shows experimental lung metastasis of 4175ITGβ$_4$KD cells after education with WT or 4175ITGβ$_4$KD exosomes. Bioluminescence imaging of lung metastasis and quantification of luciferase activity (n=6, data representative of 2 independent experiments) is shown. Scale bar, 5 mm. Error bars, ±s.e.m. *P<0.05 by one-way ANOVA. FIG. 6D shows a heat map of S100 gene expression fold change by qRT-PCR in 4175-LuT or 4175ITGβ$_4$KD exosome-conditioned lung fibroblast (WI-38) or epithelial (HBEpC) cells and liver tropic BxPC-3 or BXPC-3 ITGβ$_5$KD exosome-conditioned Kupffer cells.

FIGS. 7A-C show exosomal integrin expression as a potential predictor of patient organ metastasis. FIG. 7A shows exosomal ITGβ$_4$ levels in breast cancer patients who were metastasis-free at the time of blood draw. Amount of ITGβ$_4$ per microgram of exosome in healthy control subjects (n=6); patients with DCIS (n=7), invasive breast cancer without relapse in three years (n=8), locoregional recurrence within three years (n=2), bone metastasis within three years (n=3), or lung metastasis within three years (n=2) is shown. FIG. 7B shows exosomal ITGα$_v$ in pancreatic cancer patients metastasis-free at the time of blood draw. Amount of ITGα$_v$ per microgram of exosome in healthy control subjects (n=13); patients with pancreatic cancer without relapse within three years (n=14), or liver metastasis within three years (n=13) is shown. Error bars, ±s.e.m. *P<0.05; **P<0.01 by one-way ANOVA. FIG. 7C shows a model of exosome-mediated organotropic tumour dissemination. Tumor-derived exosomes are uptaken by organ-specific resident cells in future metastatic organs based on integrin expression.

FIGS. 8A-C show exosomal integrin expression as a potential metastatic site biomarker. FIG. 8A shows exosomal ITGβ$_4$ levels in the plasma of mice bearing orthotopic 4175-Lu-T tumors, as a function of tumor progression. Blood plasma was collected for exosome isolation six weeks post-intra-mammary fat pad tumor injection, then again one week post tumor resection, from mice who were deemed to be either free of tumor or presenting with recurring tumors based on IVIS bioluminescence imaging (n=5 were pooled for each group, based on one experiment). For western blot source data, see FIG. 9O. FIG. 8B shows exosomal ITGβ$_4$ in healthy control subjects (n=13); patients with breast cancer and no metastasis (n=3), liver metastasis (n=1), or lung metastasis (n=3); patients with rhabdomyosarcoma and no metastasis (n=1) or lung metastasis (n=3); patients with pancreatic cancer with liver metastasis (n=14) and lung metastasis (n=3); and patients with melanoma with lung metastasis (n=2). Error bars, ± s.e.m. *P<0.05, P<0.01, *P<0.001 by one-way ANOVA. FIG. 8C shows exosomal ITGα$_v$ in healthy control subjects (n=13); patients with rhabdomyosarcoma and no metastasis (n=1) or lung metastasis (n=3); patients with breast cancer and lung metastasis (n=3) or liver metastasis (n=1); and patients with pancreatic cancer and liver metastasis (n=15). Error bars, ±s.e.m. *P<0.05; ***P<0.001 by one-way ANOVA.

FIGS. 9A-0 show the western blot source data for FIGS. 3C, 4B, 5A, 5C, 5E, and 8A. FIG. 9A shows the uncropped western blot of ITGβ$_4$ from FIG. 4B. FIG. 9B shows the uncropped western blot of ITGα$_6$ from FIG. 4B. FIG. 9C shows the uncropped western blot of ITGβ$_1$ from FIG. 4B. FIG. 9D shows the uncropped western blot of ITGα$_2$ from FIG. 4B. FIG. 9E shows the uncropped western blot of ITGβ$_3$ from FIG. 4B. FIG. 9F shows the uncropped western blot of ITGα$_v$ from FIG. 4B. FIG. 9G shows the uncropped western blot of ITGβ$_5$ from FIG. 4B. FIG. 9H shows the uncropped western blot of ITGα$_3$ from FIG. 4B. FIG. 9I shows the uncropped western blot of ITGβ$_4$ from FIG. 3C. FIG. 9J shows the uncropped western blot of ITGα$_6$ from FIG. 3C. FIG. 9K shows the uncropped western blot of GAPDH from FIG. 3C. FIG. 9L shows the uncropped western blot of ITGβ$_4$ and GAPDH from FIG. 5A. FIG. 9M shows the uncropped western blot of ITGβ$_4$ and GAPDH from FIG. 5C. FIG. 9N shows the uncropped western blot of ITGβ$_5$ and GAPDH from FIG. 5E. FIG. 9O shows the uncropped western blot of ITGβ$_4$ and Alix from FIG. 8A.

DETAILED DESCRIPTION OF THE INVENTION

Figure 2A:
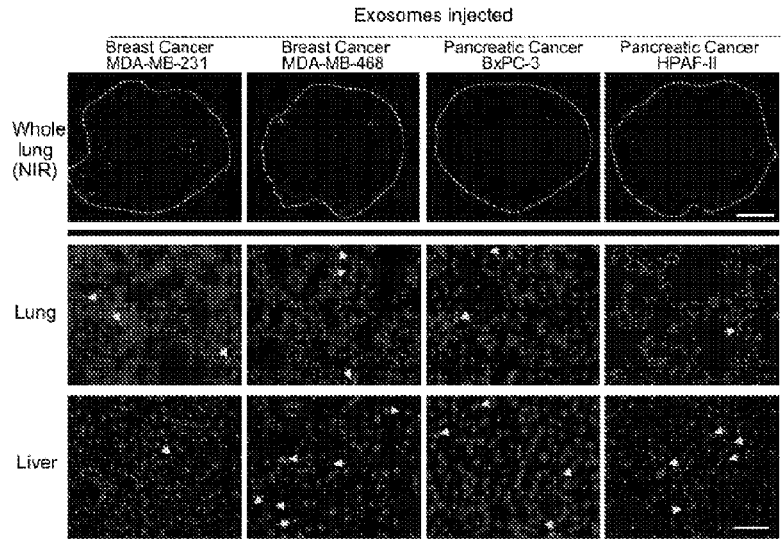
FIGS. 2A-I show characterization of organotropic exosome properties and biodistribution.

A first aspect of the present invention relates to a method of prognosing cancer in a subject. This method involves selecting a subject having cancer and obtaining, from the selected subject, a sample containing exosomes. The exosomes are then contacted with one or more reagents suitable to detect higher or lower levels or the presence or absence of one or more integrins on said exosomes, and the cancer is prognosed based on the contacting step.

Cancer prognosis as described herein includes determining the probable progression and course of the cancerous condition, and determining the chances of recovery and survival of a subject with the cancer, e.g., a favorable prognosis indicates an increased probability of recovery and/or survival for the cancer patient, while an unfavorable prognosis indicates a decreased probability of recovery and/or survival for the cancer patient. A subject's prognosis can be determined by the availability of a suitable treatment (i.e., a treatment that will increase the probability of recovery and survival of the subject with cancer). Accordingly, this aspect of the present invention may further include selecting a suitable cancer therapeutic based on the determined prognosis and administering the selected therapeutic to the subject.

Prognosis also encompasses the metastatic potential of a cancer. For example, a favorable prognosis based on higher or lower levels or the presence or absence of a phenotype can indicate that the cancer is a type of cancer having low metastatic potential, and the patient has an increased probability of long term recovery and/or survival. Alternatively, an unfavorable prognosis, based on higher or lower levels or the presence or absence of a phenotype can indicate that the cancer is a type of cancer having a high metastatic potential, and the patient has a decreased probability of long term recovery and/or survival.

Prognosis further encompasses prediction of sites of metastasis, determination of the stage of the cancer, or prediction of the metastatic potential of the cancer.

In accordance with all aspects of the present invention, a "subject" or "patient" encompasses any animal, but preferably a mammal, e.g., human, non-human primate, a dog, a cat, a horse, a cow, or a rodent. More preferably, the subject or patient is a human. In some embodiments of the present invention, the subject has cancer, for example and without limitation, melanoma, breast cancer, or lung cancer. In some embodiments, the cancer is a primary tumor, while in other embodiments, the cancer is a secondary or metastatic tumor.

Another aspect of the present invention relates to a method of treating a subject having cancer. This method involves selecting a subject having cancer characterized by a particular exosomal integrin profile and administering to the selected subject a therapeutic integrin inhibitor corresponding to the exosomal integrin profile.

In one embodiment, the subject is selected based upon determining the exosomal integrin profile of the selected subject.

"Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

In accordance with the methods of the present invention, exosomes can be isolated or obtained from most biological fluids including, without limitation, blood, serum, plasma, ascites, cyst fluid, pleural fluid, peritoneal fluid, cerebral spinal fluid, tears, urine, saliva, sputum, nipple aspirates, lymph fluid, fluid of the respiratory, intestinal, and genitourinary trances, breast milk, intra-organ system fluid, or combinations thereof.

An enriched population of exosomes can be obtained from a biological sample using methods known in the art. For example, exosomes may be concentrated or isolated from a biological sample using size exclusion chromatography, density gradient centrifugation, differential centrifugation (Raposo et al. "B lymphocytes Secrete Antigen-presenting Vesicles," *J Exp Med* 183(3): 1161-72 (1996), which is hereby incorporated by reference in its entirety), anion exchange and/or gel permeation chromatography (for example, as described in U.S. Pat. No. 6,899,863 to Dhellin et al., and U.S. Pat. No. 6,812,023 to Lamparski et al., which are hereby incorporated by reference in their entirety), sucrose density gradients or organelle electrophoresis (for example, as described in U.S. Pat. No. 7,198,923), magnetic activated cell sorting (MACS) (Taylor et al., "MicroRNA Signatures of Tumor-derived Exosomes as Diagnostic Biomarkers of Ovarian Cancer," *Gynecol Oncol* 110(1): 13-21 (2008), which is hereby incorporated by reference in its entirety), nanomembrane ultrafiltration (Cheruvanky et al., "Rapid Isolation of Urinary Exosomal Biomarkers using a Nanomembrane Ultrafiltration Concentrator," *Am J Physiol Renal Physiol* 292(5): F1657-61 (2007), which is hereby incorporated by reference in its entirety), immunoabsorbent capture, affinity purification, microfluidic separation, or combinations thereof.

Exosomes isolated from a bodily fluid (i.e., peripheral blood, cerebrospinal fluid, urine) can be enriched for those originating from a specific cell type, for example, lung, pancreas, stomach, intestine, bladder, kidney, ovary, testis, skin, colorectal, breast, prostate, brain, esophagus, liver, placenta, and fetal cells. Because the exosomes often carry surface molecules from their donor cells, surface molecules may be used to identify, isolate and/or enrich for exosomes from a specific donor cell type. In this way, exosomes originating from distinct cell populations can be analyzed for their protein content. For example, tumor (malignant and non-malignant) exosomes carry tumor-associated surface molecules and these exosomes can be isolated and/or enriched via these specific tumor-associated surface molecules. In one example, the tumor-associated surface molecule is epithelial-cell-adhesion-molecule (EpCAM), which is specific to exosomes from carcinomas of lung, colorectal, breast, prostate, head and neck, and hepatic origin, but not of hematological cell origin (Balzar et al. "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety). In another example, the surface molecule is CD24, which is a glycoprotein specific to urine microvesicles (Keller et al. "CD24 is a Marker of Exosomes Secreted into Urine and Amniotic Fluid," *Kidney Int* 72(9): 1095-102 (2007), which is hereby incorporated by reference in its entirety). In yet another example, the surface molecule is CD70, carcinoembryonic antigen (CEA), EGFR, EGFRvIII and other variants, Fas ligand, TRAIL, transferrin receptor, p38.5, p97 and HSP72. Alternatively, tumor specific exosomes may be characterized by the lack of surface markers, such as the lack of CD80 and CD86 expression.

In one embodiment, the tumor exosomes are separated from normal exosomes by analysis of the expression of $ITG\alpha_2$, $ITG\alpha_3$, and $ITG\beta_1$ as shown herein.

The isolation of exosomes from specific cell types can be accomplished, for example, by using antibodies, aptamers, aptamer analogs, or molecularly imprinted polymers specific for a desired surface molecule. In one embodiment, the surface molecule is specific for a cancer type. In another embodiment, the surface molecule is specific for a cell type which is not necessarily cancerous. One example of a method of exosome separation based on cell surface molecule is provided in U.S. Pat. No. 7,198,923, which is hereby incorporated by reference in its entirety. As described in, e.g., U.S. Pat. No. 5,840,867 to Toole and U.S. Pat. No. 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes.

In accordance with this aspect and other aspects of the invention, the exosomes are then contacted with one or more reagents suitable to detect higher or lower levels or the presence or absence of one or more integrins in the exosome sample.

In one embodiment, the one or more integrins are selected from the group consisting of $ITG\alpha_1$, $ITG\alpha_2$, $ITG\alpha_{2b}$, $ITG\alpha_3$, $ITG\alpha_4$, $ITG\alpha_5$, $ITG\alpha_6$, $ITG\alpha_{11}$, $ITG\alpha_v$, $ITG\beta_1$, $ITG\beta_3$, $ITG\beta_4$, $ITG\beta_5$, and $ITG\beta_6$.

In accordance with this aspect of the present invention, and as described herein, exosomes derived from tumors having high metastatic potential to specific organ sites contain much higher levels of certain integrins within the exosome sample than exosomes derived from tumors having a low or no metastatic potential to those same organs. Further, exosomes derived from tumors express high levels of $ITG\beta_1$ as well as $ITG\alpha_1$, $ITG\alpha_2$, $ITG\alpha_{2b}$, $ITG\alpha_3$, $ITG\alpha_4$, $ITG\alpha_5$, $ITG\alpha_6$, $ITG\alpha_{11}$, $ITG\alpha_v$, $ITG\beta_3$, $ITG\beta_4$, $ITG\beta_5$, and $ITG\beta_6$, when compared to normal exosomes, which express low to no $ITG\beta_1$ and no $ITG\alpha_1$, $ITG\alpha_2$, $ITG\alpha_{2b}$, $ITG\alpha_3$, $ITG\alpha_4$, $ITG\alpha_5$, $ITG\alpha_6$, $ITG\alpha_{11}$, $ITG\alpha_v$, $ITG\beta_3$, $ITG\beta_4$, $ITG\beta_5$, and $ITG\beta_6$.

The exosomal expression levels of the one or more markers of metastatic disease is compared to a "control" expression level of the same one or more markers to identify a subject as one that is at risk for metastatic disease. In one embodiment, the control expression level of a marker is the average expression level of the marker in exosomal samples taken from a cohort of healthy individuals (i.e., the average expression level in non-cancerous exosomal samples). In another embodiment, the control expression level is the average expression level of the marker in exosomal samples taken from individuals having a primary tumor, e.g., a gastrointestinal tumor, that never metastasized to the liver or other organ of the body. In another embodiment, the control expression level of a marker is the expression level of the marker in an exosomal sample taken from the subject being tested, but at an earlier time point (e.g., a pre-cancerous time point). In all of these embodiments, an increased expression level of the one or more markers of metastatic disease in the sample from the subject relative to the control exosomal expression level identifies the subject as having or at risk of developing metastatic disease.

An "increased expression level" refers to an expression level (i.e., protein or gene expression level) that is higher than the control level. For example, an increased expression level is at least 50% higher than the control expression level.

In another embodiment, the control expression level of a marker is the average expression level of the marker in exosomal samples taken from individuals having a primary tumor, e.g., a gastrointestinal tumor, that later metastasized. Alternatively, the control expression level of a marker is the average expression level of the marker in exosomal samples taken from individuals with metastatic disease. In accordance with this embodiment, when the exosomal expression level of a marker in the subject being tested is the same as the control expression level, the subject is identified as having or at risk of developing metastatic disease.

As described herein, exosomal integrins also have a functional role in upregulating pro-migratory and pro-inflammatory S100 molecules in target cells in a Src-dependent manner, influencing the expression of genes implicated in tumour metastasis. Specifically, S100A8, S100A9, and S100P are upregulated in the liver in response to liver-tropic tumor exosomes, and S100A4, S100A6, S100A10, S100A11, S100A13, and S100A16 are upregulated in the lung in response to lung-tropic tumor exosomes.

Accordingly, in another embodiment, the measured expression levels of one or more markers of pre-metastatic niche formation, such as S100 molecules, are compared to expression levels of the one or more markers of pre-metastatic niche formation in a control sample and the subject is identified as having or at risk of developing metastases when the subject has increased expression levels of the one or more markers of pre-metastatic niche formation relative to control expression levels of the one or more markers of pre-metastatic niche formation.

The one or more markers of pre-metastatic niche formation can be measured independently or in combination with the one or more exosomal markers of metastatic disease as described supra to identify a subject having or at risk of developing metastases.

In one embodiment of the present invention, the method is carried out to determine whether the cancer is likely to metastasize to the brain by detecting higher or lower levels or the presence or absence of $ITG\alpha_v$ and/or $ITG\beta_3$. Accordingly, where metastasis to the brain is determined to be likely, $ITG\alpha_v$ and $ITG\beta_3$ inhibitors may be administered to the subject.

In another embodiment, the method is carried out to determine whether the cancer is likely to metastasize to the lung by detecting higher or lower levels or the presence or absence of $ITG\alpha_6$, $ITG\beta_1$, and/or $ITG\beta_4$. Accordingly, where metastasis to the lung is determined to be likely, $ITG\alpha_6$, $ITG\beta_1$, and/or $ITG\beta_4$ inhibitors may be administered to the subject.

In a further embodiment, the method is carried out to determine whether the cancer is likely to metastasize to the liver by detecting higher or lower levels or the presence or absence of $ITG\alpha_v$ and/or $ITG\beta_5$. Accordingly, where metastasis to the liver is determined to be likely, $ITG\alpha_v$ and $ITG\beta_5$ inhibitors may be administered to the subject.

In another embodiment, the method is carried out to determine whether the cancer is likely to occur, recur, or metastasize by detecting higher or lower levels or the presence or absence of $ITG\alpha_2$, $ITG\alpha_3$, and $ITG\beta_1$. Accordingly, where occurrence, recurrence, or metastasis is determined to be likely, $ITG\alpha_2$, $ITG\alpha_3$, and $ITG\beta_1$ inhibitors may be administered to the subject.

The integrin inhibitors of the present invention may be any integrin inhibitor. In one embodiment, the inhibitor is an antibody, a peptide, peptidomimetic, or a small molecule.

Exemplary integrin inhibitors that may be used in the methods of the present invention include, but are not limited to, abciximab, etaracizumab, abegrin, CNTO95, cilengitide, eptifibatide, ATN-161, vipegitide, MK0429, E7820, Vitaxin, 5247, PSK1404, S137, and HYD-1.

In accordance with the methods of the present invention, administering one or more integrin inhibitors to treat or prevent metastasis to specific organ sites can be done concurrently with other therapeutic approaches, i.e., the inhibitor is administered as part of a combination therapy. Accordingly, in one embodiment of the present invention, the agent is administered in combination with one or more additional inhibitors of metastatic disease progression, such as, a chemotherapeutic, radiation (e.g., external beam radiation therapy or brachytherapy), anti-angiogenic therapeutic, a premetastatic niche formation inhibitor, a stromal inhibitor, a bone-marrow derived cell inhibitor, a myeloid derived suppressor cell inhibitor, and extracellular matrix protein inhibitors.

Suitable chemotherapeutic agents for combination therapies include, without limitation, alkylating agents (e.g., chlorambucil, cyclophosphamide, CCNU, melphalan, procarbazine, thiotepa, BCNU, and busulfan), antimetabolites (e.g., methotraxate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic or anti-vasculogenic therapeutics suitable for use in combination with an exosome inhibitor of the invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer? A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR, Kit, Flt3, Tet and CSF1R), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin avβ3 antibody).

Suitable stromal inhibitors for use in the present invention are known in the art (see Bissell et al., "Why Don't We Get More Cancer? A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

Suitable premetastatic niche formation inhibitors includes, without limitation, bone-marrow derived cell inhibitors (e.g., VEGFR1 inhibitor or CD11b inhibitor), S100A8 inhibitor, S100A9 inhibitors, Lysyl oxidase inhibitor, matrix metalloproteinase-9 and -2 inhibitors (e.g., Incyclinide, PCK3145).

Suitable extracellular matrix protein inhibitors include, without limitation, DX2400, an MMP-14 inhibitor; PEGPH20, a covalently modified form of hyaluronidase which catalyzes the degradation of the extracellular matrix component hyalurona.

Other agents suitable for use in a combination therapy comprising the exosome inhibitors of the present invention are disclosed in Bissell et al., "Why Don't We Get More Cancer? A Proposed Role of the Microenvironment in Restraining Cancer Progression," *Nat. Med.* 17(3):320-329 (2011), which is hereby incorporated by reference in its entirety.

In an alternative embodiment of the present invention, the agent is administered as a part of an adjuvant therapy regime. In particular, this involves chemotherapy, hormone therapy, radiation therapy, immunotherapy, or a targeted therapy together with an agent that inhibits one or more integrins prior to and/or after surgery. In addition, the present invention may be used to treat patients after primary surgery who may not otherwise receive treatment, i.e. those patients with primary complete resection without evidence of residual or distant disease in order to prevent premetastatic niche formation and, therefore, metastatic spread.

Pharmaceutical compositions containing integrin inhibitors suitable for use in the methods of the present invention can include a pharmaceutically acceptable carrier as described infra, one or more active agents, and a suitable delivery vehicle. Suitable delivery vehicles include, but are not limited to, viruses, bacteria, biodegradable microspheres, microparticles, nanoparticles, liposomes, collagen minipellets, and cochleates.

In one embodiment of the present invention, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010), WO2011/034798 to Bumcrot et al., WO2009/111658 to Bumcrot et al., and WO2010/105209 to Bumcrot et al., which are hereby incorporated by reference in their entirety.

In another embodiment of the present invention, the delivery vehicle is a nanoparticle. A variety of nanoparticle delivery vehicles are known in the art and are suitable for delivery of an inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly (ethylene glycol) Copolymers As Novel Gene Carriers," *J. Control Release* 105(3):367-80 (2005) and Park et al., "Intratumoral Administration of Anti-KITENIN shRNA- Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment of the present invention, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda, and U.S. Pat. No. 5,059,421 to Loughrey et al., which are hereby incorporated by reference in their entirety.

A liposome which containing an integrin inhibitor can be contacted with the target primary cancer cells under conditions effective for delivery of the inhibitory agent into the cancer cell. For administration to a primary tumor site, the liposomal vesicles need not be targeted to the cancer cells per se. However, when it is desirable to inhibit exosome activity, the liposome is designed to target exosomes in circulation (e.g., using an exosome specific antibody).

The liposome and nanoparticle delivery systems can be made to accumulate at a target organ, tissue, or cell via active targeting (e.g., by incorporating an antibody or other ligand on the surface of the delivery vehicle). For example, when the target cell is a cancer cell as in the present invention, delivery vehicle may be conjugated to an anti-C3B(I) antibody as disclosed by U.S. Pat. No. 6,572,856 to Taylor et al., which is hereby incorporated by reference in its entirety. Alternatively, the delivery vehicle may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, which are hereby incorporated by reference in their entirety.

In another embodiment of the present invention, the delivery vehicle is a viral vector. Viral vectors are particularly suitable for the delivery of inhibitory nucleic acid molecules, such as siRNA or shRNA molecules, but can also be used to deliver molecules encoding an anti-integrin antibody. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988), Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Regardless of the type of infective transformation system employed, it should be targeted for delivery of the nucleic acid to the desired cell type. For example, for delivery into a cluster of cells (e.g., cancer cells) a high titer of the infective transformation system can be injected directly within the site of those cells so as to enhance the likelihood of cell infection. The infected cells will then express the inhibitory nucleic acid molecule targeting the inhibition of integrin expression. The expression system can further contain a promoter to control or regulate the strength and specificity of expression of the nucleic acid molecule in the target tissue or cell.

In practicing the methods of the present invention, the administering step is carried out to achieve inhibition of metastasis or metastatic disease progression. Such administration can be carried out systemically or via direct or local administration to the tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent (e.g., an antibody or an inhibitory nucleic acid molecule) and the disease to be treated.

The inhibitors of the present invention may be orally administered, for example, with an inert diluent, or with an assimilable edible carrier, or it may be enclosed in hard or soft shell capsules, or it may be compressed into tablets, or they may be incorporated directly with the food of the diet. Inhibitors of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the integrin inhibitors of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the inhibitors of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

In addition to the formulations described previously, the inhibitors may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt Effective doses of the compositions of the present invention, for the treatment of a metastatic disease vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

In accordance with this aspect and other aspects of the invention relating to detecting higher or lower levels or the presence or absence of one or more integrins in the sample, suitable methods for detecting integrins include, but are not limited to, measuring RNA expression level and measuring protein expression levels. These methods are commonly used in the art. For measuring protein expression levels, this method generally involve contacting the sample with one or more detectable reagents that is suitable for measuring protein expression, e.g., a labeled antibody or a primary antibody used in conjunction with a secondary antibody, and measuring protein expression level based on the level of detectable reagent in the sample after normalizing to total protein in the sample. Suitable methods for detecting protein expression level in an exosome sample that are commonly employed in the art include, for example and without limitation, western blot, immunoprecipitation, enzyme-linked immunosorbent assay (ELISA), radioimmunoassay (RIA), or fluorescent activated cell sorting (FACS). The measured protein expression level in the sample is compared to the protein expression level measured in a reference exosomal sample and the type of metastatic disease is identified based on this comparison.

Measuring gene expression by quantifying mRNA expression can be achieved using any commonly used method known in the art including northern blotting and in situ hybridization (Parker et al., "mRNA: Detection by in Situ and Northern Hybridization," *Methods in Molecular Biology*

106:247-283 (1999), which is hereby incorporated by reference in its entirety); RNAse protection assay (Hod et al., "A Simplified Ribonuclease Protection Assay," *Biotechniques* 13:852-854 (1992), which is hereby incorporated by reference in its entirety); reverse transcription polymerase chain reaction (RT-PCR) (Weis et al., "Detection of Rare mRNAs via Quantitative RT-PCR," *Trends in Genetics* 8:263-264 (1992), which is hereby incorporated by reference in its entirety); and serial analysis of gene expression (SAGE) (Velculescu et al., "Serial Analysis of Gene Expression," *Science* 270:484-487 (1995); and Velculescu et al., "Characterization of the Yeast Transcriptome," *Cell* 88:243-51 (1997), which is hereby incorporated by reference in its entirety).

Another aspect of the present invention relates to a method of managing treatment of a subject having cancer. This method involves selecting a subject undergoing treatment for cancer and obtaining, from the selected subject, a sample containing exosomes. Higher or lower levels or the presence or absence of one or more integrins expressed on the exosomes is then detected, and treatment is modified, as necessary, based the detecting step.

Methods for obtaining exosome samples and detecting higher or lower levels or the presence or absence of one or more integrins on the exosomes are described above.

In one embodiment, the detecting is carried out by comparing the expression of one or more integrins in the sample to that obtained in a prior sample from the selected subject. The time between obtaining a first exosomal sample and a second, or any additional subsequent exosomal samples from a subject can be any desired period of time, for example, weeks, months, years, as determined is suitable by a physician and based on the characteristics of the primary tumor (tumor type, stage, location, etc.). In one embodiment of this aspect of the present invention, the first sample is obtained before treatment and the second sample is obtained after treatment. Alternatively, both samples can be obtained after one or more treatments; the second sample obtained at some point in time later than the first sample. The expression of one or more integrins in the sample can also be compared to that of a standard.

In one embodiment, detection of $ITG\alpha_v$ and/or $ITG\beta_3$ indicates that the treatment should be modified, as necessary, to treat or prevent brain metastasis.

In another embodiment, detection of $ITG\alpha_6$, $ITG\beta_1$, and/or $ITG\beta_4$ indicates that the treatment should be modified, as necessary, to treat or prevent lung metastasis.

In a further embodiment, detection of $ITG\alpha_v$ and/or $ITG\beta_5$ indicates that the treatment should be modified, as necessary, to treat or prevent liver metastasis.

In another embodiment, detection of $ITG\alpha_2$, $ITG\alpha_3$, and/or $ITG\beta_1$ indicates that the treatment should be modified, as necessary, to treat or prevent cancer recurrence or metastasis.

One aspect of the present invention is directed to a kit suitable for determining whether a cancer is likely to metastasize to the brain. This kit includes one or more reagents suitable for detecting the expression levels of $ITG\alpha_v$ and $ITG\beta_3$.

A further aspect of the present invention is directed to a kit suitable for determining whether a cancer is likely to metastasize to the lung. This kit includes one or more reagents suitable for detecting the expression levels of $ITG\alpha_6$, $ITG\beta_1$, and $ITG\beta_4$.

A final aspect of the present invention is directed to a kit suitable for determining whether a cancer is likely to metastasize to the liver. This kit includes one or more reagents suitable for detecting the expression levels of $ITG\alpha_v$ and $ITG\beta_5$.

In accordance with the above kits of the present invention, all of the reagents suitable for detecting the expression levels of the described integrins may be combined into one kit.

In one embodiment, the kits contain one or more reagents suitable for isolating cancer exosomes. An exemplary reagent includes, but is not limited to, a reagent suitable for detecting the expression level of $ITG\beta_1$, $ITG\alpha_3$, $ITG\alpha_3$, Calreticulin (CALR), Coagulation factor V, Nidogen-1 (NID1), and Fibrinogen-like protein 1 on exosomes.

In another embodiment, the kits contain one or more reagents suitable for isolating all exosomes. Exemplary reagents include, but are not limited to, reagents suitable for detecting the expression of CD63, CD9, Alix, β-actin, S100A6, Fibulin-1 (FBLN1), Coagulation factor X, Collagen alpha-2(VI) chain (COL6A2), Protocadherin Fat 4 (FAT4), Protocadherin Fat 1 (FAT1), and Fibrinogen beta chain on exosomes.

A number of kits are contemplated to encompass a variety of methods. These kits optionally include reagents to process a tissue or cell sample for the technique employed by that particular kit. By example, a kit for PCR or PCR enhanced in situ hybridization can include reagents to process the sample and isolate the RNA (for PCR). It will also contain suitable primers to amplify the target sequence and additional probes, if necessary, to detect the desired nucleic acid fragments as well as buffers and reagents for the polymerase chain reaction and the buffers and emulsions required for in situ hybridization methods. Other kits can alternatively include reagents for immunofluorescence or ELISA using antibodies to the integrin subunits and/or probes, primers and reagents for modifications of in situ or PCR in situ hybridization methods.

For the purposes of the kits of the present invention, the isolation of nucleic acids from the exosomal sample may be desirable. Accordingly, kits may contain reagents necessary to carry out such methods. Methods of isolating RNA and DNA from biological samples for use in the methods of the present invention are readily known in the art. These methods are described in detail in LABORATORY TECHNIQUES IN BIOCHEMISTRY AND MOLECULAR BIOLOGY: HYBRIDIZATION WITH NUCLEIC ACID PROBES, PART I. THEORY AND NUCLEIC ACID PREPARATION (P. Tijssen ed., Elsevier 1993), which is hereby incorporated by reference in its entirety. Total RNA can be isolated from a given sample using, for example, an acid guanidinium-phenol-chloroform extraction, a guanidinium isothiocyanate-ultracentrifugation method, or lithium chloride-SDS-urea method. PolyA$^+$ mRNA can be isolated using oligo(dT) column chromatography or (dT)n magnetic beads (See e.g., SAMBROOK AND RUSSELL, MOLECULAR CLONING: A LABORATORY MANUAL (Cold Springs Laboratory Press, 1989) or CURRENT PROTOCOLS IN MOLECULAR BIOLOGY (Fred M. Ausubel et al. eds., 1992) which are hereby incorporated by reference in their entirety). See also WO/2000024939 to Dong et al., which is hereby incorporated by reference in its entirety, for complexity management and other nucleic acid sample preparation techniques.

It may be desirable to amplify the nucleic acid sample prior to detecting integrin expression. One of skill in the art will appreciate that a method which maintains or controls for the relative frequencies of the amplified nucleic acids to achieve quantitative amplification should be used.

Typically, methods for amplifying nucleic acids employ a polymerase chain reaction (PCR) (See e.g., PCR TECHNOLOGY: PRINCIPLES AND APPLICATIONS FOR DNA AMPLIFICATION (Henry Erlich ed., Freeman Press 1992); PCR PROTOCOLS: A GUIDE TO METHODS AND APPLICATIONS (Michael Innis ed., Academic Press 1990); Manila et al., "Fidelity of DNA Synthesis by the *Thermococcus litoralis* DNA Polymerase—An Extremely Heat Stable Enzyme with Proofreading Activity," *Nucleic Acids Res.* 19:4967-73 (1991); Eckert et al., "DNA Polymerase Fidelity and the Polymerase Chain Reaction," *PCR Methods and Applications* 1:17-24 (1991); and U.S. Pat. Nos. 4,683,202, 4,683,195, 4,800,159, 4,965,188, and 5,333,675 all to Mullis et al., which are hereby incorporated by reference in their entireties for all purposes). The sample can also be amplified on an array as described in U.S. Pat. No. 6,300,070 to Boles, which is hereby incorporated by reference in its entirety.

Other suitable amplification methods include the ligase chain reaction (LCR) (e.g. Wu et al., "The Ligation Amplification Reaction (LAR)—Amplification of Specific DNA Sequences Using Sequential Rounds of Template-Dependent Ligation," *Genomics* 4:560-9 (1989), Landegren et al., "A Ligase-Mediated Gene Detection Technique," *Science* 241:1077-80 (1988), and Barringer et al., "Blunt-End and Single-Strand Ligations by *Escherichia coli* Ligase: Influence on an In Vitro Amplification Scheme," *Gene* 89:117-22 (1990), which are hereby incorporated by reference in their entirety); transcription amplification (Kwoh et al., "Transcription-Based Amplification System and Detection of Amplified Human Immunodeficiency Virus Type I with a Bead-Based Sandwich Hybridization Format," *Proc. Natl. Acad. Sci. USA* 86:1173-7 (1989) and WO 88/10315 to Gingeras, which are hereby incorporated by reference in their entirety); self-sustained sequence replication (Guatelli et al., "Isothermal, In Vitro Amplification of Nucleic Acids by a Multienzyme Reaction Modeled After Retroviral Replication," *Proc. Natl. Acad. Sci. USA* 87:1874-8 (1990) and WO 90/06995 to Gingeras, which are hereby incorporated by reference in their entirety); selective amplification of target polynucleotide sequences (U.S. Pat. No. 6,410,276 to Burg at al., which is hereby incorporated by reference in its entirety); consensus sequence primed polymerase chain reaction (CP-PCR) (U.S. Pat. No. 5,437,975 to McClelland, which is hereby incorporated by reference in its entirety); arbitrarily primed polymerase chain reaction (AP-PCR) (U.S. Pat. No. 5,413,909 to Bassam, and U.S. Pat. No. 5,861,245 to McClelland which are hereby incorporated by reference in their entirety); and nucleic acid based sequence amplification (NABSA) (See U.S. Pat. Nos. 5,409,818, 5,554,517, and 6,063,603 all to Davey, which are hereby incorporated by reference in their entirety). Other amplification methods that may be used are described in U.S. Pat. No. 5,242,794 to Whiteley; U.S. Pat. No. 5,494,810 to Barany; and U.S. Pat. No. 4,988,617 to Landgren, which are hereby incorporated by reference in their entirety.

The kits may also contain probes or primers which hybridize to complementary nucleic acid molecules in the exosomal sample. The probes comprise nucleotide sequences that are complementary to at least a region of mRNA or corresponding cDNA of the desired integrins. As used herein, the term "hybridization" refers to the complementary base-pairing interaction of one nucleic acid with another nucleic acid that results in formation of a duplex, triplex, or other higher-ordered structure. Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes to complementary and substantially complementary target sequences are well known in the art (see e.g., NUCLEIC ACID HYBRIDIZATION, A PRACTICAL APPROACH, B. Hames and S. Higgins, eds., IRL Press, Washington, D.C. (1985), which is hereby incorporated by reference in its entirety). In general, hybridization is influenced by, among other things, the length of the polynucleotides and their complements, the pH, the temperature, the presence of mono- and divalent cations, the proportion of G and C nucleotides in the hybridizing region, the viscosity of the medium, and the presence of denaturants. Such variables influence the time required for hybridization. Thus, the preferred hybridization conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and single stranded nucleic acid probe. Thus, what is meant by complementarity herein is that the probes are sufficiently complementary to the target sequence to hybridize under the selected reaction conditions to achieve selective detection and measurement.

Detection of hybridization between probes and corresponding target molecules from an exosomal sample can be performed by several assays known in the art that permit detection of the expression level of the integrins. As described herein, the "expression level" of an integrin can be achieved by measuring any suitable value that is representative of the gene expression level. The measurement of gene expression levels can be direct or indirect. A direct measurement involves measuring the level or quantity of RNA or protein. An indirect measurement may involve measuring the level or quantity of cDNA, amplified RNA, DNA, or protein; the activity level of RNA or protein; or the level or activity of other molecules (e.g. a metabolite) that are indicative of the foregoing. The measurement of expression can be a measurement of the absolute quantity of a gene product. The measurement can also be a value representative of the absolute quantity, a normalized value (e.g., a quantity of gene product normalized against the quantity of a reference gene product), an averaged value (e.g., average quantity obtained at different time points or from different sample from a subject, or average quantity obtained using different probes, etc.), or a combination thereof.

In a preferred embodiment, hybridization is detected by measuring RNA expression level of the integrins. Measuring gene expression by quantifying mRNA expression can be achieved using any commonly used method known in the art including northern blotting and in situ hybridization (Parker et al., "mRNA: Detection by in Situ and Northern Hybridization," *Methods in Molecular Biology* 106:247-283 (1999), which is hereby incorporated by reference in its entirety); RNAse protection assay (Hod et al., "A Simplified Ribonuclease Protection Assay," *Biotechniques* 13:852-854 (1992), which is hereby incorporated by reference in its entirety); reverse transcription polymerase chain reaction (RT-PCR) (Weis et al., "Detection of Rare mRNAs via Quantitative RT-PCR," *Trends in Genetics* 8:263-264 (1992), which is hereby incorporated by reference in its entirety); and serial analysis of gene expression (SAGE) (Velculescu et al., "Serial Analysis of Gene Expression," *Science* 270:484-487 (1995); and Velculescu et al., "Characterization of the Yeast Transcriptome," *Cell* 88:243-51 (1997), which is hereby incorporated by reference in its entirety).

In a nucleic acid hybridization assay, the expression level of nucleic acids corresponding to integrins can be detected using an array-based technique. These arrays, also commonly referred to as "microarrays" or "chips" have been generally described in the art, see e.g., U.S. Pat. No. 5,143,854 to Pirrung et al.; U.S. Pat. No. 5,445,934 to Fodor et al.; U.S. Pat. No. 5,744,305 to Fodor et al.; U.S. Pat. No. 5,677,195 to Winkler et al.; U.S. Pat. No. 6,040,193 to Winkler et al.; U.S. Pat. No. 5,424,186 to Fodor et al., which are all hereby incorporated by reference in their entirety. A microarray comprises an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see Fodor et al., "Light-Directed, Spatially Addressable Parallel Chemical Synthesis," *Science* 251: 767-773 (1991); Pease et al., "Light-Generated Oligonucleotide Arrays for Rapid DNA Sequence Analysis," *Proc. Natl. Acad. Sci. U.S.A.* 91:5022-5026 (1994); Lockhart et al., "Expression Monitoring by Hybridization to High-Density Oligonucleotide Arrays," *Nature Biotechnology* 14:1675 (1996); and U.S. Pat. No. 5,578,832 to Trulson; U.S. Pat. No. 5,556,752 to Lockhart; and U.S. Pat. No. 5,510,270 to Fodor, which are hereby incorporated by reference in their entirety); (ii) spotting/printing at medium to low-density (e.g., cDNA probes) on glass, nylon or nitrocellulose (Schena et al., "Quantitative Monitoring of Gene Expression Patterns with a Complementary DNA Microarray," *Science* 270:467-470 (1995), DeRisi et al, "Use of a cDNA Microarray to Analyse Gene Expression Patterns in Human Cancer," *Nature Genetics* 14:457-460 (1996); Shalon et al., "A DNA Microarray System for Analyzing Complex DNA Samples Using Two-Color Fluorescent Probe Hybridization," *Genome Res.* 6:639-645 (1996); and Schena et al., "*Proc. Natl. Acad. Sci. U.S.A.* 93:10539-11286) (1995), which are hereby incorporated by reference in their entirety); (iii) masking (Maskos et al., "Oligonucleotide Hybridizations on Glass Supports: A Novel Linker for Oligonucleotide Synthesis and Hybridization Properties of Oligonucleotides Synthesised In Situ," *Nuc. Acids. Res.* 20:1679-1684 (1992), which is hereby incorporated by reference in its entirety); and (iv) dot-blotting on a nylon or nitrocellulose hybridization membrane (see e.g., SAMBROOK AND RUSSELL, MOLECULAR CLONING: A LABORATORY MANUAL (Cold Springs Laboratory Press, 1989), which is hereby incorporated by reference in its entirety). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA.

Fluorescently labeled cDNA for hybridization to the array may be generated through incorporation of fluorescent nucleotides by reverse transcription of RNA extracted from exosomal samples. Labeled cDNA applied to the array hybridizes with specificity to each nucleic acid probe spotted on the array. After stringent washing to remove non-specifically bound cDNA, the array is scanned by confocal laser microscopy or by another detection method, such as a CCD camera. Quantitation of hybridization of each arrayed element allows for assessment of corresponding mRNA abundance. With dual color fluorescence, separately labeled cDNA samples generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., "Parallel Human Genome Analysis: Microarray-Based Expression Monitoring of 1000 Genes," "*Proc. Natl. Acad. Sci. USA* 93(20):10614-9 (1996), which is hereby incorporated by reference in its entirety).

A nucleic acid amplification assay that is a semi-quantitative or quantitative real-time polymerase chain reaction (RT-PCR) assay can also be performed. Because RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MLV-RT), although others are also known and suitable for this purpose. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. An exemplary PCR amplification system using Taq polymerase is TaqMan® PCR (Applied Biosystems, Foster City, CA). Taqman® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect the nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, the ABI PRISM 7700° Sequence Detection System® (Perkin-Elmer-Applied Biosystems, Foster City, Calif., USA), or the Lightcycler (Roche Molecular Biochemicals, Mannheim, Germany).

In addition to the TagMan® primer/probe system, other quantitative methods and reagents for real-time PCR detection that are known in the art (e.g. SYBR green, Molecular Beacons, Scorpion Probes, etc.) are suitable for use in the methods of the present invention.

To minimize errors and the effect of sample-to-sample variation, RT-PCR is usually performed using an internal standard. The ideal internal standard is expressed at a constant level among different tissues. RNAs most frequently used to normalize patterns of gene expression are mRNAs for the housekeeping genes glyceraldehyde-3-phosphate-dehydrogenase (GAPDH) and β-actin.

Real time PCR is compatible both with quantitative competitive PCR, where internal competitor for each target sequence is used for normalization and quantitative comparative PCR using a normalization gene contained within the sample, or a housekeeping gene for RT-PCR. For further details see, e.g., Heid et al., "Real Time Quantitative PCR," *Genome Research* 6:986-994 (1996), which is incorporated by reference in its entirety.

When it is desirable to measure the expression level of integrins by measuring the level of protein expression, the kit may contain reagents suitable for performing any protein hybridization or immunodetection based assay known in the art. In a protein hybridization based assay, an antibody or other agent that selectively binds to a protein is used to detect the amount of that protein expressed in a sample. For example, the level of expression of a protein can be measured using methods that include, but are not limited to, western blot, immunoprecipitation, enzyme-linked immunosorbent assay (ELISA), radioimmunoassay (RIA), fluorescent activated cell sorting (FACS), immunohistochemistry, immunocytochemistry, or any combination thereof. Also, antibodies, aptamers, or other ligands that specifically bind to a protein can be affixed to so-called "protein chips" (protein microarrays) and used to measure the level of expression of a protein in a sample. Alternatively, assessing the level of protein expression can involve analyzing one or more proteins by two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), protein chip expression analysis, gene chip expression analysis, and laser densitometry, or any combinations of these techniques.

In certain embodiments, kits may contain an antibody that specifically binds an integrin. Optionally, the antibody can be fixed to a solid support to facilitate washing and subsequent isolation of the complex, prior to contacting the antibody with a sample. Examples of solid supports include glass or plastic in the form of a microtiter plate, a stick, a bead, or a microbead. Examples of solid supports encompassed herein include those formed partially or entirely of glass (e.g., controlled pore glass), polysaccharides (e.g., agarose), polyacrylamides, silicones, and plastics such as polystyrene, polypropylene and polyvinyl alcohol. The sample can be diluted with a suitable diluent or eluant before contacting the sample to the antibody.

After incubating the sample with antibodies, the mixture can be washed and the antibody-integrin complex formed can be detected. This can be accomplished by incubating the washed mixture with a detection reagent. This detection reagent may be a second antibody which is labeled with a detectable label, for example. Exemplary detectable labels include magnetic beads (e.g., DYNABEADS™), fluorescent dyes, radiolabels, enzymes (for example, horse radish peroxidase, alkaline phosphatase and others commonly used in an ELISA), and colorimetric labels such as colloidal gold or colored glass or plastic beads. Alternatively, the integrins in the sample can be detected using an indirect assay, wherein, for example, a second, labeled antibody is used to detect bound integrin-specific antibody, and/or in a competition or inhibition assay wherein, for example, a monoclonal antibody which binds to a distinct epitope of the integrin is incubated simultaneously with the mixture.

Immunoassays can be used to determine presence or absence of integrins in an exosomal sample as well as the quantity of the integrins in the sample. If an integrin is present in the sample, it will form an antibody-integrin complex with an antibody that specifically binds the integrin under suitable incubation conditions described above. The amount of an antibody-integrin complex can be determined by comparing to a standard. A standard can be a known compound or another protein known to be present in a sample, for example. As noted above, the test amount of integrin need not be measured in absolute units, as long as the unit of measurement can be compared to a control.

In one embodiment, the kits also contain reagents to separate tumor exosomes from normal exosomes. Preferably, these reagents detect exosomal expression of $ITG\beta_1$, $ITG\alpha_3$, $ITG\alpha_3$, Calreticulin (CALR), Coagulation factor V, Nidogen-1 (NID1), and Fibrinogen-like protein 1 on exosomes.

Another aspect of the present invention relates to a method of prognosing cancer in a subject. This method involves selecting a subject having cancer and obtaining, from the selected subject, a tissue sample. The tissue is then contacted with one or more reagents suitable to detect higher or lower levels or the presence or absence of one or more S100 molecules in the tissue, and the cancer is prognosed based on the contacting step.

Another aspect of the present invention relates to a method of treating a subject having cancer. This method involves selecting a subject having cancer characterized by a particular tissue S100 profile and administering to the selected subject a therapeutic S100 inhibitor corresponding to the tissue S100 profile.

In one embodiment, the one or more S100 molecules are selected from the group consisting of S100A8, S100A9, S100P, S100A4, S100A6, S100A10, S100A11, S100A13, and S100A16.

In one embodiment of the present invention, the method is carried out to determine whether the cancer is likely to metastasize to the liver by detecting higher or lower levels or the presence or absence of S100A8, S100A9 and/or S100P. Accordingly, where metastasis to the liver is determined to be likely, S100A8, S100A9 and S100P inhibitors may be administered to the subject.

In another embodiment, the method is carried out to determine whether the cancer is likely to metastasize to the lung by detecting higher or lower levels or the presence or absence of S100A4, S100A6, S100A10, S100A11, S100A13, and S100A16. Accordingly, where metastasis to the lung is determined to be likely, S100A4, S100A6, S100A10, S100A11, S100A13, and S100A16 inhibitors may be administered to the subject.

In another embodiment, the method is carried out to determine whether the cancer is likely to occur, recur, or metastasize by detecting higher or lower levels or the presence or absence of S100A8, S100A9, S100P, S100A4, S100A6, S100A10, S100A11, S100A13, and S100A16. Accordingly, when occurrence, recurrence, or metastasis is determined to be likely, S100A8, S100A9, S100P, S100A4, S100A6, S100A10, S100A11, S100A13, and S100A16 inhibitors may be administered to the subject.

The S100 inhibitors of the present invention may be any S100 inhibitor. In one embodiment, the inhibitor is an antibody, a peptide, peptidomimetic, or small molecule.

As described herein, S100 molecules are upregulated in a Src/p38-dependent manner. Accordingly, inhibitors of S100 proteins, as well as inhibitor of src and p38 are also contemplated.

Exemplary src inhibitors include, without limitation, 1-Naphthyl PP1, A419259 trihydrochloride, AZM 475271, Bosutinib, Damnacanthal, Herbimycin A, KB SRC 4, Lavendustin A, Lyn peptide inhibitor, MNS, PD 166285 dihydrochloride, PD180970, Piceatannol, PP1, PP2, PP3, pp60 c-src (521-533), Src 11, TC-S 7003, and WH-4-023.

Exemplary p38 inhibitors include, without limitation, AL 8697, AMG 548, CMPD-1, DBM 1285 dihydrochloride, EO1428, JX401, ML3403, RWJ67657, SB202190, SB203580, SB203580 hydrochloride, SB239063, SB706504, SCIO 469 hydrochloride, SKF 86002 dihydrochloride, SX 011, TA 01, TA 02, TAK 715, VX 702, and VX 745.

Exemplary S100A inhibitors include, without limitation, Niclosamide and Trifluoperazine.

Exemplary S100A8 inhibitors include, without limitation, anti-S100A8/9 antibody, PP2, and anti-S100A8 antibody.

Exemplary S100A9 inhibitors include, without limitation, anti-S100A8/9 antibody, Paquinimod, PP2, and anti-S100A8 antibody.

Other materials and methods for administering S100, Src, and p38 inhibitors are substantially the same materials and methods described above.

Other materials and methods suitable for detecting higher or lower levels or the presence or absence of one or more S100 molecules in a sample are also substantially the same materials and methods described above.

In addition to S100 molecules, a number of proteins have been identified that are upregulated upon exosome education of pre-metastatic sites. Thus, these methods of the present invention also encompass detecting higher or lower levels or the presence or absence of one or more proteins expressed from genes identified in Table 1 below as well as administering therapeutic inhibitors of these proteins for the treatment of cancer.

TABLE 1

Fold Change in Kupffer Cells After BxPC-3-LiT Exosome Treatment

| Gene | logFC | Known Inhibitors |
| --- | --- | --- |
| MPEG1 | 9.58373243 | |
| HLA-DRA | 9.55650147 | |
| NPPB | 9.51851725 | chloride channel blockers, ie. Genistein |
| C1QC | 9.17377204 | |
| FAM163A | 8.96894228 | |
| C1QB | 8.96875148 | |
| HLA-DQA1 | 8.90536723 | |
| MDFI | 8.84950084 | |
| LRRC38 | 8.818683 | |
| HLA-DQB1 | 8.75348566 | |
| RSPO3 | 8.22457446 | anti-RSPO3 ab, OMP-131R10 |
| HS3ST2 | 8.20813903 | |
| RNASE1 | 8.00972958 | |
| LILRB4 | 7.7787282 | |
| SLC22A3 | 7.75426279 | |
| TMEM176A | 7.74253666 | |
| MS4A4A | 7.71849897 | |
| ECEL1 | 7.57981282 | |
| MYL7 | 7.55541868 | |
| FCGR3A | 7.50143018 | IgG |
| CD53 | 7.44391304 | |
| SAA1 | 7.43432764 | |
| DHRS3 | 7.41458735 | |
| TYROBP | 7.26831873 | |
| DSC2 | 7.24198824 | |
| HLA-DRB5 | 7.21457265 | |
| GDF2 | 7.20368575 | |
| CMKLR1 | 7.17191687 | CMKLR1 small molecular antagonists, Sparrho |
| PDK4 | 7.17153323 | |
| FCGR2B | 7.03889563 | IgG |
| LCN1 | 6.93276974 | |
| FAM163B | 6.91160584 | |
| IL10RA | 6.88853706 | |
| HCK | 6.8836487 | bosutinib |
| LINC00473 | 6.87771947 | |
| CD226 | 6.87118394 | |
| LILRB5 | 6.85118457 | |
| NPY1R | 6.83237658 | GR 231118, BIBO 3304 trifluoroacetate, BMS 193885, PD 160170, BIBP 3226 trifluoroacetate |
| GATA5 | 6.81396224 | |
| MYH13 | 6.72374189 | |
| CD86 | 6.70177773 | abatacept, belatacept, abatacept/methotrexate |
| TMEM176B | 6.68568134 | |
| SPI1 | 6.67890878 | |
| SIGLEC1 | 6.63783068 | |

TABLE 1-continued

Fold Change in Kupffer Cells After BxPC-3-LiT Exosome Treatment

| Gene | logFC | Known Inhibitors |
| --- | --- | --- |
| C1QA | 6.63208777 | rituximab |
| ZNF727 | 6.63175163 | |
| CSF3 | 6.57851366 | cladribine/cytarabine/filgrastim, cytarabine/filgrastim/fludarabine phosphate, cladribine/cytarabine/filgrastim/mitoxantrone, clofarabine/cytarabine/filgrastim, cytarabine/filgrastim/fludarabine phosphate/idarubicin, cladribine/cytarabine/filgrastim/idarubicin, darbepoetin alfa/filgrastim, EPO/filgrastim, cladribine/cytarabine/filgrastim/idarubicin/plerixafor, clofarabine/filgrastim/idarubicin, clofarabine/cytarabine/filgrastim/idarubicin, clofarabine/filgrastim, pegfilgrastim, filgrastim |
| LOC283867 | 6.53845607 | |
| PIK3R5 | 6.5329929 | SF1126, PI-3 kinase inhibitors |
| FGFR2 | 6.43944944 | lenvatinib, nintedanib, regorafenib, dexamethasone/thalidomide, bortezomib/dexamethasone/thalidomide, rituximab/thalidomide, bortezomib/thalidomide, prednisone/thalidomide, BAY1179470, lucitanib, debio 1347, ARQ 087, thalidomide, palifermin |
| FAM43B | 6.41788245 | decitabine |
| NR1H4 | 6.40998403 | |
| HLA-DRB1 | 6.40889534 | apolizumab |
| MRC1 | 6.37430612 | technetium Tc 99m tilmanocept |
| ZFP57 | 6.37194975 | |
| KCNQ3 | 6.34545068 | ezogabine |
| CCL20 | 6.26557676 | |
| LIPM | 6.26025495 | |
| ACTBL2 | 6.26019547 | |
| FOLR2 | 6.25408795 | |
| SEL1L2 | 6.21356309 | |
| BMP10 | 6.19502747 | Dalarntercept |
| TM4SF18 | 6.19268909 | |
| PCDHA5 | 6.12683703 | |
| LILRB2 | 6.12469351 | |
| OTOF | 6.1232181 | |
| DENND1C | 6.12209972 | |
| CD79B | 6.11929445 | Chki inhibitors, GDC-0575 |
| PI3 | 6.05648856 | |
| S100B | 6.05572426 | |
| ROBO2 | 6.05438424 | |
| CD300A | 6.05345912 | |
| PLA2G5 | 6.02081901 | varespladib methyl, varespladib |
| PTGS2 | 6.00536037 | acetaminophen/pentazocine, acetaminophen/clemastine/pseudoephedrine, aspirin/butalbital/caffeine, acetaminophen/caffeine/dihydrocodeine, aspirin/hydrocodone, aspirin/oxycodone, acetaminophen/aspirin/caffeine, aspirin/pravastatin, acetaminophen/dexbrompheniramine/pseudoephedrine, aspirin/meprobamate, aspirin/caffeine/propoxyphene, aspirin/butalbital/caffeine/codeine, aspirin/caffeine/dihydrocodeine, chlorpheniramine/ibuprofen/pseudoephedrine, licofelone, menatetrenone, icosapent, suprofen, lornoxicam, tiaprofenic acid, lumiracoxib, tenoxicam, naproxen/sumatriptan, parecoxib, ibuprofen/phenylephrine, acetaminophen/aspirin/codeine, esomeprazole/naproxen, aspirin/esomeprazole, aspirin/dipyridamole/telmisartan, famotidine/ibuprofen, aspirin/dabigatran etexilate, diclofenac/omeprazole, chlorpheniramine/ibuprofen/phenylephrine, dexamethasone/pomalidomide, sulindac/tamoxifen, sulindac/toremifene, raloxifene/sulindac, ketorolac/phenylephrine, aspirin/bivalirudin, diclofenac/hyaluronic acid, COX2 inhibitor, diclofenac/misoprostol, acetaminophen/butalbital/caffeine, hydrocodone/ibuprofen, acetaminophen/hydrocodone, acetaminophen/tramadol, acetaminophen/codeine, acetaminophen/oxycodone, acetaminophen/propoxyphene, niflumic acid, nitroaspirin, ketoprofen, diclofenac, etoricoxib, naproxen, meclofenamic acid, pomalidomide, meloxicam, celecoxib, dipyrone, nimesulide, acetaminophen, mefenamic acid, diflunisal, ibuprofen, GW406381X, phenylbutazone, indomethacin, sulfasalazine, piroxicam, valdecoxib, aspirin, carprofen, zomepirac, rofecoxib, aspirin/caffeine/orphenadrine, acetaminophen/butalbital, balsalazide, aspirin/dipyridamole, acetaminophen/butalbital/caffeine/codeine, racemic flurbiprofen, phenacetin, sulindac, nabumetone, etodolac, tolmetin, ketorolac, oxaprozin, mesalamine, salsalate, fenoprofen, salicylic acid, acetaminophen/caffeine/chlorpheniramine/hydrocodone/phenylephrine, bromfenac |

TABLE 1-continued

Fold Change in Kupffer Cells After BxPC-3-LiT Exosome Treatment

| Gene | logFC | Known Inhibitors |
| --- | --- | --- |
| MS4A6A | 5.98201002 | |
| RNASE6 | 5.98065626 | |
| NEFM | 5.96086304 | |
| CA2 | 5.90857707 | ethoxyzolamide, dichlorphenamide, phentermine/topiramate, brimonidine/brinzolamide, methazolamide, diazoxide, hydrochlorothiazide, acetazolamide, trichloromethiazide, dorzolamide, chlorothiazide, dorzolamide/timolol, brinzolamide, chlorothiazide/reserpine, quinethazone, chlorthalidone, benzthiazide, sulfacetamide, topiramate |
| LAPTM5 | 5.83201189 | |
| LGI2 | 5.82376377 | |
| HK3 | 5.81249255 | |
| RARRES1 | 5.79323798 | |
| DNER | 5.77000087 | |
| CTAGE1 | 5.7545713 | |
| FAM110C | 5.74805945 | |
| TP53TG3D | 5.73647203 | |
| MARCO | 5.73559841 | |
| CXCR7 | 5.73479811 | Nox-A12 |
| SELE | 5.72811755 | |
| NKD2 | 5.72561623 | |
| EGFL6 | 5.71343792 | TAS102 |
| COL4A4 | 5.7120067 | collagenase clostridium histolyticum |
| RHCG | 5.69820847 | |
| GGT3P | 5.67581289 | |
| PTPRC | 5.6731015 | 111 In-BC8 |
| AWAT2 | 5.64805095 | |
| SOST | 5.64598517 | |
| SIGLEC7 | 5.64499365 | |
| ATP6V0A4 | 5.6351181 | |
| FAM5B | 5.59386403 | |
| CYMP | 5.52779089 | |
| ALDH1A3 | 5.5126134 | |
| IL1R2 | 5.49126974 | Anakinra |
| DOK2 | 5.44588983 | |
| ANKRD1 | 5.43149807 | |
| FLRT3 | 5.4261097 | |
| TDRD9 | 5.38523981 | |
| PLBD1 | 5.38172349 | |
| CYBB | 5.36353442 | |
| HAPLN1 | 5.34137599 | |
| OVCH1 | 5.33928168 | |
| HLA-DQA2 | 5.33825048 | |
| ST6GALNAC3 | 5.33792068 | |
| SASH3 | 5.33292616 | |
| SOX11 | 5.33165326 | |
| SLC22A2 | 5.32990753 | |
| HTR2A | 5.30822089 | paliperidone, risperidone, buspirone, caffeine/ergotamine, iloperidone, eplivanserin, blonanserin, flibanserin, asenapine, ocaperidone, abaperidone, psilocybine, APD125, cariprazine, thioproperazine, lurasidone, opipramol, paliperidone palmitate, brexpiprazole, cinitapride, pipothiazine, amitriptyline/ketamine, chloropromazine, trazodone, flupenthixol, cisapride, chlorprothixene, clozapine, doxepin, desipramine, cyproheptadine, clomipramine, fluoxetine/olanzapine, thiothixene, amitriptyline/perphenazine, loxapine, amitriptyline/chlordiazepoxide, epinastine, fenfluramine, quetiapine, olanzapine, nefazodone, mirtazapine, amitriptyline, cyclobenzaprine, nortriptyline, lisuride, sertindole, ziprasidone, mesoridazine, thioridazine, aripiprazole, methysergide, dihydroergotamine, apomorphine, ergotamine, azatadine |
| NCKAP1L | 5.28054054 | |
| DNASE1L3 | 5.27411326 | |
| PDE3B | 5.251792 | dyphylline, nitroglycerin, medorinone, aminophylline, cilostazol, dipyridamole, amrinone, tolbutamide, theophylline, pentoxifylline |
| DAW1 | 5.24803135 | Tizanidine |
| LRRC7 | 5.24528379 | |
| ST8SIA6-AS1 | 5.23563668 | |
| TENM2 | 5.21975286 | |
| FGF16 | 5.2127342 | Flakka |
| TAS2R1 | 5.21004729 | |
| GIMAP6 | 5.21003608 | |
| EMR3 | 5.20714438 | |
| HLA-DQB2 | 5.20543877 | |
| GCSAML-AS1 | 5.20535166 | |
| LOC554223 | 5.20527343 | |

TABLE 1-continued

Fold Change in Kupffer Cells After BxPC-3-LiT Exosome Treatment

| Gene | logFC | Known Inhibitors |
|---|---|---|
| CYP2S1 | 5.16463673 | |
| ENPP3 | 5.15635174 | |
| CPXM2 | 5.14332794 | |
| IL33 | 5.12584362 | Tizanidine, Arcalyst |
| SELP | 5.10853045 | |
| C4BPB | 5.09950297 | |
| IL1A | 5.08122738 | |
| IGSF21 | 5.07618536 | mecasemin rinfabate |
| FLJ25363 | 5.07610776 | |
| PDPN | 5.07472559 | |
| ECSCR | 5.06513012 | |
| PRR26 | 5.04138235 | |
| SPOCK3 | 5.03632638 | |
| POMC | 5.02895058 | |
| CNKSR2 | 5.00698469 | |
| FBXO16 | 5.00035526 | |
| PGR | 4.98223561 | misoprostol, dienogest, ulipristal acetate, asoprisnil, ethynodiol diacetate, norethindrone acetate, ethinyl estradiol/ethynodiol diacetate, estradiol cypionate/medroxyprogesterone acetate, tosagestin, estradiol/norethindrone acetate, ZK 230211, etonogestrel, nestorone, tela pristone acetate, ethinyl estradiol/etonogestrel, 17alpha-hydroxyprogesterone caproate, leuprolide acetate/norethindrone acetate, megestrol acetate/tamoxifen, ulipristal, tanaproget, progesterone receptor antagonist, desogestrel/ethinyl estradiol, drospirenone/ethinyl estradiol, ethinyl estradiol/norelgestromin, ethinyl estradiol/norethindrone, ethinyl estradiol/levonorgestrel, ethinyl estradiol/norgestrel, ethinyl estradiol/norgestimate, conjugated estrogen/medroxyprogesterone acetate, mometasone furoate, megestrol acetate, drospirenone, medroxyprogesterone acetate, norgestrel, dydrogesterone, desogestrel, danazol, levonorgestrel, norelgestromin, mifepristone, norethindrone, norgestimate, progesterone |
| PAK3 | 4.96584265 | |
| LRRC4C | 4.96535004 | |
| KCNK1 | 4.96153495 | |
| STAB1 | 4.94959803 | stabilin 1 |
| MYH8 | 4.94142632 | |
| MIR146A | 4.93645826 | |
| ANGPTL4 | 4.93375597 | N-acetyl-D. mannosamine |
| IRX2 | 4.93227207 | cox-2 inhibitor |
| APLNR | 4.93007753 | |
| SLN | 4.93005698 | |
| PRKCQ | 4.93002935 | sotrastaurin, ingenol mebutate |
| HLA-DRB6 | 4.92946193 | |
| SLC6A12 | 4.92689789 | tiagabine |
| HS3ST1 | 4.92657855 | |
| ELK2AP | 4.92637687 | |
| EPB41L3 | 4.91982113 | |
| PDE4B | 4.88957572 | enprofylline, dyphylline, nitroglycerin, caffeine/ergotamine, arofylline, tetomilast, L 869298, ibudilast, apremilast, aminophylline, anagrelide, cilomilast, milrinone, dipyridamole, L-826,141, ketotifen, roflumilast, tolbutamide, papaverine, theophylline, pentoxifylline, caffeine |
| UPB1 | 4.88940686 | |
| TREM1 | 4.86348204 | |
| GPRIN3 | 4.8616948 | |
| CHRDL2 | 4.85762549 | |
| GIMAP8 | 4.85590911 | |
| CD200 | 4.84448438 | |
| SAA2 | 4.81274601 | |
| F3 | 4.81145914 | activated recombinant human factor VII |
| SUSD3 | 4.81035187 | |
| MMP9 | 4.78799535 | Batimastat, MMP-9/MMP-13 Inhibitor II, cis-ACCP, CP 471474, Chlorhexidine Dihydrochloride, MMP Inhibitor II, Actinonin SB-3CT, MMP-9 Inhibitor I, GM 6001, MMP Inhibitor V, Actinonin, MMP2/MMP9 inhibitor I, MMP2/MMP9 inhibitor II, MMP2/MMP9 inhibitor V, GS-5745, marimastat, glucosamine |
| CCL7 | 4.76971934 | |
| KLHL33 | 4.76669952 | |
| FRRS1L | 4.76601582 | |
| CSF3R | 4.76570045 | |
| S100A9 | 4.7651091 | |
| S100A8 | 4.76508455 | |
| OR3A2 | 4.76508039 | |
| FMO1 | 4.76428022 | |

TABLE 1-continued

Fold Change in Kupffer Cells After BxPC-3-LiT Exosome Treatment

| Gene | logFC | Known Inhibitors |
|---|---|---|
| INHBB | 4.76289553 | |
| GPC3 | 4.7558637 | |
| SLC2A5 | 4.75434606 | |
| KIF21B | 4.7454819 | |
| IRF8 | 4.73889143 | |
| CD163 | 4.72700301 | |
| IL1B | 4.72108436 | canakinumab, gevokizumab, canakinumab/INS, gallium nitrate |
| ENPP4 | 4.71020571 | |
| P2RX1 | 4.70330244 | |
| NOVA1 | 4.70058716 | |
| KCNH2 | 4.69988952 | dextromethorphan/quinidine, amiodarone, procainamide, pimozide, dofetilide, quinidine, halofantrine, propafenone, sotalol, amitriptyline, ibutilide |
| EPGN | 4.69567326 | |
| PLA2G7 | 4.68182358 | darapladib |
| GFRA1 | 4.67394009 | |
| SLITRK4 | 4.67017981 | |
| LRRN4 | 4.66053352 | |
| ALDH1A1 | 4.60279625 | disulfiram, chlorpropamide |
| KCNT2 | 4.5933886 | |
| TDRD1 | 4.59296707 | |
| GGT1 | 4.59143841 | |
| NPY5R | 4.58667327 | NPY 5RA972, LU AA33810, S 25585, NTNCB hydrochloride, CGP 71683 hydrochloride, L-152,804 |
| LTC4S | 4.58453859 | |
| LHX2 | 4.57638861 | |
| LOC375196 | 4.50492389 | |
| INPP5D | 4.48493804 | |
| SFRP4 | 4.4714581 | |
| EPHX2 | 4.44978895 | |
| PRSS21 | 4.44700394 | |
| MEOX1 | 4.44613445 | |
| DAPK1 | 4.42725124 | |
| ZMAT4 | 4.41373862 | |
| PABPC4L | 4.41028412 | |
| MXRA5 | 4.4101515 | |
| KRT17 | 4.40360436 | |
| HMSD | 4.40038507 | |
| SPESP1 | 4.39861995 | |
| SYNPO2L | 4.39618724 | |
| NLRP2 | 4.38688532 | |
| FBP1 | 4.38577848 | |
| STEAP4 | 4.36868808 | |
| IL24 | 4.36224958 | |
| COL4A3 | 4.36064999 | collagenase clostridium histolyticum |
| PCSK6 | 4.35712739 | |
| SLC19A3 | 4.35012427 | |
| CCL13 | 4.34913092 | |
| KLHL13 | 4.34496648 | |
| AJAP1 | 4.34489832 | |
| EN1 | 4.34246305 | |
| VANGL2 | 4.33284223 | |
| FGD5 | 4.33184378 | |
| SLC6A15 | 4.33026941 | |
| ZNF208 | 4.32775764 | |
| SHISA3 | 4.31108796 | |
| IL18R1 | 4.28885243 | |
| SULT1E1 | 4.27864189 | estrogen sulfotransferase inhibitor |
| UNC5D | 4.27171622 | |
| STRA6 | 4.27006731 | |
| BEGAIN | 4.26782147 | |
| EGLN3 | 4.26354201 | |
| LOC100507254 | 4.26320144 | |
| ACE2 | 4.25977071 | TAPI-2, Captopril, Perindoprilat, enalapril, Benazepril-d5, (1R) Perindopril-d4, Quinapril, ramipril, Imidrapil, Benazeprilat-d5, Ramipril-d5hydrochlorothiazide/lisinopril, hydrochlorothiazide/moexipril, moexipril, lisinopril |
| SNRPN | 4.25520439 | |
| CPPED1 | 4.24947517 | |
| BCHE | 4.2415758 | 1-Naphthyl-N-methylcarbamate, Alternaeiol, Dichlorvos, Pyrantel Pamoate, Terbutaline Hemisulfate, Bambuterol Hydrochloride, CMPF, Carbofuran-d3, Tetraisopropyl pyrophosphate, 4-Amino-benzylpiperidine, Diazinon, Naled, Aldicarb, PE 154, dipivefrin, malathion, hexafluorenium, atropine/edrophonium, echothiophate, tacrine, edrophonium, isoflurophate, pyridostigmine, pralidoxime, rivastigmine |

TABLE 1-continued

Fold Change in Kupffer Cells After BxPC-3-LiT Exosome Treatment

| Gene | logFC | Known Inhibitors |
|---|---|---|
| ZNF257 | 4.22851903 | |
| ITLN1 | 4.21969242 | |
| MPO | 4.21879896 | Isovitexin, 2-Thioxanthine, Myeloperoxidase Inhibitor-I |
| BEX2 | 4.2162751 | |
| PCDHA10 | 4.21245111 | |
| ZP1 | 4.21219619 | |
| HRASLS | 4.20959478 | |
| RASIP1 | 4.19703385 | |
| MCTP2 | 4.19513896 | |
| IGFN1 | 4.18366036 | |
| LILRA3 | 4.17997922 | |
| LOC100128054 | 4.1693378 | |
| LSP1 | 4.14701758 | |
| PIEZO2 | 4.14658602 | |
| TMEM200C | 4.12822151 | |
| PDC | 4.11871691 | |
| SERPINB9 | 4.11851331 | |
| BMP4 | 4.11784806 | |
| ICAM1 | 4.11278884 | |
| PRKAA2 | 4.09922437 | |
| MAOA | 4.09388108 | ladostigil, CX-1370, moclobemide, MAO-A inhibitor, phentermine/topiramate, fenfluramine/phentermine, methamphetamine, dextroamphetamine, procainamide, tranylcypromine, phenelzine, iproniazid, isocarboxazid, phentermine, benzphetamine, N-(2-indanyl)glycinamide |
| ADH4 | 4.08802354 | Fomepizole, 3-Hydroxypropionamide |
| ATP8A2 | 4.07161919 | |
| SLC16A5 | 4.06315849 | |
| IGSF10 | 4.05726708 | |
| PTPRZ1 | 4.05423319 | |
| NEBL | 4.03413445 | |
| PHKA1 | 4.03195492 | |
| RBM47 | 4.02899711 | |
| GJA5 | 4.00845339 | |
| ESRRG | 4.00626555 | diethylstilbestrol |
| KBTBD11 | 4.00236802 | |
| IQSEC3 | 4.00125469 | |
| KCNA3 | 4.00122423 | dalfampridine |
| ANO5 | 3.99500034 | |
| SFTA1P | 3.98995555 | |
| FMO3 | 3.97559404 | |
| F2RL1 | 3.95168329 | |
| NCF4 | 3.95140638 | |
| CXCL14 | 3.947349 | |
| TDO2 | 3.93890072 | |
| HRASLS5 | 3.93884983 | |
| FXYD6 | 3.93846183 | |
| GNG2 | 3.93701082 | |
| COL6A5 | 3.93691211 | |
| VSIG4 | 3.93446597 | |
| TBX5-AS1 | 3.93330445 | |
| MYOZ2 | 3.92941842 | |
| DSG2 | 3.9279198 | |
| PDLIM3 | 3.92312398 | |
| NEFH | 3.92074292 | |
| TFPI2 | 3.91112948 | |
| L3MBTL4 | 3.90972009 | |
| PTGFRN | 3.89594755 | |
| GAS1 | 3.87563393 | |
| FBN2 | 3.86732808 | |
| THEGL | 3.86722849 | |
| CELF2 | 3.86485154 | |
| IL18 | 3.86124355 | |
| AIF1 | 3.8604042 | |
| PF4 | 3.85983922 | |
| METTL24 | 3.85954928 | |
| SYTL5 | 3.8532298 | |
| CHD7 | 3.83849626 | |
| CLCN4 | 3.83474299 | |
| P2RY6 | 3.83005565 | |
| BMPR1B | 3.82661432 | |
| RASGRP1 | 3.82493461 | |
| PTPRE | 3.82352306 | |
| TMEM178B | 3.82324827 | |

TABLE 1-continued

Fold Change in Kupffer Cells After BxPC-3-LiT Exosome Treatment

| Gene | logFC | Known Inhibitors |
|---|---|---|
| TUBB4A | 3.82100962 | epothilone B, colchicine/probenecid, larotaxel, ABT-751, eribulin, simotaxel, davunetide, vintafolide, milataxel, cevipabulin, gemcitabine/paclitaxel, docetaxel/prednisone, capecitabine/docetaxel, paclitaxel/trastuzumab, cyclophosphamide/prednisone/vincristine, docetaxel/hydrocortisone, cyclophosphamide/docetaxel, gemcitabine/vinorelbine, cyclophosphamide/daunorubicin/imatinib/prednisone/vincristine, cyclophosphamide/topotecan/vincristine, docetaxel/gemcitabine, docetaxel/gemcitabine/vincristine, irinotecan/vincristine, irinotecan/temozolomide/vincristine, bevacizumab/paclitaxel, cyclophosphamide/docetaxel/epirubicin/5-fluorouracil/trastuzumab, docetaxel/trastuzumab, trastuzumab/vinorelbine, gemcitabine/oxaliplatin/paclitaxel, cyclophosphamide/epirubicin/vincristine, docetaxel/irinotecan, docetaxel/5-fluorouracil/oxaliplatin, capecitabine/docetaxel/gemcitabine, L-asparaginase/prednisone/vincristine, cyclophosphamide/etoposide/prednisone/rituximab/vincristine, cyclophosphamide/vinorelbine, cyclophosphamide/mitoxantrone/prednisone/vincristine, cyclophosphamide/etoposide/prednisone/vincristine, cyclophosphamide/prednisone/rituximab/vincristine, cyclophosphamide/mitoxantrone/prednisone/rituximab/vincristine, plinabulin, docetaxel/epirubicin, docetaxel/paclitaxel, epirubicin/paclitaxel, bevacizumab/paclitaxel/topotecan, paclitaxel/topotecan, bevacizumab/docetaxel, cyclophosphamide/prednisolone/vincristine, cyclophosphamide/prednisolone/rituximab/vincristine, cyclophosphamide/epirubicin/5-fluorouracil/vinorelbine, cyclophosphamide/epirubicin/5-fluorouracil/paclitaxel/trastuzumab, cyclophosphamide/epirubicin/5-fluorouracil/paclitaxel, cyclophosphamide/docetaxel/epirubicin/5-fluorouracil, cyclophosphamide/docetaxel/trastuzumab, cyclophosphamide/gemcitabine/prednisolone/rituximab/vincristine, BMS-275183, docetaxel, vinflunine, vinorelbine, vincristine, vinblastine, paclitaxel, podophyllotoxin, colchicine |
| CCR1 | 3.81860157 | |
| ENPP5 | 3.81786263 | |
| PLIN2 | 3.81703778 | |
| RHBDF2 | 3.80963255 | |
| HHIP | 3.8048875 | |
| AP1S3 | 3.80244526 | |
| FRAS1 | 3.79875687 | |
| PPP4R4 | 3.78728546 | |
| FHL1 | 3.78446527 | |
| WIPF3 | 3.7839193 | |
| SLC47A1 | 3.77864129 | |
| ITLN2 | 3.77842547 | |
| ARPP21 | 3.77754442 | |
| ADAMDEC1 | 3.7769449 | |
| ALDH1A2 | 3.77655515 | N,N'-Octamethylenebis(2,2-dichloroacetamide) |
| PTCRA | 3.77530265 | |
| EPHX4 | 3.77371048 | |
| CYP11A1 | 3.77233553 | |
| RGS18 | 3.77214932 | |
| UBXN10 | 3.77144936 | |
| IL1RL1 | 3.77039722 | |
| DACT2 | 3.76693256 | |
| APOA1 | 3.76617342 | |
| F11R | 3.76254601 | |
| FAM20A | 3.76070418 | |
| ERG | 3.75854546 | |
| GABRA5 | 3.75032883 | methohexital, primidone, meprobamate, aspirin/butalbital/caffeine, aspirin/meprobamate, aspirin/butalbital/caffeine/codeine, hexobarbital, pagoclone, alphadolone, SEP 174559, heptabarbital, zopiclone, clobazam, nitrazepam, adinazolam, butobarbital, acetaminophen/butalbital/caffeine, sevoflurane, isoflurane, gaboxadol, isoniazid, felbamate, etomidate, muscimol, halothane, fluoxetine/olanzapine, amobarbital, estazolam, atropine/hyoscyamine/phenobarbital/scopolamine, clorazepate, acetaminophen/butalbital, eszopiclone, quazepam, mephobarbital, hyoscyamine/phenobarbital, amitriptyline/chlordiazepoxide, acetaminophen/butalbital/caffeine/codeine, butabarbital, diazepam, temazepam, zolpidem, chlordiazepoxide, lorazepam, olanzapine, triazolam, flumazenil, clonazepam, flurazepam, midazolam, |

TABLE 1-continued

Fold Change in Kupffer Cells After BxPC-3-LiT Exosome Treatment

| Gene | logFC | Known Inhibitors |
|---|---|---|
| | | flunitrazepam, oxazepam, alprazolam, zaleplon, thiamylal, secobarbital, barbital, butalbital, phenobarbital, pentobarbital, thiopental, ezogabine, desflurane, methoxyflurane, enflurane, pregnenolone |
| CCDC152 | 3.73890358 | |
| C8orf4 | 3.73255262 | |
| CSF2 | 3.71899144 | sargramostim, EPO/sargramostim, rituximab/sargramostim |
| INMT | 3.71825555 | |
| ASB5 | 3.71485788 | |
| C7orf29 | 3.70638432 | |
| EFHC2 | 3.69413248 | |
| COL11A1 | 3.69154356 | collagenase clostridium histolyticum |
| FILIP1 | 3.68651548 | |
| PRG2 | 3.67764722 | |
| ANXA10 | 3.67749665 | |
| ANXA3 | 3.67013805 | |
| SAMSN1 | 3.66452705 | |
| KCNMB1 | 3.65987648 | tedisamil |
| LOC728377 | 3.65550527 | |
| CFH | 3.65522796 | |
| DOK6 | 3.63526058 | |
| CARD11 | 3.61813685 | |
| PDE9A | 3.61286489 | |
| MAOB | 3.6097572 | safinamide, ladostigil, rasagiline, MAO-B inhibitor, phentermine/topiramate, fenfluramine/phentermine, pargyline, methamphetamine, selegiline, dextroamphetamine, procainamide, tranylcypromine, phenelzine, isocarboxazid, phentermine, benzphetamine |
| KIAA1324L | 3.60901344 | |
| LOC100130238 | 3.60453978 | |
| CD300LF | 3.59971 | |
| STEAP1 | 3.59839133 | |
| ATG9B | 3.59552245 | |
| CSF2RB | 3.57803892 | |
| C5orf58 | 3.56963354 | |
| GKN2 | 3.56795071 | |
| PCDH7 | 3.56529102 | |
| B3GNT5 | 3.54649997 | |
| MDGA2 | 3.51059699 | |
| CST2 | 3.50592703 | |
| CSMD2 | 3.49268524 | |
| SH3GL3 | 3.49210734 | |
| LY86 | 3.48954956 | |
| ANKRD30B | 3.48758828 | |
| ITGB2 | 3.48062818 | |
| VEPH1 | 3.47384791 | |
| MMD | 3.46297023 | |
| BEND5 | 3.45545257 | |
| FGF13 | 3.4506228 | |
| HS6ST2 | 3.44502327 | |
| SLC39A8 | 3.43799657 | |
| MIR210 | 3.43554354 | |
| MPZL3 | 3.43166888 | |
| SNX10 | 3.43007866 | |
| CNTNAP3 | 3.43003244 | |
| MRAP2 | 3.42155469 | |
| ASTN1 | 3.41957925 | |
| CSNK2A3 | 3.39776573 | |
| FDCSP | 3.39037308 | |
| RGS7BP | 3.38512539 | |
| WNK3 | 3.37755438 | |
| CCR4 | 3.37561897 | mogamulizumab |
| GPNMB | 3.37425096 | glembatumumab vedotin |
| DNAJA4 | 3.37047154 | |
| AK4 | 3.36916685 | |
| SLC38A5 | 3.36524643 | |
| PRKCH | 3.36272718 | ingenol mebutate |
| CEACAM1 | 3.36008018 | |
| CFHR3 | 3.35612741 | |
| COLEC12 | 3.35486617 | |
| PPP1R9A | 3.35456188 | |
| SVEP1 | 3.34560616 | |
| PTGIS | 3.34483783 | phenylbutazone |
| SGCD | 3.34401877 | |
| DRD2 | 3.34271068 | paliperidone, risperidone, buspirone, carbidopa/entacapone/levodopa, bifeprunox, iloperidone, |

TABLE 1-continued

Fold Change in Kupffer Cells After BxPC-3-LiT Exosome Treatment

| Gene | logFC | Known Inhibitors |
|---|---|---|
| | | blonanserin, asenapine, pardoprunox, ocaperidone, abaperidone, methotrimeprazine, fluspirilene, SLV-314, cariprazine, rotigotine, acetophenazine, sultopride, zuclopenthixol, thioproperazine, lurasidone, opipramol, paliperidone palmitate, brexpiprazole, pipothiazine, carbidopa/levodopa, chloropromazine, domperidone, metoclopramide, sulpiride, meloxicam, amantadine, flupenthixol, chlorprothixene, trifluoperazine, fluphenazine, pimozide, clozapine, haloperidol, fluoxetine/olanzapine, fluphenazine decanoate, thiothixene, amitriptyline/perphenazine, haloperidol decanoate, molindone, trimethobenzamide, fluphenazine enanthate, loxapine, perphenazine, promazine, prochlorperazine, triflupromazine, quetiapine, pramipexole, olanzapine, remoxipride, lisuride, sertindole, cabergoline, ziprasidone, mesoridazine, thioridazine, aripiprazole, ropinirole, dihydroergocryptine, dihydroergotamine, bromocriptine, apomorphine, pergolide, dopamine, droperidol, thiethylperazine, droperidol/fentanyl, L-dopa |
| TMTC2 | 3.3382391 | |
| TFEC | 3.33747015 | |
| LCP2 | 3.33731863 | |
| SCGB3A2 | 3.33042971 | |
| DACH1 | 3.32238242 | |
| C1QTNF1 | 3.32212858 | |
| TMEM151A | 3.32188033 | |
| P2RY1 | 3.31905018 | clopidogrel/telmisartan, clopidogrel |
| GUCY1A2 | 3.31683434 | nitroglycerin, isosorbide-5-mononitrate, isosorbide dinitrate, nitroprusside |
| CHST15 | 3.30947518 | |
| APLN | 3.3058417 | |
| HOXD8 | 3.30346655 | |
| RASGEF1B | 3.30285326 | |
| ADAMTS3 | 3.30242146 | |
| SORBS2 | 3.29516461 | |
| IRAK3 | 3.2910969 | |
| GPR156 | 3.28879111 | |
| KRTAP2-3 | 3.28832421 | |
| GRM3 | 3.28776345 | fasoracetam |
| PTPRB | 3.28400334 | |
| SMOC1 | 3.28338272 | |
| JAM2 | 3.28215127 | |
| CCDC141 | 3.2740904 | |
| GPR34 | 3.26304326 | |
| LOC100506178 | 3.26249006 | |
| CASQ2 | 3.26109543 | |
| SLC16A6 | 3.2594469 | |
| NR4A3 | 3.25821865 | |
| EDNRB | 3.25158508 | bosentan, sitaxsentan, macitentan, atrasentan |
| GJA1 | 3.25131919 | |
| NAT2 | 3.25092115 | |
| AFP | 3.25029347 | |
| AQP9 | 3.24954593 | |
| ARHGDIG | 3.24671579 | |
| CD74 | 3.23681299 | milatuzumab |
| SCRG1 | 3.23040054 | |
| SAMD5 | 3.22825338 | |
| KCNE3 | 3.21161121 | |
| PLOD2 | 3.20525365 | |
| TMCC3 | 3.20273672 | |
| ADAMTSL1 | 3.20085438 | |
| TMEM150C | 3.19758218 | |
| PM20D1 | 3.19661918 | |
| MFAP2 | 3.19563126 | |
| LOC100506474 | 3.19345847 | |
| LIPH | 3.19021186 | |
| TNFRSF9 | 3.18341161 | urelumab |
| PCDHA6 | 3.17040429 | |
| MMP12 | 3.16706463 | UK 370106, MMP Inhibitor V, MMP-3 Inhibitor VIII, Actinonin, GM 6001, marimastat |
| AOAH | 3.16481181 | |
| DRD1 | 3.16154888 | carbidopa/entacapone/levodopa, iloperidone, asenapine, rotigotine, acetophenazine, zuclopenthixol, pipothiazine, carbidopa/levodopa, chloropromazine, flupenthixol, chlorprothixene, trifluoperazine, fluphenazine, pimozide, clozapine, haloperidol, fenoldopam, fluoxetine/olanzapine, fluphenazine decanoate, thiothixene, amitriptyline/perphenazine, haloperidol decanoate, trimethobenzamide, fluphenazine enanthate, periciazine, perphenazine, promazine, prochlorperazine, triflupromazine, |

TABLE 1-continued

Fold Change in Kupffer Cells After BxPC-3-LiT Exosome Treatment

| Gene | logFC | Known Inhibitors |
|---|---|---|
| | | quetiapine, pramipexole, olanzapine, lisuride, ziprasidone, mesoridazine, thioridazine, ropinirole, dihydroergocryptine, bromocriptine, methylergonovine, apomorphine, pergolide, dopamine, L-dopa |
| FFAR3 | 3.16052547 | |
| SBSPON | 3.15382837 | |
| LOC101055625 | 3.14926925 | |
| BMP6 | 3.14046975 | |
| CXADRP3 | 3.13525443 | |
| ADORA2B | 3.13515052 | adenosine, enprofylline, dyphylline, aspirin/butalbital/caffeine, acetaminophen/caffeine/dihydrocodeine, acetaminophen/aspirin/caffeine, caffeine/ergotamine, aspirin/caffeine/propoxyphene, aspirin/butalbital/caffeine/codeine, aspirin/caffeine/dihydrocodeine, acetaminophen/butalbital/caffeine, aminophylline, aspirin/caffeine/orphenadrine, acetaminophen/butalbital/caffeine/codeine, theophylline, caffeine, acetaminophen/caffeine/chlorpheniramine/hydrocodone/phenylephrine |
| SERPINB7 | 3.12734318 | |
| LIMCH1 | 3.12596952 | |
| MAGEL2 | 3.12506566 | |
| GABRB2 | 3.12318918 | methohexital, aspirin/butalbital/caffeine, aspirin/butalbital/caffeine/codeine, fospropofol, pagoclone, alphadolone, SEP 174559, nitrazepam, adinazolam, acetaminophen/butalbital/caffeine, sevoflurane, isoflurane, gaboxadol, isoniazid, felbamate, etomidate, muscimol, halothane, fluoxetine/olanzapine, amobarbital, estazolam, atropine/hyoscyamine/phenobarbital/scopolamine, acetaminophen/butalbital, eszopiclone, mephobarbital, hyoscyamine/phenobarbital, acetaminophen/butalbital/caffeine/codeine, butabarbital, diazepam, temazepam, zolpidem, lorazepam, olanzapine, triazolam, clonazepam, flurazepam, midazolam, oxazepam, zaleplon, secobarbital, butalbital, phenobarbital, pentobarbital, thiopental, propofol, ezogabine, desflurane, methoxyflurane, enflurane, pregnenolone |
| MS4A7 | 3.11656757 | |
| ABCA8 | 3.11419672 | |
| TPD52 | 3.11326728 | |
| MGC12916 | 3.10417985 | |
| GDF5 | 3.09611916 | |
| VASH2 | 3.09434492 | |
| TIE1 | 3.09248647 | |
| CNTFR | 3.0894093 | |
| C3 | 3.08448256 | |
| BMP2 | 3.08236675 | |
| SPON1 | 3.07655293 | |
| GRIN2B | 3.07528958 | dextromethorphan/morphine, neramexane, bicifadine, delucemine, nebostinel, besonprodil, UK-240455, tenocyclidine, dextromethorphan/quinidine, donepezil/memantine, ketamine, felbamate, ifenprodil, memantine, orphenadrine, cycloserine, N-(2-indanyl)glycinamide, dextromethorphan, brompheniramine/dextromethorphan/pseudoephedrine, chlorpheniramine/dextromethorphan/phenylephrine, carbinoxamine/dextromethorphan/pseudoephedrine, dextromethorphan/promethazine, 1-aminocyclopropane-1-carboxylic acid |
| BACH2 | 3.07351434 | |
| MYH10 | 3.07242023 | |
| PTPRD | 3.07000223 | |
| CDCP1 | 3.06147436 | |
| CD1D | 3.06133323 | |
| SULT4A1 | 3.05704363 | |
| HLA-DMB | 3.05501907 | |
| NCAM1 | 3.04897922 | BB-10901 |
| SLC9C2 | 3.04732055 | |
| SIRPB1 | 3.04629412 | |
| GRIN1 | 3.04463795 | dextromethorphan/morphine, neramexane, bicifadine, delucemine, nebostinel, besonprodil, UK-240455, dextromethorphan/quinidine, ketamine, felbamate, ifenprodil, memantine, orphenadrine, cycloserine, aspirin/caffeine/orphenadrine, N-(2-indanyl)glycinamide, dextromethorphan, acamprosate, brompheniramine/dextromethorphan/pseudoephedrine, chlorpheniramine/dextromethorphan/phenylephrine, carbinoxamine/dextromethorphan/pseudoephedrine, dextromethorphan/promethazine, agmatine, 1-aminocyclopropane-1-carboxylic acid |

TABLE 1-continued

Fold Change in Kupffer Cells After BxPC-3-LiT Exosome Treatment

| Gene | logFC | Known Inhibitors |
| --- | --- | --- |
| GJA4 | 3.03938292 | |
| ARC | 3.03519162 | |
| SPIN2A | 3.03084378 | |
| FREM1 | 3.02984215 | |
| RUNX3 | 3.02937735 | |
| FLRT2 | 3.02897711 | |
| NTF3 | 3.02509231 | |
| HIF1A-AS2 | 3.010595 | |
| SLC5A12 | 3.01022463 | |
| SDK1 | 3.00959591 | |
| LHX9 | 3.0081628 | |
| BTBD11 | 3.00423416 | |
| RAPGEF4 | 3.0035599 | |
| FAM124A | 2.99755889 | |
| KL | 2.99536688 | |
| STEAP2 | 2.99530645 | |
| WDR17 | 2.99486831 | |
| C5orf46 | 2.9935695 | |
| AADAC | 2.99252615 | |
| SLAMF7 | 2.98897182 | elotuzumab |
| SLIT2 | 2.98603301 | |
| PLCG2 | 2.98325593 | |
| PLN | 2.97623559 | |
| 3-Mar | 2.9750937 | |
| CYP26B1 | 2.97386132 | |
| HAS1 | 2.97147591 | |
| PKHD1L1 | 2.96943218 | |
| IL1R1 | 2.96564518 | anakinra |
| C10orf67 | 2.96539095 | |
| HOXD-AS2 | 2.96337274 | |
| ATF7IP2 | 2.96087386 | |
| DLGAP1 | 2.95153773 | |
| TTC9 | 2.95080058 | |
| ZPLD1 | 2.94971214 | |
| LOC100130539 | 2.94446372 | |
| PLEKHG1 | 2.9395061 | |
| KCTD4 | 2.93922664 | |
| IQCA1 | 2.93734118 | |
| CCND2 | 2.93722029 | |
| KIAA1598 | 2.92860418 | |
| LOC100130872 | 2.92634944 | |
| MFSD7 | 2.92137324 | |
| NCF2 | 2.90595346 | |
| TCERG1L | 2.90332717 | |
| LOC100132735 | 2.89772098 | |
| SERPINE1 | 2.89302646 | drotrecogin alfa |
| KAL1 | 2.89141696 | |
| WSCD1 | 2.8892966 | |
| MC5R | 2.88401868 | |
| KCNV2 | 2.88378608 | |
| GFPT2 | 2.88371698 | |
| LY75 | 2.8823198 | |
| TMEM156 | 2.88040936 | |
| PLD5 | 2.87663301 | |
| GLB1L2 | 2.87625492 | |
| ENO4 | 2.87331575 | |
| ADAMTSL2 | 2.86866912 | |
| TMEM217 | 2.86044505 | |
| PIK3CG | 2.85809804 | SF 1126, PX-866, PI3Kg inhibitor, dactolisib, pictilisib, buparlisib, XL147, PQR309, RP6530 |
| TIMP4 | 2.85160805 | |
| PLG | 2.84339606 | tenecteplase, PLAT, tranexamic acid, aprotinin, 6-aminocaproic acid, reteplase |
| TGFB2 | 2.84335996 | LY2109761, SB-505124 hydrochloride hydrate, TGF-β RI Kinase Inhibitor VIII, AEBSF hydrochloride, trabedersen, dalantercept |
| CYP7B1 | 2.84188095 | |
| TINAGL1 | 2.83208377 | |
| KIAA1199 | 2.83112258 | |
| CAMK2B | 2.82889154 | |
| CGREF1 | 2.82410233 | |
| GNAS-AS1 | 2.82394048 | |
| CXCL6 | 2.8230828 | |
| HPSE | 2.8216852 | 2-O,3-O-desulfated heparin, PG 545, SST 0001, heparanase inhibitor PI-88 |
| LXN | 2.81157871 | |
| CDA | 2.81108255 | E7727, cytidine deaminase inhibitor |

TABLE 1-continued

Fold Change in Kupffer Cells After BxPC-3-LiT Exosome Treatment

| Gene | logFC | Known Inhibitors |
|---|---|---|
| SHC2 | 2.80266161 | |
| FRMD4B | 2.79966824 | |
| SCN7A | 2.79504576 | riluzole |
| PTX3 | 2.79403415 | |
| ARHGAP25 | 2.79299269 | |
| IGFBP2 | 2.79071194 | |
| HPD | 2.78630877 | nitisinone |
| PPP1R14C | 2.78560365 | |
| PCSK5 | 2.78370788 | |
| GRIA3 | 2.78146522 | talampanel, farampator, LY451395, tezampanel |
| RASGEF1A | 2.7794693 | |
| C8orf47 | 2.77941424 | |
| LIF | 2.77065821 | |
| C12orf39 | 2.76791969 | |
| TBX15 | 2.76434547 | |
| SDS | 2.75584822 | |
| CPVL | 2.7548203 | |
| CD24 | 2.75130699 | |
| SLCO2B1 | 2.74958841 | |
| ZNF883 | 2.74722739 | |
| ABCA6 | 2.74577434 | |
| GPM6A | 2.74377086 | |
| HIVEP3 | 2.7437606 | |
| PRG4 | 2.73801452 | |
| TEX35 | 2.73723537 | |
| FCGR1B | 2.73410673 | IgG |
| ITGB3 | 2.73303221 | abciximab, TP 9201, cilengitide, tirofiban |
| JPH1 | 2.73018503 | |
| ACSL5 | 2.7274727 | Triacsin C, 2-Fluropalmicic acid, Triacsin C |
| HSPB3 | 2.72338924 | |
| PI15 | 2.72315045 | |
| ABCB1 | 2.72266883 | dofequidar, tariquidar, OC 144-093, valspodar |
| ESM1 | 2.72236768 | |
| TSPAN18 | 2.72177911 | |
| LAMA1 | 2.72149553 | |
| TCEAL6 | 2.72076683 | |
| CCR5 | 2.72056421 | maraviroc, vicriviroc, ancriviroc |
| RXFP1 | 2.71927829 | relaxin |
| FLI1-AS1 | 2.71718593 | |
| COL8A1 | 2.71317168 | collagenase clostridium histolyticum |
| CLEC14A | 2.7088991 | |
| RHOU | 2.70767082 | |
| GNA14 | 2.70706211 | |
| LOC643723 | 2.7051684 | |
| FCER1G | 2.70239703 | |
| BMPER | 2.69899229 | |
| TMEM74 | 2.69258478 | |
| SULT1B1 | 2.69198387 | |
| BNC1 | 2.68725563 | |
| PNMA2 | 2.68519208 | |
| ST6GALNAC5 | 2.68316611 | |
| PPFIA4 | 2.6822266 | |
| FGR | 2.68129353 | vemurafenib, cobimetinib/vemurafenib |
| P4HA3 | 2.68078465 | 1,4-DPCA, N-Oxalylglycine |
| TRABD2B | 2.68047951 | |
| LUM | 2.67467185 | |
| WWC1 | 2.66858131 | |
| GATA6 | 2.66044188 | |
| PCDHAC2 | 2.6564382 | |
| EFEMP1 | 2.65622762 | |
| SHOX2 | 2.65175467 | |
| MEIS3P1 | 2.64842824 | |
| ARHGEF35 | 2.64780363 | |
| IER3 | 2.64629923 | |
| AATK | 2.6455024 | |
| SERPINB2 | 2.64371366 | |
| LOC650368 | 2.64118376 | |
| PTPRO | 2.64075114 | |
| TSPAN11 | 2.63271538 | |
| SOX8 | 2.63089259 | |
| C1orf226 | 2.63004563 | |
| CECR1 | 2.62864332 | |
| BEX4 | 2.62535629 | |
| ZFP92 | 2.62522871 | |
| BDNF | 2.616826 | |
| ADARB1 | 2.61645 | |

TABLE 1-continued

Fold Change in Kupffer Cells After BxPC-3-LiT Exosome Treatment

| Gene | logFC | Known Inhibitors |
| --- | --- | --- |
| CCDC8 | 2.6154086 | |
| SUSD1 | 2.61503849 | |
| ZFPM2 | 2.61328664 | |
| MIR548AO | 2.60553976 | |
| EMILIN2 | 2.60428945 | |
| MIR210HG | 2.59904608 | |
| PIK3AP1 | 2.59850327 | |
| RAB17 | 2.59811319 | |
| C15orf48 | 2.59084883 | |
| GAL | 2.58956407 | |
| SH2D2A | 2.58943495 | Stat3 Inhibitor VIII, 5,15-DPP |
| TNFRSF8 | 2.58746477 | HeFi-1 monoclonal antibody, brentuximab vedotin |
| IL26 | 2.58666111 | |
| LOC401074 | 2.58491404 | |
| CD48 | 2.58465456 | |
| ANXA2P3 | 2.58391879 | |
| IGFL2 | 2.58368742 | |
| TCTEX1D1 | 2.58185896 | |
| LCP1 | 2.58056235 | |
| IL13RA2 | 2.5780017 | cintredekin besudotox |
| CDH5 | 2.5760366 | |
| TNFRSF10C | 2.57104273 | |
| C6 | 2.57095638 | |
| MYOT | 2.56864625 | |
| OR51B5 | 2.56196946 | |
| CD93 | 2.56125837 | |
| GPRC5B | 2.55885965 | |
| GUCY1A3 | 2.55118389 | nitroglycerin, isosorbide-5-mononitrate, isosorbide dinitrate, nitroprusside |
| HS3ST3B1 | 2.55090838 | |
| CREB5 | 2.55060013 | |
| DOCK8 | 2.55002744 | |
| STK32A | 2.54946495 | |
| MAF | 2.54826026 | |
| SLC2A9 | 2.54810265 | |
| IL1RL2 | 2.54785222 | |
| LOC255167 | 2.54722239 | |
| LMO2 | 2.54500606 | http://www.genecards.org/cgi-bin/carddisp.pl?gene=LMO2&keywords=LMO2#drugs_compounds |
| CECR2 | 2.54307861 | |
| TAF7L | 2.54264025 | |
| LRRC43 | 2.53536578 | |
| PCDHA3 | 2.53197972 | http://www.genecards.org/cgi-bin/carddisp.pl?gene=PCDHA3&keywords=PCDHA3#drugs_compounds |
| CD38 | 2.5275039 | daratumumab |
| PCDHB3 | 2.52694083 | http://www.genecards.org/cgi-bin/carddisp.pl?gene=PCDHB3&keywords=PCDHB3#drugs_compounds |
| PLVAP | 2.52503582 | |
| RHOD | 2.52320214 | http://www.genecards.org/cgi-bin/carddisp.pl?gene=RHOD&keywords=RHOD#drugs_compounds |
| LEP | 2.51555938 | http://www.genecards.org/cgi-bin/carddisp.pl?gene=LEP&keywords=LEP#drugs_compounds |
| IGSF3 | 2.51529251 | |
| MAB21L1 | 2.50920945 | |
| NMU | 2.50908554 | http://www.genecards.org/cgi-bin/carddisp.pl?gene=NMU&keywords=NMU#drugs_compounds |
| CDH2 | 2.50675045 | N-ac-CHAVC-NH2 |
| GPRC5A | 2.50306061 | |
| ENPP6 | 2.50227396 | |
| PDIA5 | 2.49829958 | |
| MYCT1 | 2.49800448 | |
| CD70 | 2.49708626 | |
| CCL26 | 2.48932305 | |
| RAPGEF5 | 2.48817176 | http://www.genecards.org/cgi-bin/carddisp.pl?gene=RAPGEF5&keywords=RAPGEF5#drugs_compounds |
| LOC100507410 | 2.48573734 | |
| ANKRD20A5P | 2.47906981 | |
| GRIN2D | 2.47800624 | dextromethorphan/morphine, neramexane, bicifadine, delucemine, nebostinel, besonprodil, UK-240455, dextromethorphan/quinidine, ketamine, felbamate, memantine, orphenadrine, cycloserine, aspirin/caffeine/orphenadrine, N-(2-indanyl)glycinamide, dextromethorphan, brompheniramine/dextromethorphan/pseudoephedrine, chlorpheniramine/dextromethorphan/phenylephrine, carbinoxamine/dextromethorphan/pseudoephedrine, dextromethorphan/promethazine, 1-aminocyclopropane-1-carboxylic acid |
| ITM2A | 2.47568721 | |
| ST14 | 2.47280067 | |
| VWDE | 2.46925943 | |
| PROM1 | 2.46804185 | |
| DES | 2.4666673 | |
| EPDR1 | 2.46135644 | |

TABLE 1-continued

Fold Change in Kupffer Cells After BxPC-3-LiT Exosome Treatment

| Gene | logFC | Known Inhibitors |
| --- | --- | --- |
| KIAA1211 | 2.46066719 | |
| SERTAD4-AS1 | 2.4581364 | |
| IGFBP1 | 2.45698876 | NBI-31772 |
| PCDHA7 | 2.456305 | |
| SYT12 | 2.4548913 | |
| ANKRD29 | 2.45278495 | |
| FOXP2 | 2.4499574 | |
| NAMPT | 2.44845719 | |
| LOC645638 | 2.44565474 | |
| MYH14 | 2.44275583 | |
| ASS1 | 2.44211069 | |
| B4GALT1 | 2.44154514 | |
| CCL2 | 2.44060123 | mimosine |
| ZNF676 | 2.44013013 | |
| OGN | 2.43473582 | |
| SOCS1 | 2.43307064 | |
| ELOVL3 | 2.43264859 | |
| RARB | 2.43123758 | etretinate, daunorubicin/tretinoin, idarubicin/tretinoin, doxorubicin/tretinoin, adapalene, isotretinoin, tazarotene, acitretin, tretinoin, tamibarotene, alitretinoin, fenretinide |
| ARMC4 | 2.43061099 | |
| MFI2 | 2.42789795 | |
| FLJ16779 | 2.42552454 | |
| ASB9 | 2.42318876 | |
| FLJ42289 | 2.4219351 | |
| PRLR | 2.41856648 | fluoxymesterone |
| DGAT2 | 2.41239778 | omacor |
| SLAMF9 | 2.41227538 | |
| ADAM21 | 2.41225514 | |
| LRRC4B | 2.41102205 | |
| IP6K3 | 2.40742904 | |
| PCBP3 | 2.40133141 | |
| CA13 | 2.40133088 | methazolamide, hydrochlorothiazide, acetazolamide, trichloromethiazide, chlorothiazide, chlorthalidone, benzthiazide, sulfacetamide, topiramate |
| GLB1L | 2.40022375 | |
| MT1A | 2.40007882 | |
| ADRA1B | 2.38952982 | paliperidone, risperidone, antazoline/naphazoline, acetaminophen/clemastine/pseudoephedrine, articaine/epinephrine, bupivacaine/epinephrine, caffeine/ergotamine, acetaminophen/dexbrompheniramine/pseudoephedrine, dapiprazole, dexbrompheniramine/pseudoephedrine, chlorpheniramine/ibuprofen/pseudoephedrine, dipivefrin, cetirizine/pseudoephedrine, asenapine, epinephrine/prilocaine, epinephrine/lidocaine, DL 017, myogane, UK-294315, thioproperazine, dextromethorphan/quinidine, ibuprofen/phenylephrine, dutasteride/tamsulosin, hydrocodone/pseudoephedrine, paliperidone palmitate, chlorpheniramine/ibuprofen/phenylephrine, brexpiprazole, brimonidine/brinzolamide, epinephrine/methotrexate, fexofenadine/pseudoephedrine, cyclopentolate/phenylephrine, loratadine/pseudoephedrine, terazosine, chloropromazine, prazosin, doxazosin, methoxamine, carvedilol, phenylpropanolamine, ephedrine, tolazoline, guanethidine, phenoxybenzamine, brimonidine, clonidine, cirazoline, alfuzosin, quinidine, polythiazide/prazosin, fluoxetine/olanzapine, guanadrel, chlorpheniramine/methscopolamine/phenylephrine, metaraminol, epinastine, quetiapine, D-pseudoephedrine, apraclonidine, olanzapine, tamsulosin, nefazodone, venlafaxine, phenylephrine, phentolamine, labetalol, mephentermine, ziprasidone, propylhexedrine, thioridazine, aripiprazole, midodrine, dihydroergotamine, ergotamine, norepinephrine, alpha-methyl dopa, epinephrine, dobutamine, droxidopa, dopamine, arbutamine, chlorpheniramine/phenylpropanolamine, desloratadine/pseudoephedrine, phenylephrine/pyrilamine, chlorpheniramine/hydrocodone/phenylephrine, acrivastine/pseudoephedrine, chlorpheniramine/phenylephrine/pyrilamine, carbinoxamine/pseudoephedrine, hydrocodone/phenylephrine/pyrilamine, acetaminophen/caffeine/chlorpheniramine/hydrocodone/phenylephrine, brompheniramine/codeine/phenylpropanolamine, pseudoephedrine/triprolidine, chlorpheniramine/phenylephrine/phenyltoloxamine, codeine/pseudoephedrine/triprolidine, |

TABLE 1-continued

Fold Change in Kupffer Cells After BxPC-3-LiT Exosome Treatment

| Gene | logFC | Known Inhibitors |
|---|---|---|
| | | brompheniramine/dextromethorphan/pseudoephedrine, codeine/phenylephrine/promethazine, chlorpheniramine/dextromethorphan/phenylephrine, diphenhydramine/phenylephrine, chlorpheniramine/hydrocodone/pseudoephedrine, azatadine/pseudoephedrine, naphazoline, carbinoxamine/dextromethorphan/pseudoephedrine, phenylephrine/promethazine |
| TMEM154 | 2.38653047 | |
| P2RX5 | 2.38537519 | |
| VTN | 2.38509927 | |
| CCDC110 | 2.38409376 | |
| PCDHGA12 | 2.38408642 | |
| SCG5 | 2.37959814 | |
| DDX43 | 2.37819021 | |
| F2RL3 | 2.37333612 | |
| ISL1 | 2.37097157 | |
| C1orf114 | 2.3682333 | |
| ITGAM | 2.36809938 | |
| ABCD2 | 2.36795412 | |
| GPR143 | 2.36787546 | |
| TTC3P1 | 2.36770181 | |
| THY1 | 2.36721471 | |
| SPINT2 | 2.36516966 | |
| IRF5 | 2.36484938 | |
| CCDC160 | 2.36404356 | |
| ZFHX4-AS1 | 2.35999578 | |
| PCDHAC1 | 2.35799336 | |
| COL24A1 | 2.35762344 | collagenase clostridium histolyticum |
| PNMAL2 | 2.3518041 | |
| SNORD18A | 2.35019109 | |
| SIGLEC9 | 2.34985948 | |
| ATP10B | 2.34857539 | |
| PDZK1IP1 | 2.34765513 | |
| FAM84B | 2.3462768 | |
| CYP4X1 | 2.34361302 | |
| RAI14 | 2.34227332 | |
| CPZ | 2.3348015 | |
| TNFRSF10A | 2.33011253 | trm-1 |
| SPON2 | 2.32902632 | |
| MIR21 | 2.32708664 | |
| TCEAL7 | 2.32387961 | |
| H19 | 2.3203507 | |
| UCHL1 | 2.31773893 | WP1130, BML-282, UCH-L1 Inhibitor, Ubiquitin Aldehyde |
| CDKL2 | 2.30745239 | |
| KCNMB4 | 2.30594345 | tedisamil |
| CTGF | 2.30487482 | FG-3019 |
| SYN2 | 2.30071712 | |
| OCIAD2 | 2.29612038 | |
| CLIC3 | 2.29416105 | |
| RASSF9 | 2.29371947 | |
| PDE7B | 2.29253238 | dyphylline, nitroglycerin, aminophylline, anagrelide, milrinone, dipyridamole, ketotifen, tolbutamide, theophylline, pentoxifylline |
| EDA | 2.28668261 | |
| LOC401010 | 2.28388483 | |
| IGSF5 | 2.28202885 | |
| EGF | 2.28070622 | WZ 3146, BIBU 1361 dihydrochloride, Gefitinib 2hydrochloride salt, BPIQ-I, Tyrphostin AG 528, Tyrphostin 47, BPDQ, LFM-A12, ARRY334543, AST 1306, EGFR Inhibitor, EGFR Inhibitor III, Pelitinib, BIBX 1382, PD 153035 Hydrochloride, Desmethyl Erlotinib Acetate, BPIQ-II HCl Salt, Tyrphostin RG 14620, AG 556, AG 555, Tyrphostin AG 183, Lavendustin C methyl ester, HDS 029, Tyrphostin B44, WZ 4002, (+)-Aeroplysinin-1, AG 43, XL647, AZD8931, Tyrphostin AG 112, AG 494, Tyrphostin 47, Butein, PD 174265, Afatinib, PD 168393, Erbstatin Analog, CL-387, 785, Tyrphostin AG 1478, Gefitinib, Erlotinib Hydrochloride, Reveromycin A, Suramin sodium |
| CSTA | 2.27610175 | |
| SNORD75 | 2.27240008 | |
| ANKRD2 | 2.27212432 | |
| GPR158 | 2.27158934 | |
| SLA | 2.27059193 | |
| LOC100506688 | 2.26402616 | |
| EMB | 2.26331018 | |
| GSG1 | 2.25985308 | |

TABLE 1-continued

Fold Change in Kupffer Cells After BxPC-3-LiT Exosome Treatment

| Gene | logFC | Known Inhibitors |
| --- | --- | --- |
| TGFBR1 | 2.25884976 | A 83-01, SB 431542, Casein Kinase I Inhibitor, D4476, TGF-β RI Kinase Inhibitor V, LY 364947, TGF-β RI Kinase Inhibitor VII, TGF-β RI Kinase Inhibitor III, ALK5 Inhibitor II, LY2157299, SB-505124 hydrochloride hydrate, TGF-β RI Kinase Inhibitor VIII, galunisertib, TEW-7197 |
| CHI3L1 | 2.25705123 | |
| FLJ46906 | 2.25438794 | |
| ASPHD1 | 2.25391036 | |
| CPA4 | 2.2533117 | |
| CCNA1 | 2.25283866 | |
| VAMP8 | 2.24709746 | |
| FBXO41 | 2.24694378 | |
| ZNF117 | 2.2456487 | |
| XPNPEP2 | 2.24319653 | |
| MIR4635 | 2.23484294 | |
| HLA-DOA | 2.23183189 | |
| C3orf55 | 2.22936692 | |
| PAPPA | 2.22401783 | |
| NDRG2 | 2.22392543 | |
| ADCY7 | 2.22219102 | |
| MFAP5 | 2.21698554 | |
| HAS2 | 2.21686577 | |
| FAM189A2 | 2.21138849 | |
| TSPAN33 | 2.21042488 | |
| GALNT18 | 2.20567472 | |
| TNNT2 | 2.20469192 | |
| NCALD | 2.20210796 | |
| MCHR1 | 2.20083458 | SB 568849 |
| FAM19A5 | 2.19874912 | |
| PCDHGA7 | 2.19851521 | |
| PARP15 | 2.19687415 | |
| KCNJ2 | 2.19293991 | nicorandil, amiodarone |
| FHIT | 2.19235121 | |
| ALDH1B1 | 2.19223592 | |
| LINC00312 | 2.18798964 | |
| LOX | 2.18706624 | |
| TGFB3 | 2.18659131 | LY2109761, SB-505124 hydrochloride hydrate, TGF-β RI Kinase Inhibitor VIII |
| ANKRD7 | 2.17857737 | |
| TNS4 | 2.17369872 | |
| IL32 | 2.17243218 | |
| LOC387895 | 2.17211172 | |
| DAB1 | 2.1713596 | |
| LRMP | 2.17070139 | |
| FABP4 | 2.17035718 | |
| LOC643387 | 2.1694829 | |
| FGL2 | 2.16882284 | |
| FNBP1L | 2.16663267 | |
| AKAP12 | 2.16257599 | |
| CABP1 | 2.15838386 | |
| P4HA1 | 2.1575579 | 1,4-DPCA, N-Oxalylglycine |
| SOX9 | 2.14867184 | |
| ACTG2 | 2.14828332 | |
| C5orf63 | 2.14778246 | |
| CYP1A1 | 2.14517934 | Elipticine, TMS, Alizarin, Rutaecarpine, Pterostibene, Pterocartus marsupium, a-Naphthoflavone, Rhapontigenin |
| C22orf15 | 2.14507232 | |
| SDK2 | 2.13592534 | |
| LRRC17 | 2.13340715 | |
| TREML3P | 2.13000503 | |
| RSPH1 | 2.12565699 | |
| LOC400043 | 2.12142299 | |
| FZD9 | 2.12005159 | |
| TDRD6 | 2.1181766 | |
| RASL10B | 2.11813738 | |
| PDGFD | 2.10935508 | 4-Dechloro-2-chloro-regorafenib, Nilvadipine, Sennoside B, 4-Chloro-6,7-bis-(2-methoxy-ethoxy)-quinazoline, Suramin sodium |
| PIFO | 2.10907594 | |
| KRT32 | 2.10504378 | |
| TSTD1 | 2.10303314 | |
| AMPH | 2.09992181 | |
| SLC35F2 | 2.09739412 | |
| KCNJ12 | 2.09694128 | Dofetilide, nicorandil, amiodarone |
| PTPRR | 2.09005077 | |
| WNK4 | 2.08862932 | |
| ATP5EP2 | 2.0870376 | |
| TNFRSF11A | 2.0815448 | |

TABLE 1-continued

Fold Change in Kupffer Cells After BxPC-3-LiT Exosome Treatment

| Gene | logFC | Known Inhibitors |
| --- | --- | --- |
| MAFB | 2.07510702 | |
| STXBP6 | 2.07234504 | |
| MFSD2A | 2.06780228 | |
| LOC728819 | 2.06745352 | |
| NOS1AP | 2.06721081 | |
| LOC100507156 | 2.06662425 | |
| WISP1 | 2.0661336 | |
| ZCCHC5 | 2.06593324 | |
| PTPN22 | 2.06418823 | |
| MMP16 | 2.06369656 | MMP Inhibitor V, marimastat |
| LCNL1 | 2.06357595 | |
| RBP4 | 2.06319664 | |
| ZNF750 | 2.06301977 | |
| RNF212 | 2.06255146 | |
| EGR2 | 2.06023904 | |
| ADCY5 | 2.05635899 | |
| PLEKHH2 | 2.04789266 | |
| BAI1 | 2.04213241 | |
| TLE3 | 2.03549548 | |
| VEGFA | 2.02937818 | dalteparin, bevacizumab, ranibizumab, aflibercept, bevacizumab/erlotinib, bevacizumab/sorafenib, bevacizumab/5-fluorouracil, bevacizumab/temozolomide, bevacizumab/irinotecan, bevacizumab/carmustine/lomustine, bevacizumab/paclitaxel, bevacizumab/irinotecan/oxaliplatin, aflibercept/irinotecan, bevacizumab/capecitabine/oxaliplatin, bevacizumab/panitumumab, bevacizumab/cetuximab, bevacizumab/pemetrexed, bevacizumab/gemcitabine, bevacizumab/capecitabine/irinotecan/oxaliplatin, bevacizumab/capecitabine, bevacizumab/paclitaxel/topotecan, bevacizumab/oxaliplatin, bevacizumab/docetaxel, bevacizumab/doxorubicin/paclitaxel, pegaptanib |
| FAM60A | 2.02865297 | |
| CNTNAP3B | 2.02620589 | |
| KCNJ15 | 2.01683974 | |
| PTPRF | 2.01645645 | |
| LINC00839 | 2.01354308 | |
| ATP6V0D2 | 2.01341371 | |
| KIT | 2.01257944 | nilotinib, dasatinib, sunitinib, pazopanib, lenvatinib, tivozanib, motesanib, OSI-930, telatinib, tandutinib, cabozantinib, quizartinib, regorafenib, flumatinib, ponatinib, bortezomib/sorafenib, lapatinib/pazopanib, dexamethasone/lenalidomide/sorafenib, bevacizumab/sorafenib, imatinib/sirolimus, PLX3397, cabozantinib/edotinib, famitinib, imatinib/nilotinib/pegintron, cytarabine/idarubicin/sorafenib, 5-azacytidine/sorafenib, decitabine/sorafenib, LOP628, MGCD516, AKN-028, chiauranib, everolimus/sorafenib, imatinib, sorafenib |
| RGS17 | 2.01002051 | |
| ABHD12B | 2.00963294 | |
| FBLN1 | 2.00822851 | |
| DUSP8 | 2.00802724 | |
| MARCKSL1 | 2.00671599 | |
| ABCA9 | 2.0027657 | |
| FCN3 | 2.00088005 | |

Another aspect of the present invention relates to a method of managing treatment of a subject having cancer. This method involves selecting a subject undergoing treatment for cancer and obtaining, from the selected subject, a sample containing S100 molecules. Higher or lower levels or the presence or absence of one or more S100 molecules expressed in tissue is then detected, and treatment is modified, as necessary, based on the detecting step.

Other suitable methods and modes of detection are substantially the same materials and methods described above.

In one embodiment, detection of S100A4, S100A6, S100A10, S100A11, S100A13, and/or S100A16 indicates that said treatment should be modified, as necessary, to treat or prevent lung metastasis.

In another embodiment, detection of S100A8, S100A9 and/or S100P indicates that said treatment should be modified, as necessary, to treat or prevent liver metastasis.

In a further embodiment, detection of S100A8, S100A9, S100P, S100A4, S100A6, S100A10, S100A11, S100A13, and/or S100A16 indicates that said treatment should be modified, as necessary, to treat or prevent cancer recurrence or metastasis.

Other suitable proteins for detection are substantially the same as those in Table 1 above.

Another aspect of the present invention is directed to a kit suitable for determining whether a cancer is likely to metastasize to the lung. This kit includes one or more reagents suitable for detecting expression levels of S100A4, S100A6, S100A10, S100A11, S100A13, and S100A16. The reagents comprise: (1) oligonucleotide primers suitable for detecting expression levels of S100A4, S100A6, S100A10, S100A11, S100A13, and S100A16 using a qualitative polymerase chain reaction; (2) oligonucleotide probes suitable for detecting expression levels of S100A4, S100A6, S100A10, S100A11, S100A13, and S100A16 using a hybridization assay; or (3) antibodies or binding fragments suitable for detecting expression levels of S100A4, S100A6, S100A10, S100A11, S100A13, and S100A16 using an immunoassay.

In a further embodiment, the kit also includes one or more reagents suitable for detecting expression levels of proteins selected from the group consisting of ITG$\alpha_1$, ITG$\alpha_2$, ITG$\alpha_{2b}$, ITG$\alpha_3$, ITG$\alpha_4$, ITG$\alpha_5$, ITG$\alpha_6$, ITG$\alpha_{11}$, ITG$\alpha_v$, ITG$\beta_1$, ITG$\beta_3$, ITG$\beta_4$, ITG$\beta_5$, ITG$\beta_6$, clotting factors, fibronectin, and laminin.

Other materials and methods suitable for use in conjunction with this kit are substantially the same as those described above.

A further aspect of the present invention is directed to a kit suitable for determining whether a cancer is likely to metastasize to the liver. This kit includes one or more reagents suitable for detecting expression levels of S100A8, S100A9 and S100P. The reagents comprise: (1) oligonucleotide primers suitable for detecting expression levels of S100A8, S100A9 and S100P using a qualitative polymerase chain reaction; (2) oligonucleotide probes suitable for detecting expression levels of S100A8, S100A9 and S100P using a hybridization assay; or (3) antibodies or binding fragments suitable for detecting expression levels of S100A8, S100A9 and S100P using an immunoassay.

In a further embodiment, the kit also includes one or more reagents suitable for detecting expression levels of proteins selected from the group consisting of ITG$\alpha_1$, ITG$\alpha_2$, ITG$\alpha_{2b}$, ITG$\alpha_3$, ITG$\alpha_4$, ITG$\alpha_5$, ITG$\alpha_6$, ITG$\alpha_{11}$, ITG$\alpha_v$, ITG$\beta_1$, ITG$\beta_3$, ITG$\beta_4$, ITG$\beta_5$, ITG$\beta_6$, clotting factors, fibronectin, and laminin.

Other materials and methods suitable for use in conjunction with this kit are substantially the same as those described above.

Another aspect of the present invention is directed to a kit suitable for detecting whether a cancer is likely to metastasize to the liver, the lung, and the brain. This kit includes one or more one or more reagents suitable for detecting expression levels of ITG$\alpha_v$ and ITG$\beta_5$, one or more reagents suitable for detecting expression levels of ITG$\alpha_6$, ITG$\beta_1$, and ITG$\beta_4$, and one or more reagents suitable for detecting expression levels of ITG$\alpha_v$ and ITG$\beta_3$.

In one embodiment, the kits contain one or more reagents suitable for isolating cancer exosomes. An exemplary reagent includes, but is not limited to, a reagent suitable for detecting the expression level of ITG$\beta_1$, ITG$\alpha_3$, ITG$\alpha_3$, Calreticulin (CALR), Coagulation factor V, Nidogen-1 (NID1), and Fibrinogen-like protein 1 on exosomes.

In another embodiment, the kits contain one or more reagents suitable for isolating all exosomes. Exemplary reagents include, but are not limited to, reagents suitable for detecting the expression of CD63, CD9, Alix, β-actin, S100A6, Fibulin-1 (FBLN1), Coagulation factor X, Collagen alpha-2(VI) chain (COL6A2), Protocadherin Fat 4 (FAT4), Protocadherin Fat 1 (FAT1), and Fibrinogen beta chain on exosomes.

In a further embodiment, the kit includes one or more reagents suitable for detecting expression levels of proteins selected from the group consisting of clotting factors, fibronectin, and laminin.

Other materials and methods suitable for use in conjunction with this kit are substantially the same as those described above.

EXAMPLES

The following examples are provided to illustrate embodiments of the present invention but they are by no means intended to limit its scope.

Materials and Methods

Cell Lines and Cell Culture.

The cell lines used in this study were kindly provided as follows: human breast cancer MDA-MB-231 organotropic lines 4175, 1833, and 831 by Dr. Joan Massague (Memorial Sloan Kettering Cancer Center (MSKCC), New York, NY, USA); human breast cancer 4173 and 4180 cells by Dr. Andy Minn (Abramson Family Cancer Research Institute, Philadelphia, PA, USA); human breast cancer 231BR cells by Dr. Patricia Steeg (National Cancer Institute, Bethesda, MD, USA); liver metastasis enriched uveal melanoma cells by Dr. Vinagolu Raj asekhar (MSKCC); human osteosarcoma 143B cells by Dr. Aru Narendran (Southern Alberta Cancer Research Institute, Calgary, AB, Canada); human melanoma 131/4-5B2 and 131/8-2L cells by Dr. Robert Kerbel (Sunnybrook Health Sciences Centre, Toronto, ON, Canada); human melanoma SB1B cells by Dr. Claire F. Verschraegen (University of Vermont, Burlington, VT); human rhabdomyosarcoma CT10 and RD cells by from Dr. Rebecca Gladdy (Lunenfeld-Tanenbaum Research Institute, Toronto, ON, Canada); and human Wilms' tumour CCG9911 and CLS1 cells by Dr. Alex Ketsis (MSKCC). Human breast cancer cell lines MDA-MB-231 and MDA-MB-468, human breast epithelial cells MCF10A, human pancreatic cancer cell lines, gastric cancer cell lines, and colorectal cancer cell lines were purchased from American Type Culture Collection (ATCC) (Manassas, VA, USA). Although HT29 is commonly misidentified, this cell line was purchased directly from ATCC and certified by this repository. The C57BL/6 murine pancreatic adenocarcinoma PANO2 was purchased from the National Cancer Institute Tumour Repository (DTP/DCTD, Frederick National Laboratory for Cancer Research, Frederick, MD, USA). For in vitro education of human lung fibroblasts WI-38 (ATCC), human bronchial epithelial cells HBEpC (PromoCell), and human Kupffer cells (Life Technologies, Carlsbad, CA, USA), cells were maintained in culture for 14 days, with media containing 0, 5, or 10 µg/ml of exosomes, replenished every other day. Kupffer cells were cultured in RPMI and WI-38 cells were cultured in alpha-MEM, both supplemented with 10% exosome-depleted fetal bovine serum (FBS) (Gibco, Thermo Fisher Scientific, Waltham, MA, USA) and penicillin-streptomycin. HBEpC cells were cultured in airway epithelial cell growth medium (PromoCell). All cells were maintained in a humidified incubator with 5% $CO_2$ at 37° C. FBS was depleted of bovine exosomes by ultracentrifugation at 100,000×g for 70 minutes. All cells lines were routinely tested for *mycoplasma* and were found to be negative.

Exosome Purification, Characterization, and Analyses.

Exosomes were purified by sequential centrifugation as previously described (Peinado et al., "Melanoma Exosomes Educate Bone Marrow Progenitor Cells Toward a Pro-Metastatic Phenotype Through MET," Nat. Med. 18:883-891 (2012), which is hereby incorporated by reference in its entirety). Briefly, cells were removed from three to four day cell culture supernatant by centrifugation at 500×g for 10 minutes to remove any cell contamination. To remove any possible apoptotic bodies and large cell debris, the supernatants were then spun at 12,000×g for 20 minutes. Finally, exosomes were harvested by spinning at 100,000×g for 70 minutes. Exosomes were washed in 20 ml of phosphate-buffered saline (PBS) and pelleted again by ultracentrifugation (Beckman 70Ti rotor). Exosome preparations were verified by electron microscopy. Exosome size and particle number were analyzed using the LM10 or DS500 nanoparticle characterization system (NanoSight, Malvern Instruments, Malvern, Worcestershire, United Kingdom) equipped with a blue laser (405 nm). Normal pancreatic tissue and mammary fat pad tissue-derived exosomes were obtained by culturing 5 pancreata or mammary fat pads isolated from healthy 4-6 week-old C57BL/6 mice in 3 ml of FBS-free RPMI for 12 hours. The final exosome pellet was resuspended in PBS and protein concentration was measured by BCA (Pierce™, Thermo Fisher Scientific).

Proteomics Analysis.

Mass spectrometry analyses of exosomes were performed at the Rockefeller University Proteomics Resource Center using 20 µg of exosomal protein. Samples were denatured using 8M urea, reduced using 10 mM DTT, and alkylated using 100 mM iodoacetamide. This was followed by proteolytic digestion with endoproteinase LysC (Wako Chemicals, Richmond, VA, USA) overnight at room temperature, and subsequent digestion with trypsin (Promega, Madison, WI, USA) for 5 hours at 37° C. The digestion was quenched with formic acid and resulting peptide mixtures were desalted using in-house made C18 Empore (3M) StAGE tips (Rappsilber et al., "Stop and Go Extraction Tips for Matrix-Assisted Laser Desorption/Ionization, Nanoelectrospray, and LC/MS Sample Pretreatment in Proteomics," *Anal. Chem.* 75:663-670 (2003), which is hereby incorporated by reference in its entirety). Samples were dried and solubilized in the sample loading buffer containing 2% acetonitrile and 2% formic acid. Approximately 3-5 µg of each sample were analysed by reversed phase nano-LC-MS/MS (Ultimate 3000 coupled to QExactive, Thermo Scientific). Following loading onto the C18 trap column (5 µm beads, Thermo Scientific) at a flow rate of 3 µl/min, peptides were separated using a 75 µm inner diameter C18 column (3 µm beads, Nikkyo Technos Co., Japan) at a flow rate of 200 nl/min, with a gradient increasing from 5% Buffer B (0.1% formic acid in acetonitrile)/95% Buffer A (0.1% formic acid) to 40% Buffer B/60% Buffer A, over 140 minutes. All LC-MS/MS experiments were performed in data dependent mode. Precursor mass spectra were recorded in a 300-1400 m/z mass range at 70,000 resolution, and 17,500 resolution for fragment ions (lowest mass: m/z 100). Data were recorded in profile mode. Up to twenty precursors per cycle were selected for fragmentation and dynamic exclusion was set to 45 seconds. Normalized collision energy was set to 27.

Semi-quantitative data analysis: MS/MS spectra were extracted and searched against Uniprot complete Human or Mouse proteome databases (January 2013) concatenated with common contaminants (Bunkenborg et al., "The Minotaur Proteome: Avoiding Cross-Species Identifications Deriving From Bovine Serum in Cell Culture Models," *Proteomics* 10:3040-3044 (2010), which is hereby incorporated by reference in its entirety) using Proteome Discoverer 1.4 (Thermo Scientific) and Mascot 2.4 (Matrix Science). All cysteines were considered alkylated with acetamide. N-terminal glutamate to pyroglutamate conversion, oxidation of methionine, and protein N-terminal acetylation were allowed as variable modifications. Data were first searched using fully tryptic constraints. Matched peptides were filtered using a Percolator (Kali et al., "Semi-Supervised Learning for Peptide Identification from Shotgun Proteomics Datasets," *Nat. Methods* 4:923-925 (2007), which is hereby incorporated by reference in its entirety) based 1% false discovery rate. Spectra not being matched at a false discovery rate of 1% or better were re-searched allowing for semi-tryptic peptides. The average area of the three most abundant peptides for a matched protein (Silva et al., "Absolute Quantification of Proteins by LCMSE: a Virtue of Parallel MS Acquisition," *Mol. Cell Proteomics* 5:144-156 (2006), which is hereby incorporated by reference in its entirety) was used to gauge protein amounts within and between samples.

Label-Free Quantitative Mass Spectrometry: LC-MS/MS data from three technical replicates of six organ-tropic samples were analysed using MaxQuant (version 1.5.0.30) and Perseus software (version 1.5.0.9) (Cox et al., "Accurate Proteome-Wide Label-Free Quantification by Delayed Normalization and Maximial Peptide Ratio Extraction, Termed MaxLFQ," *Mol. Cell Proteomics* 13:2513-2526 (2014), which is hereby incorporated by reference in its entirety), searching against a Uniprot human database (July 2014). Oxidation of methionine and protein N-terminal acetylation were allowed as variable modifications, and cysteine carbamidomethyl was set as a fixed modification. Two missed cleavages were allowed for specificity: Trypsin/P. The "match between runs" option was enabled. False discovery rates at the protein and peptide level were set to 1%. Protein abundance is expressed as LFQ (label-free quantitation) values. Only proteins quantified in at least two out of three replicates in at least one group were retained, and missing values were imputed. A multiple sample ANOVA test was performed and corrected for multiple hypotheses testing using a permutation-based FDR threshold of 0.05.

Exosome Treatment and Labeling.

To assess lung, liver and bone exosome distribution, exosomes were injected via the retro-orbital venous sinus, the tail vein or intracardially. Exosome distribution patterns were consistent regardless of the route of injection. For brain distribution, exosomes were only observed in the brain following intra-cardiac injection. For 24 hour exosome treatments, 10 µg of total exosomal protein were injected via the retro-orbital venous sinus, the tail vein, or intracardially in a total volume of 1000 PBS. For exosome-tracking purposes, purified exosomes were fluorescently labelled using PKH67 or PKH26 membrane dye (Sigma-Aldrich, St. Louis, MO, USA) or FM1-43FX dye (Life Technologies) for the photo conversion experiment. Labelled exosomes were washed in 20 ml of PBS, collected by ultracentrifugation and resuspended in PBS. When performing peptide blocking experiments, exosomes were incubated with 0.06 µM of RGD or HYD-1 (peptide sequence: KIKMVISWKG (SEQ ID NO: 1)) peptides for 30 minutes at 37° C. prior to exosome injection. An average of five random fields was counted per sample at 20× magnification and representative pictures were taken at 40× magnification. For education experiments, mice received 10 µg of exosomes retro-orbitally every other day for three weeks. To measure exosome uptake by specific cell types, labelled exosomes were injected 24 hours prior to tissue collection and tissues were analysed for exosome-positive cells by immunofluorescence. Pictures were taken at 60× magnification. For in vitro uptake assays, the membrane of WI-38 cells was labelled with PKH67 dye while 4175-LuT exosomes were labelled with PKH26 dye. 10 µg/ml of exosomes were first incubated with PBS or HYD-1 peptide for 30 minutes at 37° C., followed by an incubation for one hour with WI-38 cells at 37° C. Excess exosomes were washed off and pictures were taken by Nikon confocal microscope (Eclipse TE2000U). The amount of exosomes localizing to the lung was analysed by immunofluorescence or using the Odyssey imaging system (LI-COR Biosciences, Lincoln, NE, USA). Briefly, Near-infrared (NIR) dye labelled exosomes were injected 24 hours prior to tissue collection and tissues were analysed for exosome-positive areas. Whole lung images were analysed by image J software, by red fluorescence area in arbitrary unit (a.u.).

Photoconversion and EM Processing.

Cryostat sections prepared at a 15 μm thickness were placed on glass slides and re-fixed in 0.075M sodium Cacodylate, pH 7.4, containing 2.5% glutaraldehyde. Photoconversion was achieved as follows: Slides were washed twice in 0.1M sodium cacodylate buffer, pH 7.4. Autofluorescence was quenched using 100 mM $NH_4Cl$ in cacodylate buffer for 45 minutes. Based on optimization experiments, sections were photoconverted for two hours by incubation in 5.4 mg/ml 3,3'-diaminobenzidine in 0.1M sodium cacodylate buffer, pH 7.4 and exposure to the light of an Intensilight C-HGFI 130-W mercury lamp and a 4×/0.1 NA objective (Nikon Inverted Microscope Eclipse Ti).

EM processing was performed as follows: Sections were post-fixed in 1% osmium tetroxide buffer for 15 minutes on ice. After washing with water, slides were placed in 1% aqueous uranyl acetate for 30 minutes. Sections were washed with water, dehydrated in a graded series of ethanol concentrations and subsequently in acetone for 10 minutes at room temperature. Samples were embedded in Eponate. Serial sections were cut at 70 nm in thickness and transferred to formvar-coated slot grids and imaged on a JEOL 100CX at 80 kV with an AMT XR41 digital imaging system.

Gene Expression Analysis.

Cell lines were analysed for specific genes using pre-designed TaqMan assays (Applied Biosystems, Foster City, CA, USA). Briefly, RNA was extracted from tissues or cells using the RNeasy kit (Qiagen, Venlo, Netherlands), and reverse transcribed using Superscript Vilo (Life Technologies). qRT-PCR was performed on a 7500 Fast Real Time PCR System (Applied Biosystems), using TaqMan Universal PCR Master Mix (Applied Biosystems). Relative expression was normalized to β-actin levels.

Knockdown and Overexpression Cell Preparation.

For shRNA mediated knockdown of $ITG\beta_4$ and $ITG\beta_5$, specific interfering lentiviral vectors containing GFP reporter and puromycin resistance gene cassettes were used. Briefly, oligo CCGGGAGGGTGTCATCACCATT-GAACTCGAGTTCAATGGTGATGACACCCTCTTTTT G (SEQ ID NO: 2) targeting the GAGGGTGTCATCAC-CATTGAA (SEQ ID NO: 3) sequence in the human ITGB4 gene (Entrez gene ID: 3691) or oligo CCG-GAGCTTGTTGTCCCAATGAAATCTCGAGATTTCAT-TGGGACAACAAGCTTTTTT G targeting AGCTTGTTGTCCCAATGAAAT (SEQ ID NO: 4) sequence in the human ITGB5 gene (Entrez gene ID: 3693) was cloned into the pLKO.1 vector. As a control, the empty pLKO.1 vector was used. For retrovirus production for integrin overexpression, the pWZL and pBabe vectors systems were used. pWZL-hygro-$ITGB_4$ and pBabe-puro-$ITG\beta_4$ were kindly provided by Dr. Filippo Giancotti (MSKCC). Lentiviral and retroviral particles were packaged using 293T cells. Infected target cells were selected using 500 μg/ml hygromycin B or 2 μg/ml puromycin (Invitrogen).

Flow Cytometry Analysis.

Bone marrow was prepared for flow cytometry as previously described (Peinado et al., "Melanoma Exosomes Educate Bone Marrow Progenitor Cells Toward a Pro-Metastatic Phenotype Through MET," Nat. Med. 18:883-891 (2012), which is hereby incorporated by reference in its entirety). For analysis of lung, tissues were minced and then digested at 37° C. for 20 minutes with an enzyme cocktail (Collagenase A, Dispase and DNaseI, Roche Applied Science, Penzberg, Germany). Single cell suspensions were prepared by filtering through a 70 μm strainer and passing through an 18G syringe. Lung fibroblasts were identified by flow cytometry using an anti-mouse rabbit polyclonal S100A4 (1:50, Abcam; ab27957), revealed by Alexa Fluor 568-conjugated goat anti-rabbit secondary (A-11011, Life Technologies, 1:400). For liver, tissues were mechanically dissociated, and single-cell suspensions were filtered through a 40 μm strainer. Allophycocyanin-conjugated F4/80 (1:100, eBioscience; clone BM/8) was used to identify liver macrophages by flow cytometry. Cell fluorescence indicating fluorescently-labelled exosome uptake was analysed using a FACSCalibur or a FACSCanto (Beckton Dickinson, Franklin Lakes, NJ, USA). FACS data was analysed with FlowJo software (TreeStar Inc., Ashland, OR, USA).

Migration Assay.

Twenty thousand cells were plated in 24-well transwell plates with inserts (8 μm pore size, Corning, Corning, NY, USA) and were incubated in 37° for six hours. Cell inserts were fixed with 4% paraformaldehyde (PFA) for 10 minutes, followed by PBS wash and hematoxylin staining to allow visualization and counting. Nine random fields were counted per well at 20× magnification and the average number of migrated cells per field was calculated.

Human Studies.

Human peripheral blood samples were obtained from control healthy subjects and cancer patients with lung or liver metastasis, or from patients without distant metastasis at Weill Cornell Medical College, University Medical Center Hamburg-Eppendorf, Oslo University Hospital, Memorial Sloan Kettering Cancer Center, and University of Nebraska Medical Center, all pathologically confirmed. All individuals provided informed consent for blood donation on approved institutional protocols (WCMC IRB 0604008488 (DL), MSKCC IRB 12-137A (JB)). Plasma or serum exosomes were isolated as previously described (Peinado et al., "Melanoma Exosomes Educate Bone Marrow Progenitor Cells Toward a Pro-Metastatic Phenotype Through MET," Nat. Med. 18:883-891 (2012), which is hereby incorporated by reference in its entirety). $ITG\beta_4$ and $ITG\alpha_v$ levels in exosomes were measured by ELISA (ABIN417641 and ABIN417609 from Antibodies Online, Atlanta, GA, USA, and LS-F7188 from LifeSpan Biosciences, Inc., Seattle, WA, USA), using 2 μg of exosomes per 100 μl of sample diluent, in duplicate reactions, according to the manufacturer's instructions.

Murine Studies.

All mouse work was performed in accordance with institutional, IACUC and AAALAS guidelines, by the animal protocol #0709-666A. All animals were monitored for abnormal tissue growth or ill effects according to AAALAS guidelines and sacrificed if excessive deterioration of animal health was observed. No statistical method was used to pre-determine sample size. No method of randomization was used to allocate animals to experimental groups. The investigators were not blinded to allocation during experiments and outcome assessment. Mice that died before the predetermined end of the experiment were excluded from the analysis. In none of the experiments did tumours exceed the maximum volume allowed according to our IACUC protocol, specifically 2 $cm^3$. For exosome localization, education, and tumour implantation experiments for murine cell lines, 6 weeks old C57BL/6 Mus musculus females purchased from Jackson labs were used. For exosome localization, education, and tumour implantation experiments for human cell lines, 6-8 weeks old NCr nude (NCRNU-F sp/sp) females purchased from Taconic were used. For lung metastasis studies using organotropic lines, 6-8 week old nude female mice were pre-educated with exosomes for 3 weeks followed by tail vein injection of $2\times10^5$ or intra-cardiac injection of 1×10⁵ luciferase-positive cancer cells resuspended in 100 μl PBS. Four weeks after intra-cardiac injection and eight weeks after tail vein injection, lung metastasis was measured using the IVIS 200 bioluminescence imaging system (Xenogen, Caliper Life Sciences, Hopkinton, MA) and tissues were cut in 6 μm sections and stained with hematoxylin and eosin for histology. To analyse the role of exosome education in tumour metastasis, 6-8 week old C57BL/6 female mice pre-educated with pancreatic cancer-derived exosomes were injected intrasplenically with 1×10⁶ PAN02 mCherry cells resuspended in 300 of Matrigel (Corning). One or 21 days later, mice were sacrificed, and livers were analysed for metastatic lesions by measuring liver weight.

To follow the levels of tumour-derived exosomes in plasma of tumour-bearing mice, 1×10⁶ 4175 lung tropic cells were injected in the mammary fat pad of nude mice. Two hundred and fifty microliters of murine blood was drawn from the retro-orbital sinus when tumour size was over 800 mm³, followed by tumour resection. One week after the tumour was resected, mice were analysed by bioluminescence IVIS imaging for luciferase activity and separated into two groups: recurrence/tumour free and recurrent tumours. Murine blood was drawn and the plasma of mice within the same group was pooled for exosome isolation. Western blot analysis with anti-human ITGβ$_4$ antibodies was used to detect tumour-derived exosomes.

To assess exosome-induced vascular leakiness, 10 μg micrograms of total exosome protein were injected by retro-orbital injection. Twenty hours after exosome treatment, mice were injected with 2 mg of Texas Red®-lysine fixable dextran 70,000 MW (Invitrogen) via retro-orbital injection. One hour after dextran injection, mice were sacrificed and perfused with PBS. Lungs were dissected and fixed in a mix of 2% PFA and 20% sucrose overnight, then embedded in Tissue-tek O.C.T. embedding compound (Electron Microscopy Sciences, Hatfield, PA, USA) and frozen in a dry ice/ethanol bath. O.C.T. blocks were sectioned and stained for DAPI, pictures were taken by Nikon confocal microscope (Eclipse TE2000U). Images were analysed by image J software, by red fluorescence area in arbitrary unit (a.u.).

Tissue Processing and Immunofluorescence.

For histological analysis, tissues were dissected and fixed in a mix of 2% PFA and 20% sucrose in PBS overnight, then embedded in Tissue-tek O.C.T. embedding compound. Blocks were frozen in a dry ice/ethanol bath. For immunofluorescence, 6 μm O.C.T tissue cryosections were stained with antibodies against F4/80 (1:100, eBioscience; BM8), Fibronectin (1:50, Santa Cruz; IST-9), S100A4 (1:100, Abcam; ab27957), SPC (1:100, Santa Cruz; FL-197), Laminin (1:50, abcam; ab11575), CD31 (1:100, Santa Cruz; MEC 13.3), EpCAM (1:50, Santa Cruz; HEA125). Secondary antibodies conjugated to Alexa Fluor 488 or 549 were used (A-11001 and A-11007, Life Technologies). Fluorescent images were obtained using a Nikon confocal microscope (Eclipse TE2000U) and analysed using Nikon software (EZ-C1 3.6).

Western Blot Analysis.

Exosomes or cells were lysed with RIPA buffer containing a complete protease inhibitor tablet (Roche). Lysates were cleared by centrifugation at 14,000×g for 20 minutes. Supernatant fractions were used for Western blot. Samples were separated on a Novex 4-12% Bis-Tris Plus Gel (Life Technologies), and transferred onto a PVDF membrane (Millipore, Billerica, MA, USA). Membranes were processed for Ponceau red staining followed by one hour blocking and primary antibody incubation. The antibodies against the following proteins were used for Western blot analysis: ITGβ$_1$ (1:1000, Cell Signaling; 4706), ITGβ$_4$ (1:500, Cell Signaling; 4707), ITGα$_6$ (1:1000, Cell Signaling; 3750), ITGα$_2$ (1:10000, abcam; ab133557), ITGα$_3$ (1:1000, abcam; ab190731), ITGα$_v$ (1:500, abcam; ab117611), ITGβ$_5$ (1:500, Cell Signaling; 4708), ITGβ$_3$ (1:500, Millipore; AB2984) Alix (1:1000, Cell Signaling; 3A9), and GAPDH (1:10000, Cell Signaling; 14C10). Anti-rabbit IgG, HRP-linked Antibody (1:3000, Cell Signaling; 7074) and anti-mouse IgG, HRP-linked Antibody (1:3000, Cell Signaling; 7076) were used as secondary antibodies.

In Situ Protein Expression Analysis (in-Cell Western™ Assay, LI-COR).

Cells were plated in a 96-well plate and treated with 10 μg/ml exosomes for two hours then processed according to the protocol provided by the manufacturer. Briefly, cells were fixed with 4% PFA and washed with 0.1% Tween/PBS. Cells were then blocked using Odyssey blocking buffer for one hour and stained overnight at 4° C. with primary antibody. The following day cells were washed again and incubated with LI-COR secondary antibodies for one hour at room temperature followed by fluorescent imaging using Odyssey. The antibodies against the following proteins were used: Src (1:100, Cell Signaling; 2109), p-Src (1:100, Cell Signaling; 2101), AKT (1:100, Cell Signaling; 9272), p-AKT (1:100, Cell Signaling; 9271), p38 (1:100, Cell Signaling; 9212), p-p 38 (1:100, Cell Signaling; 9211), NF-κB (1:100, Cell Signaling; 3034), p-NF-κB (1:100, Cell Signaling; 3033), NFAT (1:100, Thermo Scientific; PA1-023), ILK (1:100, abcam; ab52480), FAK (1:100, abcam; ab40794), and GAPDH (1:100, Cell Signaling; 14C10). IRDye® 800CW anti-Rabbit IgG (1:800, LI-COR) was used as a secondary antibody.

ELISA.

A standard curve (known concentration curve) was prepared of specific integrin ranges from 10 ng/mL to 0 ng/mL (10, 5, 2.5, 1.25, 0.625, 0.312, 0.156, 0). 2 micrograms of exosome samples were added to each well of a 96-well kit as well as standards described above. Each well already had an antibody coating and was blocked by the kit provider. The wells were incubated overnight at 4° C. The samples and standards were aspirated out and washed with washing solution three times. Another antibody was added (to sandwich) in each well and was incubated for 30 minutes at 37° C. The wells were washed with washing solution five times. Substrate solution was added in each well and incubated for up to 30 minutes at 37° C. Stopping solution was added to stop the reaction and the O.D. of samples was measured at 450 nm. Using the standard curve, the O.D. was used to back calculate the concentration of integrin in each well of exosomes.

Statistical Analysis.

Error bars in graphical data represent means±s.e.m. Mouse experiments were performed in duplicate or triplicate, using 3-6 mice per treatment group. Statistical significance was determined using a two-tailed Student's t-test and one-way ANOVA where p-values of P<0.05 were considered statistically significant. Variance was similar between the groups that were statistically compared.

Example 1—Future Metastatic Sites Uptake Exosomes

Figure 2B:
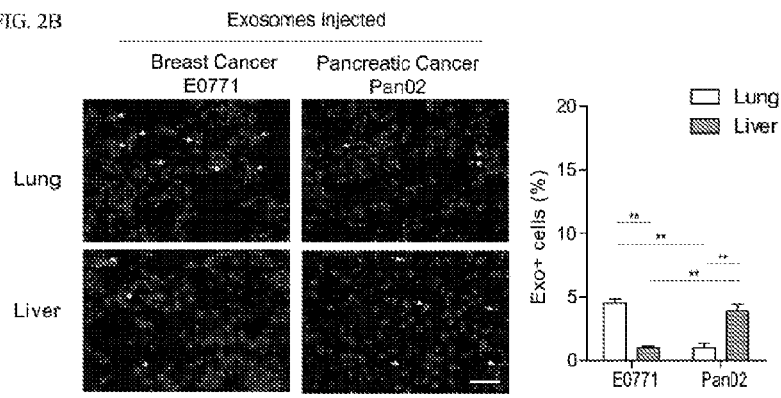

To examine whether tumour exosomes colonize specific organ sites, exosomes were isolated from organotropic human breast and pancreatic cancer cell lines which metastasize primarily to the lung (MDA-MB-231), liver (BxPC-3, HPAF-II), or both (MDA-MB-468). 10 µg of near infra-red (NIR) or red fluorescently-labelled exosomes were then retro-orbitally injected into nude mice and, 24 hours post-injection, exosome biodistribution and uptake was quantified in distant organs by NIR whole lung imaging and confocal microscopy (FIG. 1A and FIG. 2A). A more than three-fold increase in uptake of MDA-MB-231 and/or 468- versus BxPC-3- and HPAF-II-derived exosomes was observed in the lung (FIG. 1A). In contrast, liver uptake of BxPC-3 and HPAF-II exosomes was four times more efficient than that of MDA-MB-231 exosomes (FIG. 1A). Moreover, murine E0771 breast cancer exosomes were four-to-five-fold more efficiently uptaken in lung, whereas murine Pan02 pancreatic cancer exosomes were four times more efficiently uptaken in liver (FIG. 2B). Therefore, the organ specificity of exosome biodistribution matched the organotropic distribution of the cell line of origin in both immune-compromised and immune-competent models.

Figure 2C:
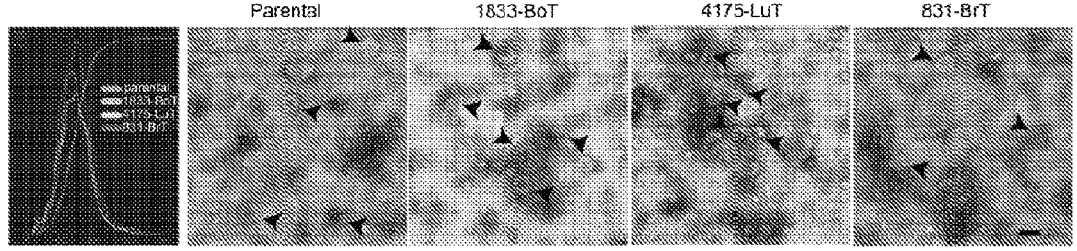
Figure 2D:
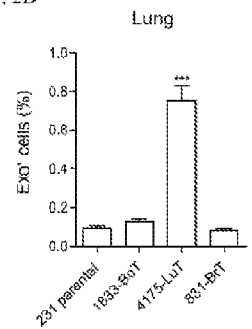
Figure 2E:
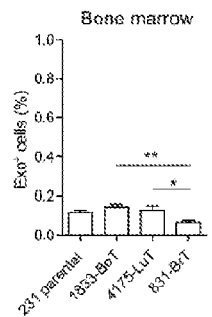

These observations suggested that exosomes could promote organ-specific metastasis. Whether exosomes from the MDA-MB-231 sub-lines that colonize lung, bone or brain (4175-LuT, 1833-BoT and 831-BrT, respectively) (Kang et al., "A Multigenic Program Mediating Breast Cancer Metastasis to Bone," *Cancer Cell* 3:537-549 (2003); Gupta et al., "Identifying Site-Specific Metastasis Genes and Functions," *Cold Spring Harb. Symp. Quant. Biol.* 70:149-158 (2005); Minn et al., "Genes That Mediate Breast Cancer Metastasis to Lung," *Nature* 436:518-524 (2005); Bos et al., "Genes That Mediate Breast Cancer Metastasis to the Brain," *Nature* 459:1005-1009 (2009), which are hereby incorporated by reference in their entirety) would also exhibit organ tropism was tested. Although exosomes from the MDA-MB-231 variants were similar in size and morphology (FIG. 2C), their biodistribution varied 24 hours post-injection: lung-tropic 4175-LuT exosomes preferentially localized to the lung with a more than four-fold increase in exosome-positive cells compared to 1833-BoT and 831-BrT exosomes (FIG. 1B and FIG. 2D), whereas brain-tropic 831-BrT exosomes efficiently localized to brain with more than a four-fold increase compared to 1833-BoT and 4175-LuT exosomes (FIG. 1B). Liver and bone showed no significant differences in lung-, brain- or bone-tropic MDA-MB-231-derived exosome distribution, with the exception of 831-BrT exosomes that were uptaken less efficiently by BM cells when compared to exosomes isolated from other MDA-MB-231 sub-lines (FIG. 1B and FIG. 2E). Taken together, these data suggest that exosomes from different cancer models recapitulate the organ specificity of their cell of origin.

Example 2—Exosomes Redirect Metastatic Distribution

It was hypothesized that, in addition to cell-intrinsic genetic determinants of organotropism (Minn et al., "Genes That Mediate Breast Cancer Metastasis to Lung," *Nature* 436:518-524 (2005); Bos et al., "Genes That Mediate Breast Cancer Metastasis to the Brain," *Nature* 459:1005-1009 (2009), which are hereby incorporated by reference in their entirety), tumour exosomes could also facilitate organ-specific metastatic behaviour by preparing pre-metastatic niches.

Figure 2F:
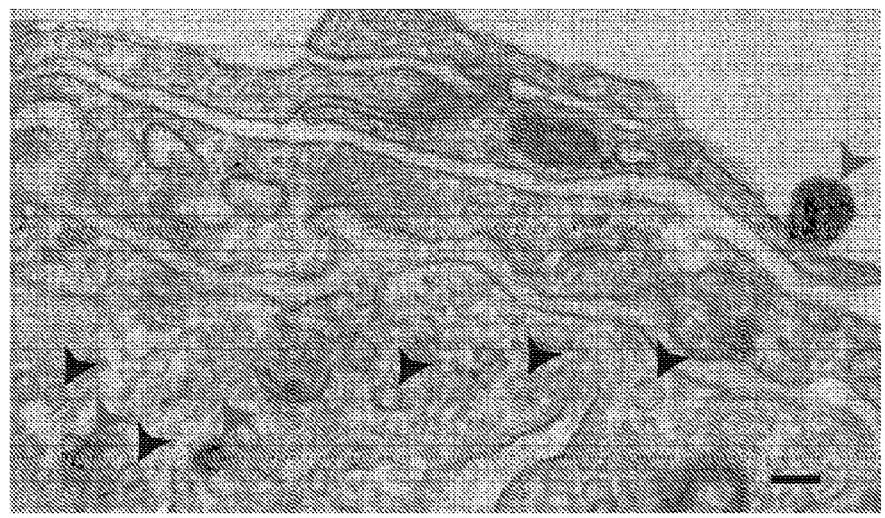
Figure 2G:
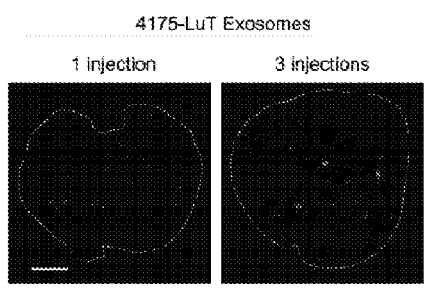

To gain insight into tumour exosome uptake at future metastatic sites, 4175-LuT exosomes labelled with FM1-43 dye were intravenously injected into naïve animals, then electron microscopy was used to distinguish endogenous versus exogenous exosomes in lung sections. Tumour FM1-43-labelled exosomes were detected in pre-metastatic cells (FIG. 2F; gray arrows, exogenous tumour-derived exosomes; black arrows, endogenous stromal exosomes). Moreover, NIR whole mount lung imaging revealed that NIR-labelled 4175-LuT exosomes accumulated in lungs of naïve animals after three consecutive daily exosome injections (FIG. 2G).

Figure 2H:
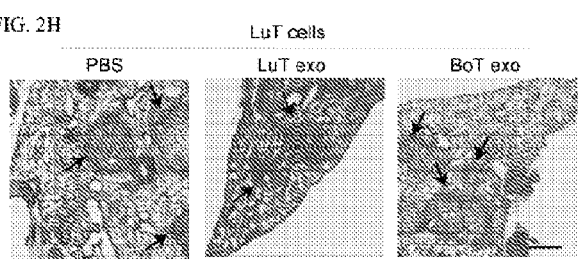
Figure 2I:
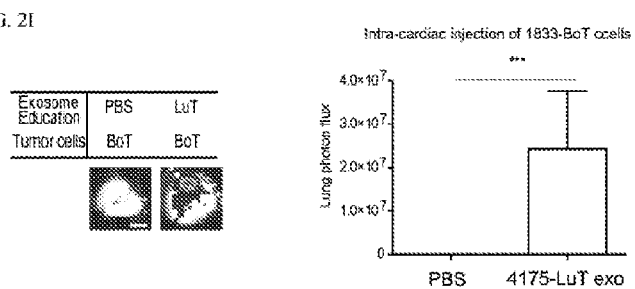

To condition or "educate" cells in specific organs, 4175-LuT or 1833-BoT exosomes were retro-orbitally injected into mice every other day for three weeks (Peinado et al., "Melanoma Exosomes Educate Bone Marrow Progenitor Cells Toward a Pro-Metastatic Phenotype Through MET," *Nat. Med.* 18:883-891 (2012), which is hereby incorporated by reference in its entirety). To functionally test exosome education of target organs, luciferase-expressing 4175-LuT or 1833-BoT cells were injected into exosome-educated mice via tail vein (FIG. 1C-D; FIG. 2H) or intracardially (FIG. 2I). Lung-tropic 4175 exosomes marginally increased lung-metastatic capacity of 4175-LuT tumours. Remarkably, education with 4175-LuT-derived exosomes, but not with 1833-BoT exosomes or PBS, yielded a significant (seven-fold with intravenous and ten thousand-fold with intracardiac injection) increase in lung-metastatic capacity of 1833-BoT cells (FIG. 1C-D; FIG. 2I). Conversely, 1833-BoT-derived exosomes did not affect 4175-LuT cell metastasis to the lung (FIG. 1C and FIG. 2H). These data suggest that organotropic tumour exosomes prepare pre-metastatic niches potent enough to facilitate metastasis even for tumour cells poorly capable of colonizing these sites.

Example 3—Exosome ITGs Determine Organotropism

Figure 3A:
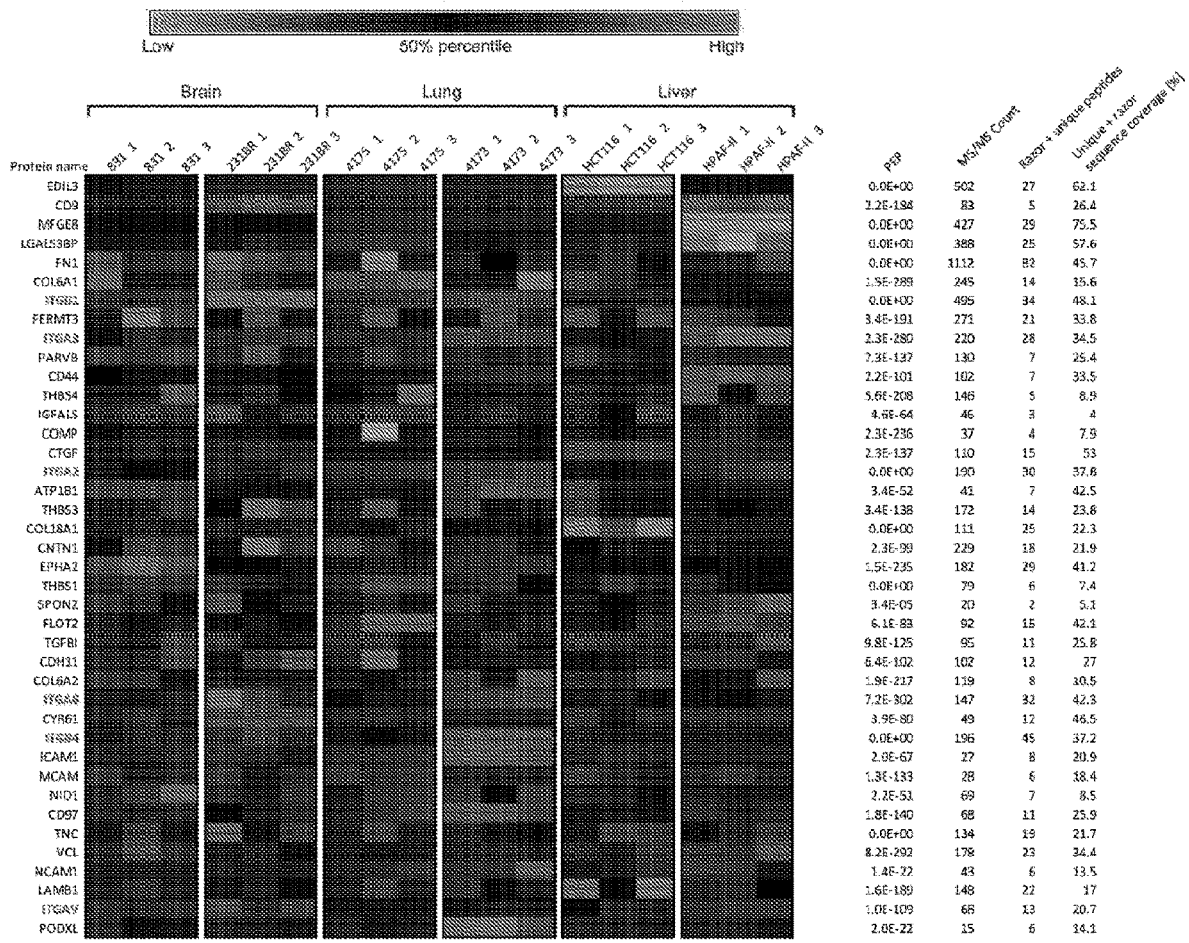
FIGS. 3A-G show proteomic and functional characterization of organotropic exosomes.

It was then postulated that exosomal adhesion molecules could regulate local microenvironments within future metastatic organs. Quantitative mass spectrometry of brain-, lung-, and liver-tropic metastatic exosomes identified six integrins among the top 40 most abundant adhesion molecules, making integrins the most highly represented protein family in this analysis. These data indicate a correlation between exosomal integrins and metastatic tropism (FIG. 3A).

Figure 3B:
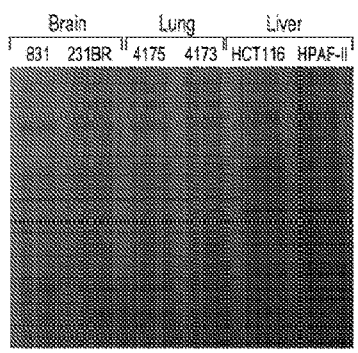

Interestingly, it was found that integrin expression profiles correlated with tissue organotropism. Both quantitative mass spectrometry (FIG. 4A) and western blot analysis (FIG. 3B and FIG. 4B) revealed that integrin alpha 6 (ITG$\alpha_6$), and its partners ITG beta 4 (ITG$\beta_4$) and ITG beta 1 (ITG$\beta_1$) (Desgrosellier et al., "Integrins in Cancer: Biological Implications and Therapeutic Opportunities," *Nat. Rev. Cancer* 10:9-22 (2010), which is hereby incorporated by reference in its entirety), were present abundantly in lung-tropic exosomes. In contrast, ITG beta 5 (ITG$\beta_5$), which associates only with ITG alpha v (ITG$\alpha_v$) (Desgrosellier et al., "Integrins in Cancer: Biological Implications and Therapeutic Opportunities," *Nat. Rev. Cancer* 10:9-22 (2010), which is hereby incorporated by reference in its entirety), was detected primarily in liver-tropic exosomes (FIG. 4A-B). These findings were confirmed by exosome proteomics on 28 organ-specific metastatic cell lines (Tables 2 and 3). Qualitative mass spectrometry revealed that ITG$\alpha_6$ was present in lung-tropic exosomes, whereas ITG$\beta_5$ was found in liver-tropic exosomes (Tables 2 and 3) consistent with quantitative proteomics data. Exosomes from 4173, 4175, and 4180 lung-tropic MDA-MB-231 variants expressed ITG$\alpha_6\beta_4$ (Table 2). Meanwhile, ITG beta 3 (ITG$\beta_3$) was present in exosomes isolated from brain tropic cells (Table 2). Notably, unlike non-cancerous lung fibroblast WI-38 or epithelial MCF10A exosomes, metastatic cell exosomes contained ITG$\alpha_2\beta_1$, suggesting that this integrin could serve as a biomarker for metastasis (Table 2).

TABLE 2

Integrin Expression in Human Exosomes in Multiple Organotropic Tumour Models

| Sites of metastasis | None | | Bone | Brain | | | | Lung | | | Lung Osteosarcoma | Rhabdomyosarcoma | |
| --- | --- | --- | --- | --- | --- | --- | --- | --- | --- | --- | --- | --- | --- |
| Cell type | Lung Fibroblast | Mammary Epithelial | Breast Cancer | Breast Cancer | | Melanoma | | Breast Cancer | | | | | |
| Cell line | Wt-38 | MCF10A | 1833 | 831 | 231BR | 131/4-5B2 | SB1B | 4173 | 4175 | 4180 | 143B | RD | CT10 |
| ITGα1 | | | | | | | + | + | | + | | | |
| ITGα2 | | + | + | + | + | | + | + | + | + | + | | |
| ITGα2b | | | | | | | + | | | | | | |
| ITGα3 | | + | + | + | + | | | + | + | + | + | | |
| ITGα4 | | | | | | + | | | | | + | + | |
| ITGα5 | | | | | | | + | + | + | + | | + | + |
| ITGα6 | | | + | + | | + | + | + | + | + | + | + | + |
| ITGα11 | | | | | | | | | | | + | | |
| ITGαv | | | + | | + | + | + | + | + | + | + | + | + |
| ITGβ1 | | + | + | + | + | + | + | + | + | + | + | + | + |
| ITGα3 | | | + | + | + | + | + | | + | + | + | + | + |
| ITGα4 | | | | | | + | + | + | + | | | | |
| ITGα5 | + | | + | | | + | + | + | + | | + | + | |
| ITGα6 | | | | | | | | | | | | | |

Integrin Expression in Human Exosomes in Multiple Organotropic Tumour Models

| Sites of metastasis | Lung | | | Liver | | | | | | | | | |
| --- | --- | --- | --- | --- | --- | --- | --- | --- | --- | --- | --- | --- | --- |
| Cell type | Wilms' Tumor | Melanoma | Uveal Melanoma | | | | | Pancreactic Cancer | | | | Gastric Cancer | |
| Cell line | CCG 9911 | CLS1 | 131/8-2L | Primary culture | Colorectal Cancer HCT116 | HT29 | SW620 | BXPC-3 | HPAF-II | MiaPaca-2 | PANC-1 | SNU1 | SNU16 |
| ITGα1 | | | | + | | | | + | + | | | | |
| ITGα2 | + | | + | + | + | + | + | + | + | + | | | |
| ITGα2b | | | | | | | | + | | | | | |
| ITGα3 | | | | + | + | + | | + | + | + | | | |
| ITGα4 | + | + | + | + | | | | | | | | | |
| ITGα5 | | + | | | | | | | | + | + | + | |
| ITGα6 | + | + | + | + | | | + | + | + | + | + | + | + |
| ITGα11 | | | | | | | | | | | | | |
| ITGαv | | + | + | + | + | | + | + | + | + | + | | |
| ITGβ1 | + | + | + | + | + | + | + | + | + | + | + | + | + |
| ITGα3 | + | + | + | + | + | + | + | + | + | + | | | |
| ITGα4 | | | | | + | + | + | + | + | + | | + | |
| ITGα5 | | + | | + | + | + | + | + | + | + | + | + | + |
| ITGα6 | | | | | | | | + | + | + | | | |

TABLE 3

Integrin Expression in Human and Murine Cell Line-derived Exosomes

| | Human | | Murine | | |
| --- | --- | --- | --- | --- | --- |
| Sites of metastasis | Majority to lung | Lung and liver | Sites of metastasis | Lung | Liver |
| Cell type | Breast cancer | | Cell type | Breast cancer | Pancreatic cancer |
| Cell line | MDA-MB-231 | MDA-MB-468 | Cell line | E0771 | Pan02 |
| ITGα$_1$ | | | ITGα$_1$ | | |
| ITGα$_2$ | + | + | ITGα$_2$ | | |
| ITGα$_{2b}$ | | | ITGα$_{2b}$ | | + |
| ITGα$_3$ | + | + | ITGα$_3$ | + | + |
| ITGα$_4$ | | | ITGα$_4$ | | |
| ITGα$_5$ | | | ITGα$_5$ | + | + |
| ITGα$_6$ | + | + | ITGα$_6$ | + | + |
| ITGα$_V$ | | + | ITGα$_V$ | + | + |
| ITGβ$_1$ | + | + | ITGβ$_1$ | + | + |
| ITGβ$_3$ | + | + | ITGβ$_3$ | + | + |

TABLE 3-continued

Integrin Expression in Human and Murine Cell Line-derived Exosomes

| | Human | | | Murine | |
|---|---|---|---|---|---|
| Sites of metastasis | Majority to lung | Lung and liver | Sites of metastasis | Lung | Liver |
| Cell type | Breast cancer | | Cell type | Breast cancer | Pancreatic cancer |
| Cell line | MDA-MB-231 | MDA-MB-468 | Cell line | E0771 | Pan02 |
| ITGβ$_4$ | | + | ITGβ$_4$ | | + |
| ITGβ$_5$ | | + | ITGβ$_5$ | | + |
| ITGβ$_6$ | | + | ITGβ$_6$ | | |

Figure 3C:
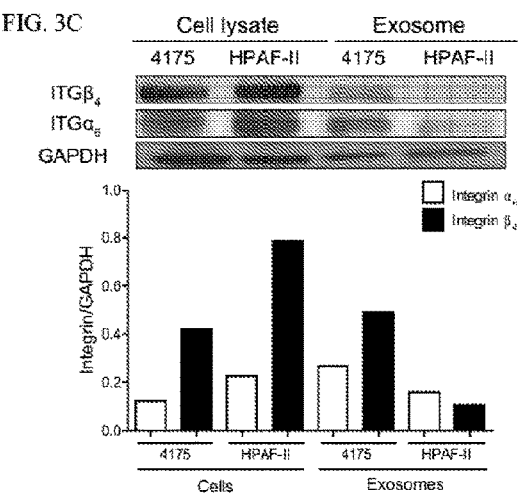

Importantly, exosomal integrin expression does not necessarily reflect cellular integrin expression, consistent with selective packaging of integrins in exosomes (FIG. 3C). Taken together, these data suggest that exosomal integrin expression patterns underlie organotropism to the lung, liver, and brain.

Example 4—Distinct Cells Uptake Tropic Exosomes

Figure 3D:
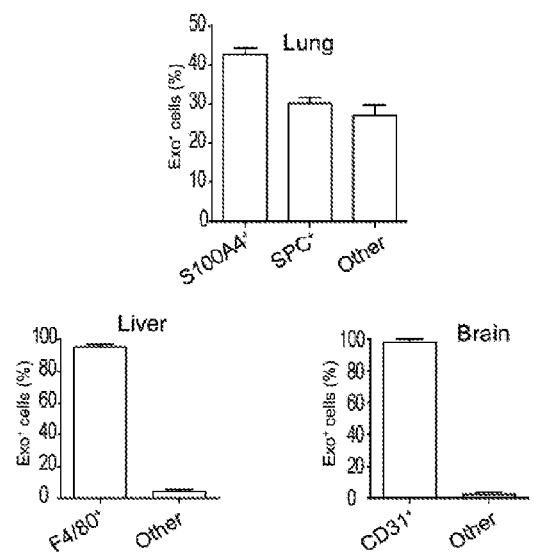
Figure 3E:
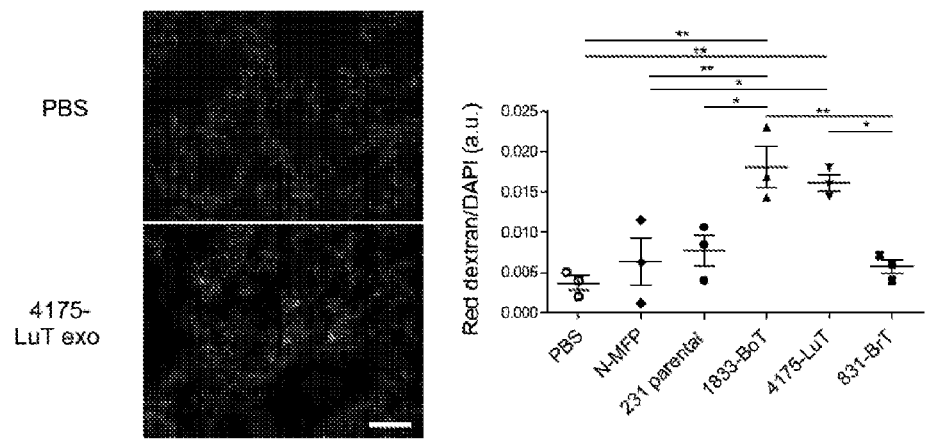
Figure 3F:
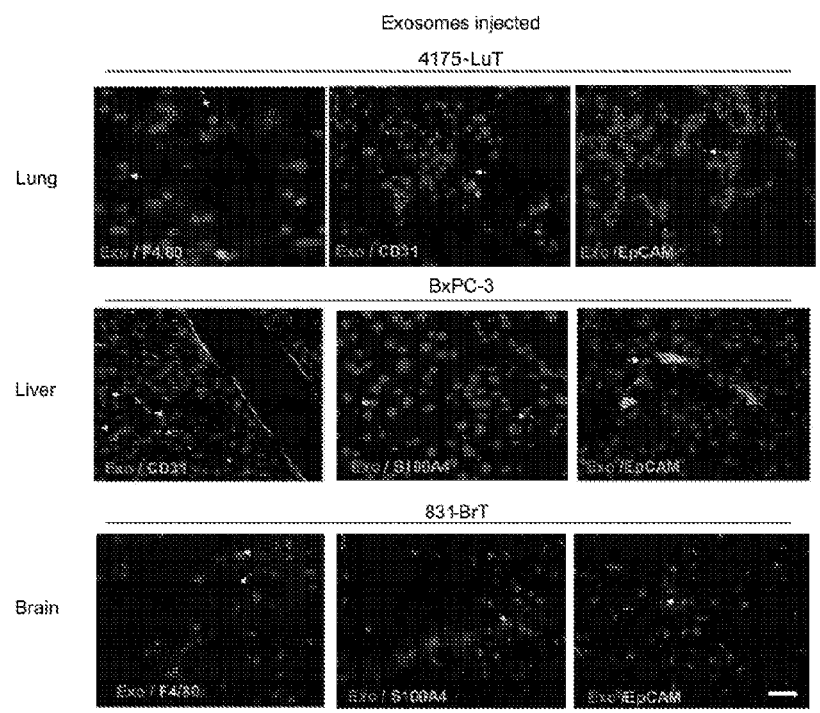

To identify the cells uptaking tumour exosomes in each organ, red fluorescently-labelled exosomes from 4175-LuT, 1833-BoT, BxPC-3-liver tropic or 831-BrT cells were intravenously injected into mice (FIG. 3D-E and FIG. 4C). Both 1833-BoT and 4175-LuT exosomes promoted vascular leakiness 24 hours post-injection, prior to exosome uptake by specific lung cells (FIG. 3E). These observations fit with previous studies using melanoma exosomes (Peinado et al., "Melanoma Exosomes Educate Bone Marrow Progenitor Cells Toward a Pro-Metastatic Phenotype Through MET," *Nat. Med.* 18:883-891 (2012), which is hereby incorporated by reference in its entirety), suggesting that exosomes first permeabilize vessels, allowing for exosome diffusion before uptake by parenchymal cells. Unexpectedly, it was found that the specific cell-type responsible for exosome uptake varied depending on the metastatic organ. Lung-tropic 4175 exosomes mainly co-localized with S100A4-positive fibroblasts and surfactant protein C-positive epithelial cells (40% and 30% of exosome-positive cells, respectively) in the lung (FIG. 3D, 3F, top panel, FIG. 4C). In contrast, pancreatic cancer exosomes derived from liver-tropic BxPC-3 cells fused with Kupffer cells (90% of exosome-positive cells; FIG. 3D, 3F, middle panel, FIG. 4C) (Costa-Silva et al., "Pancreatic Cancer Exosomes Initiate Pre-Metastatic Niche Formation in the Liver," *Nat. Cell. Biol.* (2015), which is hereby incorporated by reference in its entirety). Finally, 831-BrT exosomes interacted mainly with CD31-positive brain endothelial cells (98% of exosome-positive cells; FIG. 2C and FIG. 3D, 3F, lower panel, FIG. 4C). Collectively, these data demonstrate that specific tissue-resident stromal cells differentially uptake tumour exosomes in metastatic target organs.

Figure 3G:
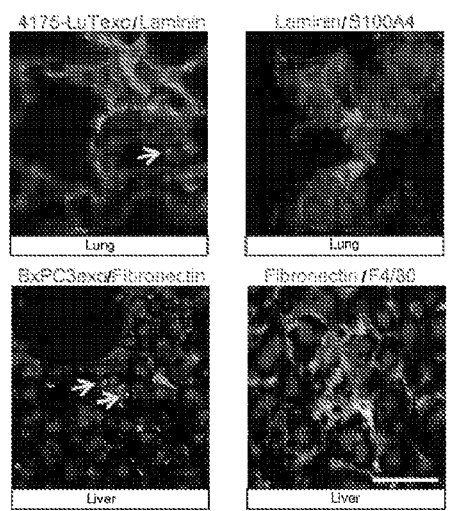

It was hypothesized that the unique exosomal integrins may interact with cell-associated extracellular matrix (ECM), mediating exosome uptake in specific target organs. It was found that 4175-LuT exosomes expressing ITGα$_6$β$_4$ and ITGα$_6$τβ$_1$ co-localized with S100A4-positive cells in laminin-rich lung microenvironments (FIG. 3G, top panels). Meanwhile, ITGα$_v$β$_5$-expressing liver-tropic pancreatic BxPC-3 exosomes co-localized with F4/80+ macrophages in fibronectin-rich liver microenvironments (FIG. 3G, lower panels). Therefore, specific exosomal integrins may selectively adhere to ECM-enriched cellular areas in the lung and liver.

Example 5—Exosomal Tropism Requires ITGβ$_4$ and ITGβ$_5$

It was next asked if manipulating the integrin cargo packaged into exosomes could impact metastatic organotropism. To test the requirement for exosomal ITGβ$_4$ in lung tropism, ITGβ$_4$ expression was knocked down in 4175-LuT cells using shRNAs (4175β4KD; FIG. 5A). A more than three-fold reduction in ITGβ4KD-labelled exosomes was found in the lung compared to control-labelled exosomes 24 hours post-injection (FIG. 6A). To test the requirement for exosomal ITGβ$_4$ binding to laminin for lung tropism, integrin binding was blocked using RGD and HYD-1 peptides. Pre-incubation of 4175-LuT exosomes with HYD-1, which blocks laminin receptors (Sroka et al., "The Minimum Element of a Synthetic Peptide Required to Block Prostate Tumor Cell Migration," *Cancer Biology & Therapy* 5:1556-1562 (2006), which is hereby incorporated by reference in its entirety), dramatically reduced exosome uptake in the lung, while RGD, which blocks fibronectin receptors but not ITGβ$_4$ (Ruoslahti, et al., "Arg-Gly-Asp: a Versatile Cell Recognition Signal," *Cell* 44:517-518 (1986), which is hereby incorporated by reference in its entirety), did not significantly alter exosome uptake in lung (FIG. 6A). Pre-treatment of 4175-LuT exosomes with HYD-1 peptide also prevented their uptake by WI-38 lung fibroblasts in vitro (FIG. 5B). Conversely, ITGβ$_4$ overexpression in 1833-BoT exosomes was sufficient to dramatically increase exosome uptake in lung (FIG. 5C and FIG. 6B). These data demonstrate that integrins are responsible for organ-specific uptake of exosomes and that ITGβ$_4$ promotes tumour exosome adhesion within lung.

It was next investigated whether ITGβ$_4$KD exosomes could modulate the metastatic organotropism of 4175-LuT models. Knockdown of ITGβ$_4$ was sufficient to reduce the lung metastatic capacity of 4175-LuT cells (FIG. 6C). Education with 4175-LuT exosomes, but not ITGβ$_4$KD exosomes, rescued the metastatic ability of ITGβ$_4$KD cells, yielding metastasis similar to 4175-LuT cells (FIG. 5D and FIG. 6C). Therefore, ITGβ$_4$-expressing exosomes can confer lung-metastatic behaviour to cells with limited capacity to colonize the lung. Similarly, ITGβ$_5$ knock-down in BxPC-3 exosomes decreased their liver uptake by sevenfold compared to control BxPC-3 exosomes (FIG. 5E-F). Moreover, pre-incubation with RGD peptide or anti-ITGα$_v$β$_5$ antibody, but not HYD-1 peptide, significantly reduced BxPC-3 and Pan02 exosome adhesion to the liver (FIG. 5G-H, respectively). Importantly, RGD peptides also inhibited the education effect of Pan02 exosomes, subsequently blocking pre-metastatic niche formation and liver metastasis (FIG. 5I). These data support the hypothesis that local microenvironmental changes induced by specific exosomal cargo (i.e., ITGβ$_4$ or ITGβ$_5$) can dictate metastatic organotropism.

Example 6—Exosomal ITGs Activate S100 Genes

To identify downstream effects of exosomal interaction with target cells, Kupffer cells were educated with either BxPC-3 or BxPC-3 ITGβ$_5$KD exosomes every other day for two weeks. Unbiased analysis of gene expression by RNA sequencing in Kupffer cells identified 906 genes upregulated over two-fold following treatment with BxPC-3 exosomes compared to BxPC-3 ITGβ$_5$KD exosomes. Cell migration genes were most prominently upregulated (two-fold for 221 genes; four-fold for 42 genes). Of these, S100A8, S100A9, and SLOOP were upregulated over four-fold (FIG. 6D; GEO accession number GSE68919). Since pro-inflammatory S100 gene expression correlates with metastasis (Grum-Schwensen et al., "Suppression of Tumor Development and Metastasis Formation in Mice Lacking the S100A4(mts1) Gene," *Cancer Res.* 65:3772-3780 (2005); Lukanidin et al., "Building the Niche: the Role of the S100 Proteins in Metastatic Growth," *Semin. Cancer Biol.* 22:216-225 (2012), which are hereby incorporated by reference in their entirety), S100 genes were analyzed in tumour exosome-educated lung WI-38 fibroblasts and human bronchial epithelial cells (HBEpCs). Multiple S100 genes (S100A4, -A6, -A10, -A11, -A13, and -A16) were upregulated more than five-fold upon WI-38 fibroblast treatment with 4175-LuT exosomes versus 4175-LuT ITGβ$_4$KD exosomes (FIG. 6D). Interestingly, S100 genes remained unchanged in HBEpCs treated with 4175-LuT exosomes (FIG. 6D). Moreover, exosome-treated lung fibroblasts proliferated and migrated more compared to controls (FIG. 5J-K), which correlated with a higher frequency of S100A4$^+$ cells in lungs following three weeks of education with 4175-LuT, but not 4175β$_4$KD exosomes (FIG. 5L). ITGβ$_4$-signaling proteins (Kim et al., "Integrin (alpha6beta4) Signals Through Src to Increase Expression of S100A4, a Metastasis-promoting Factor: Implications for Cancer Cell Invasion," *Mol Cancer Res* 7:1605-1612 (2009); Abdel-Ghany et al., "Focal Adhesion Kinase Activated by Beta(4) Integrin Ligation to mCLCA1 Mediates Early Metastatic Growth," *J. Biol. Chem.* 277: 34391-34400 (2002); Mainiero et al., "p38 MAPK is a Critical Regulator of the Constitutive and the Beta4 Integrin-regulated Expression of IL-6 in Human Normal Thymic Epithelial Cells," *Eur. J. Immunol.* 33:3038-3048 (2003); Weaver et al., "Beta4 Integrin-dependent Formation of Polarized Three-dimensional Architecture Confers Resistance to Apoptosis in Normal and Malignant Mammary Epithelium," *Cancer cell* 2:205-216 (2002); Nikolopoulos et al., "Targeted Deletion of the Integrin Beta4 Signaling Domain Suppresses Laminin-5-dependent Nuclear Entry of Mitogen-activated Protein Kinases and NF-kappaB, Causing Defects in Epidermal Growth and Migration," *Mol. Cell Biol.* 25:6090-6102 (2005), which are hereby incorporated by reference in their entirety) in WI-38 fibroblasts treated with 4175-LuT- or 4175β$_4$KD exosomes were then surveyed by in-cell western blot analysis. Notably, only Src/p-Src levels increased in an exosomal ITGβ$_4$-dependent manner (FIG. 5M), consistent with the known roles of ITGα$_6$β$_4$ in Src activation and S100A4 expression (Kim et al., "Integrin (alpha6beta4) Signals Through Src to Increase Expression of S100A4, a Metastasis-promoting Factor: Implications for Cancer Cell Invasion," *Mol Cancer Res* 7:1605-1612 (2009), which is hereby incorporated by reference in its entirety). Therefore, in addition to their adhesive properties, exosomal integrins can activate Src and upregulate pro-migratory and pro-inflammatory S100 molecules in specific resident cells within distant tissue microenvironments, influencing the expression of genes implicated in facilitating tumour metastasis.

Example 7—Exosome ITGs as Organotropism Biomarkers

Next, it was investigated whether exosomal integrin content could predict tumour progression. ITGβ$_4$ levels were elevated in plasma of mice six weeks after orthotopic 4175-LuT cell injection into the mammary fat pad, but were significantly reduced following successful tumour resection (FIG. 8A). Furthermore, ELISA assays were performed for plasma-derived exosomal integrins in patients with lung or liver metastasis (ITGβ$_4$ or ITGα$_v$, the binding partner of ITGβ$_5$, respectively). Elevated ITGβ$_4$ levels were found in exosomes from patients with lung metastasis (regardless of tumor-type) versus patients with no metastasis or liver metastasis (FIG. 8B). Exosomes isolated prior to metastasis expressed high exosomal ITGβ$_4$, successfully predicting which breast cancer patients would progress to develop lung metastasis (POD) (FIG. 7A). ITGα$_v$ was significantly increased in exosomes isolated from cancer patients with liver metastasis versus patients with no metastasis or lung metastasis (FIG. 8C). Finally, exosomal ITGα$_v$ levels at diagnosis were higher in pancreatic cancer patients who developed liver metastasis compared to those without liver metastasis within three years post-diagnosis and to control subjects (FIG. 7B). Taken together, these data indicate that the specific exosomal integrins in breast and pancreatic cancer patient plasma correlate with and predict likely sites of metastasis.

Example 8—Exosome ITGβ$_1$, ITGα$_2$, and ITGα$_3$ as Biomarkers for Cancer

Figure 10:
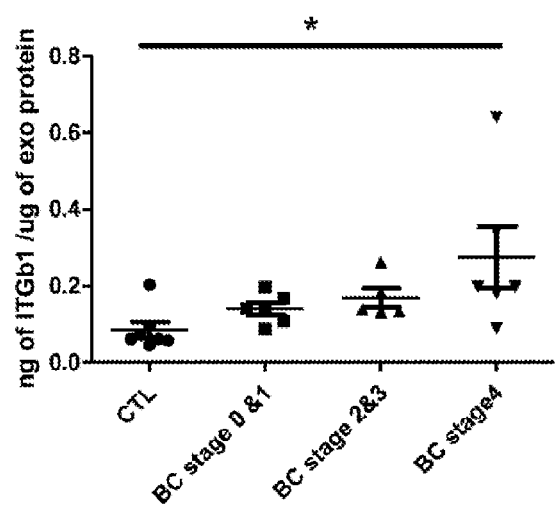
FIG. 10 shows a human patient exosomal ITGβ$_1$ ELISA. The exosomes were isolated from human plasma. The amount of ITGβ$_1$ per microgram of exosome was analyzed in healthy control subjects (n=7), patients with breast cancer stage 0 and 1 (n=6), stage 2 and 3 (n=5), and stage 4 (n=6). Bars depict average±s.e.m. *P<0.05.

Next, exosomal ITGβ$_1$ content was analyzed as a potential marker for tumor exosomes. Exosomes were isolated from human plasma obtained from healthy control subjects, patients with breast cancer stage 0 and 1, stage 2 and 3, and stage 4. Elevated exosomal ITGβ$_1$ levels were found in breast cancer patients of all stages as compared to control subjects (FIG. 10). These data indicate that exosomal ITGβ$_1$, and its binding partners ITGα$_2$ and and ITGα$_3$ may be biomarkers of cancer.

Discussion

Since Stephen Paget's hypothesis first emerged, many studies have focused on identifying cell-intrinsic determinants of organ-specific metastasis (Muller et al., "Involvement of Chemokine Receptors in Breast Cancer Metastasis," *Nature* 410:50-56 (2001); Lu et al., "Organotropism of Breast Cancer Metastasis," *Journal of Mammary Gland Biology and Neoplasia* 12:153-162 (2007); Minn et al., "Genes That Mediate Breast Cancer Metastasis to Lung," *Nature* 436:518-524 (2005); Bos et al., "Genes That Mediate Breast Cancer Metastasis to the Brain," *Nature* 459:1005-1009 (2009); Minn et al., "Distinct Organ-specific Metastatic Potential of Individual Breast Cancer Cells and Primary Tumors," *J. Clin. Invest.* 115:44-55 (2005), which are hereby incorporated by reference in their entirety). It is now shown that tumour-derived exosomes prepare a favourable microenvironment at future metastatic sites and mediate non-random patterns of metastasis. Determinants of exosome-mediated organ-specific conditioning that allow redirection of metastasis are identified. Previously, adhesion and ECM molecules, such as integrins, tenascin, and periostin, were shown to promote metastasis of disseminating cancer cells (Oskarsson et al., "Breast Cancer Cells Produce Tenascin C as a Metastatic Niche Component to Colonize the Lungs," *Nature Medicine* 17:867-874 (2011); Fukuda et al., "Periostin Is a Key Niche Component for Wound Metastasis of Melanoma," *PLoS One* 10:e0129704 (2015), Radisky et al., "Order and Disorder: the Role of Extracellular Matrix in Epithelial Cancer," *Cancer Invest.* 20:139-153 (2002); Weaver et al., "Reversion of the Malignant Phenotype of Human Breast Cells in Three-dimensional Culture and In Vivo by Integrin Blocking Antibodies," *J. Cell Biol.* 137: 231-245 (1997), which are hereby incorporated by reference in their entirety). A specific repertoire of integrins expressed on tumour-derived exosomes, distinct from tumor cells, is defined which dictates exosome adhesion to specific cell-types and ECM molecules in particular organs. Importantly, exosomes expressing ITG$\alpha_v\beta_5$ specifically bind to Kupffer cells, mediating liver tropism, whereas exosomal ITG$\alpha_6\beta_4$ and ITG$\alpha_6\beta_1$ bind lung-resident fibroblasts and epithelial cells, governing lung tropism (FIG. 8C).

Interestingly, bone-tropic exosomes expressed a limited integrin repertoire but were capable of inducing vascular leakiness in the lung despite lack of uptake in the lung parenchyma. These results suggest that whereas induction of vascular leakiness may be the first exosome-mediated step during the metastatic cascade, it is insufficient to promote metastasis. Thus, integrin-independent mechanisms may mediate vascular leakiness and exosome involvement in bone metastasis.

Cell type-specific exosome integrin uptake promoted pro-migratory and pro-inflammatory S100 gene upregulation (S100A4, -A6, -A10, -A11, -A13, and -A16 in lung fibroblasts; S100P and -A8 in Kupffer cells). Notably, tumour exosomes failed to elicit S100 upregulation in lung epithelial cells, highlighting the cell-type specificity of exosomal education. Since S100A4 regulates lung metastasis (Grum-Schwensen et al., "Lung Metastasis Fails in MMTV-PyMT Oncomice Lacking S100A4 Due to a T-cell Deficiency in Primary Tumors," *Cancer Res.* 70:936-947 (2010), which is hereby incorporated by reference in its entirety) and is controlled by ITG$\alpha_6\beta_4$ (Chen et al., "Integrin Alpha6beta4 Controls the Expression of Genes Associated With Cell Motility, Invasion, and Metastasis, Including S100A4/Metastasin," *J. Biol. Chem.* 284:1484-1494 (2009), which is hereby incorporated by reference in its entirety), it is concluded that exosomal ITG$\alpha_6\beta_4$ activates the Src-S100A4 axis in lung fibroblasts during pre-metastatic niche formation. Therefore, it is proposed that exosomal integrins not only promote adhesion, but also trigger signalling pathways and inflammatory responses in target cells resulting in the education of that organ rendering it permissive for the growth of metastatic cells.

The proof of principle that integrin-blocking decoy peptides successfully ablate tumour exosome adhesion in an integrin-specific and organ-specific manner is provided. Thus, it is no longer surprising that targeting ITG$\alpha_v$ in breast cancer cells prevented metastasis to other organs but not to the lung (Bauerle et al., "Cilengitide Inhibits Progression of Experimental Breast Cancer Bone Metastases as Imaged Noninvasively Using VCT, MRI and DCE-MRI in a Longitudinal In Vivo Study," *Int. J. Cancer* 128:2453-2462 (2011); Wu et al., "Targeting AlphaV-integrins Decreased Metastasis and Increased Survival in a Nude Rat Breast Cancer Brain Metastasis Model," *J. Neurooncol.* 110:27-36 (2012); Zhao et al., "Tumor Alphavbeta3 Integrin is a Therapeutic Target for Breast Cancer Bone Metastases," *Cancer Res.* 67:5821-5830 (2007), which are hereby incorporated by reference in their entirety). However, strategies targeting exosomal integrins may effectively block organ-specific metastasis. Collectively, these data suggest that exosomal integrins and exosome-inducible S100 molecules in target cells represent candidates for anti-metastatic combination therapies.

Overall, these findings suggest that circulating tumour-derived exosomes may be useful not only to predict metastatic propensity (Lu et al., "Organotropism of Breast Cancer Metastasis," *Journal of Mammary Gland Biology and Neoplasia* 12:153-162 (2007), which is hereby incorporated by reference in its entirety), but also to determine organ sites of future metastasis. It is believed that exosomes perform distinct roles during each of the sequential steps (i.e., vascular leakiness, stromal cell education at organotropic sites, BM-derived cell education and recruitment) necessary to complete pre-metastatic niche evolution (Peinado et al., "Melanoma Exosomes Educate Bone Marrow Progenitor Cells Toward a Pro-Metastatic Phenotype Through MET," *Nat. Med.* 18:883-891 (2012); Costa-Silva et al., "Pancreatic Cancer Exosomes Initiate Pre-Metastatic Niche Formation in the Liver," *Nat. Cell. Biol.* (2015); Tominaga et al., "Brain Metastatic Cancer Cells Release MicroRNA-181c-containing Extracellular Vesicles Capable of Destructing Blood-brain Barrier," *Nat. Commun.* 6:6716 (2015), which are hereby incorporated by reference in their entirety).

Future studies will focus on identifying exosomal integrins and proteins that could dictate metastasis to other organs, as well as further exploring the potential of exosomal ITG$\alpha_2\beta_1$ as a marker and driver of all cancer metastasis. These findings demonstrate an important role for exosomes in dictating organ-specific metastasis, thus providing a basis for deciphering the mystery of organotropism.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method comprising:
selecting a subject having cancer;
obtaining, from the selected subject, a sample containing exosomes;
contacting the exosomes with one or more reagents suitable to determine expression levels, on said exosomes, of brain specific integrins comprising ITGα$_v$, and/or ITGβ$_3$;
detecting (A) an increase in the expression levels of brain specific integrins on said exosomes relative to (i) the average expression levels of the selected brain specific integrins in a non-cancerous exosomal sample; (ii) the average expression levels of the selected brain specific integrins in a non-metastatic cancerous exosomal sample; or (iii) the expression levels of the selected brain specific integrins in an exosomal sample taken from the selected subject at an earlier time point; or (B) no change in the expression levels of the brain specific integrins on said exosomes relative to the average expression level of the selected brain specific integrins in a metastatic cancerous exosomal sample;
prognosing that the cancer is likely to metastasize to the brain based on said detecting; and
administering an inhibitor of ITGα$_v$ and/or of ITGβ$_3$ to the selected subject where metastasis to the brain is prognosed to be likely.

2. A method comprising:
selecting a subject having cancer;
obtaining, from the selected subject, a sample containing exosomes;
contacting the exosomes with one or more reagents suitable to determine expression levels, on said exosomes, of lung specific integrins comprising ITGα$_6$, ITGβ$_1$, and/or ITGβ$_4$;
detecting (A) an increase in the expression levels of lung specific integrins on said exosomes relative to (i) the average expression levels of the selected lung specific integrins in a non-cancerous exosomal sample; (ii) the average expression levels of the selected lung specific integrins in a non-metastatic cancerous exosomal sample; or (iii) the expression levels of the selected lung specific integrins in an exosomal sample taken from the selected subject at an earlier time point; or (B) no change in the expression levels of the lung specific integrins on said exosomes relative to the average expression level of the selected lung specific integrins in a metastatic cancerous exosomal sample;
prognosing that the cancer is likely to metastasize to the lungs based on said detecting; and
administering an inhibitor of ITGα$_6$, ITGβ$_1$, and/or ITGβ$_4$ to the selected subject where metastasis to the lung is prognosed to be likely.

3. A method comprising:
selecting a subject having cancer;
obtaining, from the selected subject, a sample containing exosomes;
contacting the exosomes with one or more reagents suitable to determine expression levels, on said exosomes, of liver specific integrins comprising ITGα$_v$ and/or ITGβ$_5$;
detecting (A) an increase in the expression levels of liver specific integrins on said exosomes relative to (i) the average expression levels of the selected liver specific integrins in a non-cancerous exosomal sample; (ii) the average expression levels of the selected liver specific integrins in a non-metastatic cancerous exosomal sample; or (iii) the expression levels of the selected liver specific integrins in an exosomal sample taken from the selected subject at an earlier time point; or (B) no change in the expression levels of the liver specific integrins on said exosomes relative to the average expression level of the selected liver specific integrins in a metastatic cancerous exosomal sample;
prognosing that the cancer is likely to metastasize to the liver based on said detecting; and
administering an inhibitor of ITGα$_v$ and/or ITGβ$_5$ to the selected subject where metastasis to the liver is prognosed to be likely.

4. The method of claim 3 further comprising:
separating tumor exosomes from normal exosomes prior to said contacting.

5. A method comprising:
selecting a subject having cancer;
obtaining, from the selected subject, a sample containing exosomes;
contacting the exosomes with one or more reagents suitable to determine expression levels, on said exosomes, of one or more of the integrin groups selected from the group consisting of a brain specific group of integrins comprising ITGα$_v$ and/or ITGβ$_3$; a lung specific group of integrins comprising ITGα$_6$, ITGβ$_1$, and/or ITGβ$_4$; and a liver specific group of integrins comprising ITGα$_v$ and/or ITGβ$_5$;
detecting (A) an increase in the expression levels of the selected one or more integrin groups on said exosomes relative to (i) the average expression levels of the selected one or more integrin groups in a non-cancerous exosomal sample; (ii) the average expression levels of the selected one or more integrin groups in a non-metastatic cancerous exosomal sample; or (iii) the expression levels of the selected one or more integrin groups in an exosomal sample taken from the selected subject at an earlier time point; or (B) no change in the expression levels of the selected one or more integrin groups on said exosomes relative to the average expression level of the selected one or more integrin groups in a metastatic cancerous exosomal sample;
prognosing that the cancer is likely to metastasize to a site selected from the group consisting of the brain, the lung, and the liver, respectively, based on said detecting the brain specific group, the lung specific group, and the liver specific group of integrins; and
administering, to said selected subject, a cancer therapeutic selected for suitability based on said detecting.

6. The method of claim 5, wherein the cancer therapeutic is selected from the group consisting of abciximab, etaracizumab, abegrin, CNTO95, cilengitide, eptifibatide, ATN-161, vipegitide, MK0429, E7820, Vitaxin, 5247, PSK1404, 5137, and HYD-1.

7. The method of claim 5, wherein the cancer therapeutic is an ITGα$_v$β$_3$, ITGα$_v$β$_5$, or ITGα$_6$β$_1$ inhibitor.

8. The method of claim 7, wherein the cancer therapeutic is an ITGα$_v$ β$_3$ inhibitor which is selected from the group consisting of etaracizumab, Vitaxin, CNTO95 antibody, cilengitide, S247, PSK1404, and 5137.

9. The method of claim 7, wherein the cancer therapeutic is an ITGα$_v$β$_5$ inhibitor which is selected from the group consisting of CNTO95 antibody and cilengitide.

10. The method of claim 7, wherein the cancer therapeutic is an ITGα$_6$β$_1$ inhibitor which is HYD-1.

11. The method of claim 5, wherein said method is carried out to treat or prevent metastasis.

12. The method of claim 5, wherein said one or more reagents suitable to determine expression levels of one or more integrin groups in the sample are suitable for measuring RNA expression level or protein expression level.

13. A method of treating a subject having cancer that has metastasized to the brain, lung, or liver, or having cancer that is at risk of metastasizing to the brain, lung, or liver, said method comprising:
selecting a subject having cancer;
obtaining, from the selected subject, a sample containing exosomes;
contacting the exosomes with one or more reagents suitable to determine expression levels, on said exosomes, of one or more of the integrin groups selected from the group consisting of a brain specific group of integrins comprising ITGα$_v$ and/or ITGβ$_3$; a lung specific group of integrins comprising ITGα$_6$, ITGβ$_1$, and/or ITGβ$_4$; and a liver specific group of integrins comprising ITGα$_v$ and/or ITGβ$_5$;
detecting (A) an increase in the expression levels of the selected one or more integrin groups on said exosomes relative to (i) the average expression levels of the selected one or more integrin groups in a non-cancerous exosomal sample; (ii) the average expression levels of the selected one or more integrin groups in a non-metastatic cancerous exosomal sample; (iii) the expression levels of the selected one or more integrin groups in an exosomal sample taken from the selected subject at an earlier time point; or (B) no change in the expression levels of the selected one or more integrin groups on said exosomes relative to the average expression level of the selected one or more integrin groups in a metastatic cancerous exosomal sample;
prognosing that the cancer is likely to metastasize to a site selected from the group consisting of the brain, the lung, and the liver, respectively, based on said detecting the brain specific group, the lung specific group, and the liver specific group of integrins;
selecting a therapeutic integrin inhibitor based on said detecting; and
administering to the selected subject (i) an inhibitor of ITGα$_v$ and/or ITGβ$_3$ as the therapeutic integrin inhibitor when the subject has an exosomal integrin profile indicative of brain metastasis; (ii) an inhibitor of ITGα$_6$, ITGβ$_1$, and/or ITGβ$_4$ as the therapeutic integrin inhibitor when the subject has an exosomal integrin profile indicative of lung metastasis; and (iii) an inhibitor of ITGα$_v$ and/or ITGβ$_5$ as the therapeutic integrin inhibitor when the subject has an exosomal integrin profile indicative of liver metastasis, in order to treat the cancer.

14. The method of claim 1 further comprising:
separating tumor exosomes from normal exosomes prior to said contacting.

15. The method of claim 2 further comprising:
separating tumor exosomes from normal exosomes prior to said contacting.

\* \* \* \* \*

SEQUENCE LISTING

<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Artificial Amino acid HYD-1 peptide

<400> SEQUENCE: 1

Lys Ile Lys Met Val Ile Ser Trp Lys Gly
1               5                   10

<210> SEQ ID NO 2

```
<211> LENGTH: 58
<212> TYPE: DNA
<213> ORGANISM: Artificial Sequence
<220> FEATURE:
<223> OTHER INFORMATION: Artificial DNA oligo

<400> SEQUENCE: 2
ccgggagggt gtcatcacca ttgaactcga gttcaatggt gatgacaccc tcttttg        58

<210> SEQ ID NO 3
<211> LENGTH: 21
<212> TYPE: DNA
<213> ORGANISM: Artificial Sequence
<220> FEATURE:
<223> OTHER INFORMATION: DNA human ITGB4 gene fragment

<400> SEQUENCE: 3
gagggtgtca tcaccattga a                                               21

<210> SEQ ID NO 4
<211> LENGTH: 21
<212> TYPE: DNA
<213> ORGANISM: Artificial Sequence
<220> FEATURE:
<223> OTHER INFORMATION: DNA human ITGB5 gene fragment

<400> SEQUENCE: 4
agcttgttgt cccaatgaaa t                                               21

<210> SEQ ID NO 5
<211> LENGTH: 58
<212> TYPE: DNA
<213> ORGANISM: Artificial Sequence
<220> FEATURE:
<223> OTHER INFORMATION: Artificial DNA oligo

<400> SEQUENCE: 5
ccggagcttg ttgtcccaat gaaatctcga gatttcattg ggacaacaag ctttttg        58
```